US009493464B2

(12) United States Patent
Roush et al.

(10) Patent No.: US 9,493,464 B2
(45) Date of Patent: Nov. 15, 2016

(54) WEE1 DEGRADATION INHIBITORS

(71) Applicant: The Scripps Research Institute, La Jolla, CA (US)

(72) Inventors: William R. Roush, Jupiter, FL (US); Ronald Rahaim, Palm Beach Gardens, FL (US); Mathieu Bibian, Creissels (FR)

(73) Assignee: The Scripps Research Institute, La Jolla, CA (US)

( * ) Notice: Subject to any disclaimer, the term of this patent is extended or adjusted under 35 U.S.C. 154(b) by 0 days.

(21) Appl. No.: 14/381,151

(22) PCT Filed: Feb. 26, 2013

(86) PCT No.: PCT/US2013/027784
§ 371 (c)(1),
(2) Date: Aug. 26, 2014

(87) PCT Pub. No.: WO2013/130461
PCT Pub. Date: Sep. 6, 2013

(65) Prior Publication Data
US 2015/0274729 A1    Oct. 1, 2015

Related U.S. Application Data

(60) Provisional application No. 61/604,683, filed on Feb. 29, 2012.

(51) Int. Cl.
C07D 473/34 (2006.01)
C07D 473/32 (2006.01)
C07D 473/16 (2006.01)
C07D 519/00 (2006.01)

(52) U.S. Cl.
CPC .......... *C07D 473/32* (2013.01); *C07D 473/16* (2013.01); *C07D 473/34* (2013.01); *C07D 519/00* (2013.01)

(58) Field of Classification Search
CPC .................................................. C07D 473/34
See application file for complete search history.

(56) References Cited

U.S. PATENT DOCUMENTS

| 6,413,974 B1 | 7/2002 | Dumont et al. |
| 2003/0069259 A1 | 4/2003 | Borcherding et al. |
| 2006/0079564 A1 | 4/2006 | Jansen |
| 2008/0039477 A1 | 2/2008 | Freyne et al. |
| 2009/0203638 A1 | 8/2009 | Miljkovic et al. |
| 2009/0275564 A1 | 11/2009 | Albers et al. |
| 2009/0281100 A1 | 11/2009 | Barsanti et al. |
| 2009/0312320 A1 | 12/2009 | Albers et al. |
| 2010/0311768 A1 | 12/2010 | Meijer et al. |
| 2012/0202785 A1* | 8/2012 | Heald ........... C07D 401/12 514/210.18 |

FOREIGN PATENT DOCUMENTS

| WO | WO-99/43676 A2 | 9/1999 |
| WO | WO-00/44750 A1 | 8/2000 |
| WO | WO-02/098878 A1 | 12/2002 |
| WO | WO-2004/014913 A2 | 2/2004 |
| WO | WO-2005/016528 A2 | 2/2005 |
| WO | WO-2008/094737 A2 | 8/2008 |
| WO | WO-2009/034386 A1 | 3/2009 |
| WO | WO-2009/067607 A2 | 5/2009 |
| WO | WO 2011123751 A2 * | 10/2011 ........... C07D 401/14 |
| WO | WO-2013/130461 A1 | 9/2013 |

OTHER PUBLICATIONS

Byrn, Stephen. Solid-State Chemistry of Drugs, 2nd edition, (1999). Hydrates and Solvates, 233-247.*
Morissette, Sherry. Adv. Drug Delivery Rev. 2004, 56, 275-300.*
Rouhi, A. M., Chem. & Eng. News, (2003), 81(8), 32-35.*
"International Application Serial No. PCT/US2013/027784, International Search Report mailed May 2, 2013", 4 pgs.
"International Application Serial No. PCT/US2013/027784, Written Opinion mailed May 2, 2013", 5 pgs.
Arora, Amit, et al., "Role of tyrosine kinase inhibitors in cancer therapy", J Pharmacol Exp Ther., 315(3), (Dec. 2005), 971-9.
Ayad, Nagi G., et al., "Tome-1, a trigger of mitotic entry, is degraded during G1 via the APC.", Cell, 113(1), (Apr. 4, 2003), 101-13.
Bryja, Vitezslav, et al., "Wnt-3a utilizes a novel low dose and rapid pathway that does not require casein kinase 1-mediated phosphorylation of Dvl to activate beta-catenin.", Cell Signal., 19(3), (Mar. 2007), 610-6.
Conlon, Ian, et al., "Size control in animal development.", Cell, 96(2), (Jan. 22, 1999), 235-44.
Ding, S., et al., "A concise and traceless linker strategy toward combinatorial libraries of 2,6,9-substituted purines", J Org Chem., 66(24), (Nov. 30, 2001), 8273-6.
Ding, S., et al., "Expanding the diversity of purine libraries", Tetrahedron Letters, 41(50), (Dec. 10, 2001), 8751-8755.
Flajolet, Marc, et al., "Regulation of Alzheimer's disease amyloid-beta formation by casein kinase I.", Proc Natl Acad Sci U S A., 104(10), (Mar. 6, 2007), 4159-64.
Gao, Daming, et al., "Phosphorylation by Akt1 promotes cytoplasmic localization of Skp2 and impairs APC-Cdh1-mediated Skp2 destruction", Nature Cell Biology, 11(4), (Apr. 2009), 397-408.
Gautier, Jean, et al., "cdc25 is a specific tyrosine phosphatase that directly activates p34cdc2.", Cell, 67(1), (Oct. 4, 1991), 197-211.
Haesslein, J. L, et al., "Recent advances in cyclin-dependent kinase inhibition. Purine-based derivatives as anti-cancer agents. Roles and perspectives for the future.", Curr Top Med Chem., 2(9), (Dec. 2002), 1037-50.
Hatten, Mary E., et al., "Mechanisms of Neural Patterning and Specification in the Developing Cerebellum", Annu. Rev. Neurosci. 18:385-408, (1995), 385-408.

(Continued)

*Primary Examiner* — Golam M M Shameem
*Assistant Examiner* — Laura Daniel
(74) *Attorney, Agent, or Firm* — Geoffrey K. Cooper; Thomas Fitting

(57) ABSTRACT

The invention provides compounds that inhibit the degradation of Wee1. The compounds of the present invention are generally N-((1H-benzo[d]imidazol-2-yl)methyl)-9H-purin-6-amines. Compounds of the invention can be used for treatment of malconditions in patients for which inhibition of Wee1 is medically indicated, for example cancer, Alzheimer's, neurological disorders, psychiatric disorders, or inflammation-related disorders.

2 Claims, 15 Drawing Sheets

(56) References Cited

OTHER PUBLICATIONS

Hatten, Mary E, "Neuronal regulation of astroglial morphology and proliferation in vitro.", J Cell Biol., 100(2), (Feb. 1985), 384-96.

Husseman, J. W, et al., "Mitotic activation: a convergent mechanism for a cohort of neurodegenerative diseases.", Neurobiol Aging., 21(6), (Nov.-Dec. 2000), 815-28.

Kellogg, Douglas R, "Wee1-dependent mechanisms required for coordination of cell growth and cell division.", J Cell Sci., 116(Pt 24), (Dec. 15, 2003), 4883-90.

Kiviharju-Af Hallstrom, Taija M., et al., "Human prostate epithelium lacks Wee1A-mediated DNA damage-induced checkpoint enforcement", Proc. Natl. Acad. Sci. USA, 104(17), (Apr. 24, 2007), 7211-7216.

Knippschild, Uwe, et al., "The casein kinase 1 family: participation in multiple cellular processes in eukaryotes.", Cell Signal., 17(6), (Jun. 2005), 675-89.

Lee, Youngsoo, et al., "A molecular fingerprint for medulloblastoma.", Cancer Res., 63(17), (Sep. 1, 2003), 5428-37.

Li, Guibin, et al., "Casein kinase 1 delta phosphorylates tau and disrupts its binding to microtubules.", J Biol Chem., 279(16), (Apr. 16, 2004), 15938-45.

Lu, Zhimin, et al., "Degradation of activated protein kinases by ubiquitination.", Annu Rev Biochem., 78, (2009), 435-75.

Michael, W. M, et al., "Coupling of mitosis to the completion of S phase through Cdc34-mediated degradation of Wee1.", Science, 282(5395), (Dec. 4, 1998), 1886-9.

Muller, Myriam, et al., "Persistence of the cell-cycle checkpoint kinase Wee1 in SadA- and SadB-deficient neurons disrupts neuronal polarity.", J Cell Sci., 123(Pt 2), (Jan. 15, 2010), 286-94.

Oumata, Nassima, et al., "Roscovitine-derived, dual-specificity inhibitors of cyclin-dependent kinases and casein kinases 1.", J Med Chem., 51(17), (Sep. 11, 2008), 5229-42.

Owens, Laura, et al., "Activation domain-dependent degradation of somatic Wee1 kinase.", The Journal of Biological Chemistry, 285(9), (Feb. 26, 2010), 6761-6769.

Rena, Graham, et al., "D4476, a cell-permeant inhibitor of CK1, suppresses the site-specific phosphorylation and nuclear exclusion of FOXO1a.", EMBO Rep., 5(1), (Jan. 2004), 60-5.

Smith, Anthony, et al., "Redundant ubiquitin ligase activities regulate wee1 degradation and mitotic entry.", Cell Cycle, 6(22), (Nov. 15, 2007), 2795-9.

Thompson, Margaret C., et al., "Genomics Identifies Medulloblastoma Subgroups That are Enriched for Specific Genetic Alterations", Journal of Clinical Oncology, 24(12), (Apr. 20, 2006), 1924-1931.

Tomashevski, A., et al., "Constitutive Wee1 activity in adult brain neurons with M phase-type alterations in Alzheimer neurodegeneration.", J Alzheimers Dis., 3(2), (Apr. 2001), 195-207.

Verma, Rati, et al., "Ubistatins inhibit proteasome-dependent degradation by binding the ubiquitin chain.", Science, 306(5693), (Oct. 1, 2004), 117-20.

Walton, Kevin M., et al., "Selective inhibition of casein kinase 1 epsilon minimally alters circadian clock period", J Pharmacol Exp Ther., 330(2), (Aug. 2009), 430-9.

Watanabe, Nobumoto, et al., "Cyclin-dependent kinase (CDK) phosphorylation destabilizes somatic Wee1 via multiple pathways.", Proc Natl Acad Sci U S A., 102(33), (Aug. 16, 2005), 11663-8.

Watanabe, Nobumoto, et al., "M-phase kinases induce phospho-dependent ubiquitination of somatic Wee1 by SCFbeta-TrCP.", Proc Natl Acad Sci U S A., 101(13), (Mar. 30, 2004), 4419-24.

Watanabe, Nobumoto, et al., "Regulation of the human WEE1Hu CDK tyrosine 15-kinase during the cell cycle.", EMBO J., 14(9), (May 1, 1995), 1878-91.

Yoshida, T., et al., "The clinical significance of Cyclin B1 and Wee1 expression in non-small-cell lung cancer.", Ann Oncol., 15(2), (Feb. 2004), 252-6.

\* cited by examiner

| Compound | R₁ | R₂ | EC$_{50}$ (μmol) |
|---|---|---|---|
| SR-1-653234 | thiophene | morpholine | 0.77 |
| SR-1-655534 | isopropyl | NH-pyridine | 3.8 (X = CH) |
| SR-1-660754 | isopropyl | NH-pyrazine | 4.0 (X = N) |
| SR-1-648126 | isopropyl | morpholine | 5.3 |
| SR-1-649967 | cyclohexyl | morpholine | 4.3 |
| SR-1-656428 | isopropyl | NH-pyrimidine | 4.4 |
| SR-1-648378 | thiophene | piperazine-pyridine | 4.3 |
| SR-1-658807 | thiophene | phenyl-C(O)NH-cyclopropyl | 4.1 |
| SR-1-660983 | thiophene | NH-pyrimidine | 3.8 |

SR-653234, X = H
SR-1277, X = NO₂

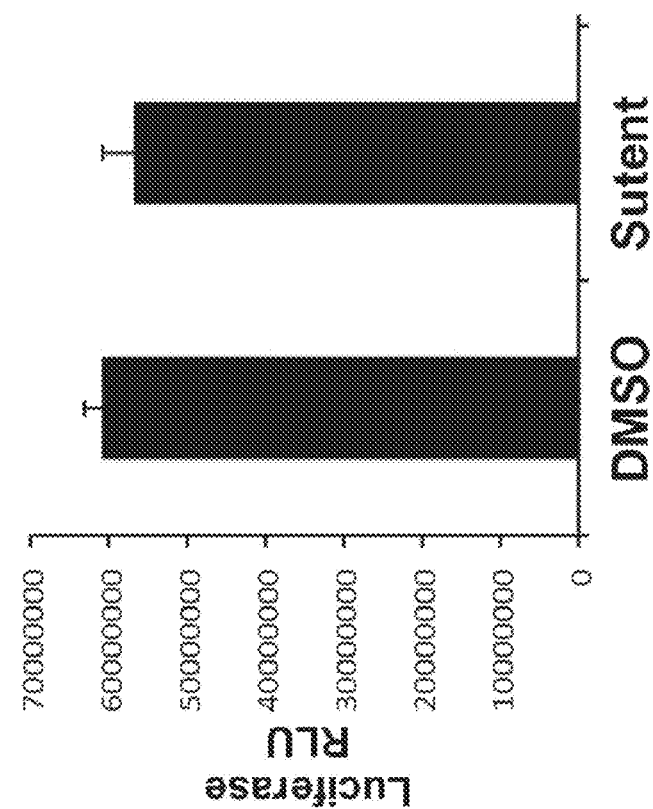
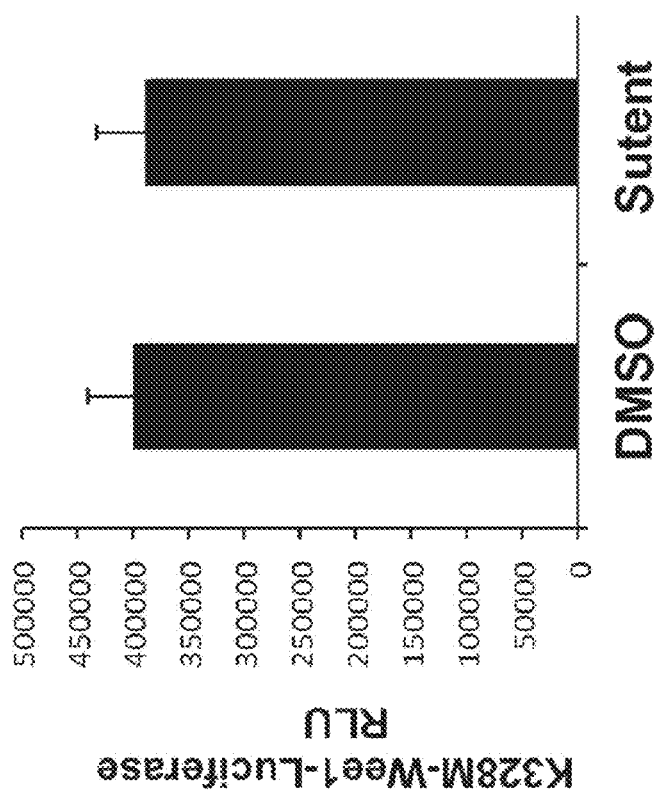

WEE1 DEGRADATION INHIBITORS

CROSS-REFERENCE TO RELATED APPLICATIONS

This application is a U.S. national stage application filed under 35 U.S.C. §371 from International Application Serial No. PCT/US2013/027784, which was filed Feb. 26, 2013, and published as WO 2013/130461 on Sep. 6, 2013, and which claims the benefit of priority of U.S. Provisional Application Ser. No. 61/604,683, filed Feb. 29, 2012, entitled "WEE1 DEGRADATION INHIBITORS," which applications and publication are incorporated by reference as if reproduced herein and made a part hereof in their entirety, and the benefit of priority of each of which is claimed herein.

STATEMENT OF GOVERNMENT SUPPORT

This work was supported by Grant Number U54 MH084512, 1R21NS056991-01, and 1R01NS067289, from the National Institutes of Health. The government has certain rights in this invention.

BACKGROUND OF THE INVENTION

Many malconditions have in common a trait of excessive cell proliferation. Examples include cancer, Alzheimer's, neurological disorders, psychiatric disorders, and inflammation-related disorders.

The Wee1 protein, a tyrosine kinase, is a mitosis inhibitor. Increasing levels of Wee1 can block cell proliferation. Wee1 levels are low in non-small cell lung cancer. The prostate epithelium has low levels of Wee1, and increasing Wee1 levels in the prostate epithelium can reduce prostate cell proliferation. Wee1 levels are reduced in Alzheimer's patients.

Wee1 can act as a tumor suppressor by inhibiting mitotic entry. Cellular levels of Wee1 are controlled by ubiquitination by E3 ligases and subsequent proteosomic degradation. Cdk1/cyclin B is held in an inactive state during G2 (growth phase) since Wee1 overcomes Cdc25 activity through phosphorylation of Cdk1 at tyrosine 15. As G2 progresses, phosphorylated Wee1 accumulates and is recognized by E3 ubiquitin ligases and is degraded via the proteosome. Cdc25 is then able to remove the inhibitory phosphorylation on Cdk1 and mitotic entry proceeds.

Thus, inhibition of the degradation of Wee1 can provide a route for cell cycle-based therapy of cancer and other malconditions with excessive cell proliferation.

SUMMARY OF THE INVENTION

The present invention relates to compounds that can inhibit the degradation of Wee1; to pharmaceutical compositions including a compound of the invention; to methods of treatment of malconditions where inhibition of Wee1 is medically indicated.

In various embodiments, the invention provides a compound of formula (I),

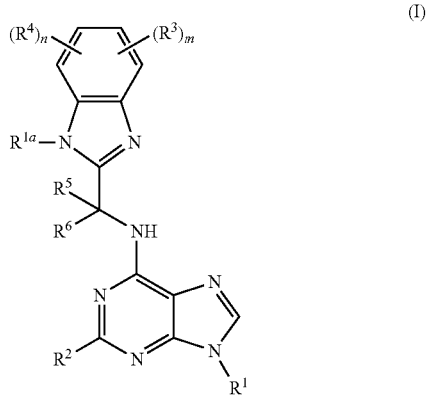

wherein
$R^1$ and $R^{1a}$ are each independently selected from the group consisting of hydrogen, deuterium, $(CH_2)_{0-4}N(R)_2$, $(CH_2)_{0-4}SO_3R$, $(CH_2)_{0-4}C(O)R$, $(CH_2)_{0-4}C(O)C(O)R$, $(CH_2)_{0-4}C(O)CH_2C(O)R$, $(CH_2)_{0-4}C(S)R$, $(CH_2)_{0-4}C(O)OR$, $(CH_2)_{0-4}OC(O)R$, $(CH_2)_{0-4}OC(O)OR$, $(CH_2)_{0-4}C(O)N(R)_2$, $OC(O)N(R)_2$, $(CH_2)_{0-4}C(S)N(R)_2$, $(CH_2)_{0-4}NHC(O)R$, $(CH_2)_{0-4}N(R)SO_2R$, $(CH_2)_{0-4}N(R)SO_2N(R)_2$, $(CH_2)_{0-4}N(R)C(O)OR$, $(CH_2)_{0-4}N(R)C(O)R$, $(CH_2)_{0-4}N(R)C(S)R$, $(CH_2)_{0-4}N(R)C(O)N(R)_2$, $(CH_2)_{0-4}N(R)C(S)N(R)_2$, $(CH_2)_{0-4}N(COR)COR$, $(CH_2)_{0-4}N(OR)R$, $(CH_2)_{0-4}C(=NH)N(R_2)$, $(CH_2)_{0-4}C(O)N(OR)R$, $(CH_2)_{0-4}C(=NOR)R$, $(C_{1-4})$alkyl, $(C_{1-4})$alkoxy, $(C_{1-4})$acyloxy, cycloalkyl, heterocyclyl, aryl, and heteroaryl; wherein any alkyl, alkoxy, acyloxy, cycloalkyl, heterocyclyl, aryl, heteroaryl can be mono- or independently multi-substituted with J, $(C_{1-6})$alkyl, $(C_{2-6})$alkenyl, $(C_{2-6})$alkynyl, $(C_{1-6})$haloalkyl, $(C_{1-6})$alkoxy, $(C_{1-6})$haloalkoxy, cycloalkyl$(C_{0-6})$alkyl, heterocyclyl$(C_{0-6})$alkyl, aryl$(C_{0-6})$alkyl, or heteroaryl$(C_{0-6})$alkyl, of which any alkyl, alkenyl, alkynyl, haloalkyl, alkoxy, haloalkoxy, cycloalkyl, aryl, heterocyclyl, or heteroaryl can be further substituted with J;

$R^2$, $R^3$, $R^4$, $R^5$, and $R^6$ each are independently selected from the group consisting of F, Cl, Br, I, OR, CN, $CF_3$, $OCF_3$, $NO_2$, R, $(CH_2)_{0-4}N(R)_2$, $(CH_2)_{0-4}SR$, $(CH_2)_{0-4}SOR$, $(CH_2)_{0-4}SO_2R$, $(CH_2)_{0-4}SO_2N(R)_2$, $(CH_2)_{0-4}SO_3R$, $(CH_2)_{0-4}C(O)R$, $(CH_2)_{0-4}C(O)C(O)R$, $(CH_2)_{0-4}C(O)CH_2C(O)R$, $(CH_2)_{0-4}C(S)R$, $(CH_2)_{0-4}C(O)OR$, $(CH_2)_{0-4}OC(O)R$, $(CH_2)_{0-4}OC(O)OR$, $(CH_2)_{0-4}C(O)N(R)_2$, $(CH_2)_{0-4}OC(O)N(R)_2$, $(CH_2)_{0-4}C(S)N(R)_2$, $(CH_2)_{0-4}NHC(O)R$, $(CH_2)_{0-4}N(R)N(R)C(O)R$, $(CH_2)_{0-4}N(R)N(R)C(O)OR$, $(CH_2)_{0-4}N(R)N(R)CON(R_2)$, $(CH_2)_{0-4}N(R)SO_2R$, $(CH_2)_{0-4}N(R)SO_2N(R)_2$, $(CH_2)_{0-4}N(R)C(O)OR$, $(CH_2)_{0-4}N(R)C(O)R$, $(CH_2)_{0-4}N(R)C(S)R$, $(CH_2)_{0-4}N(R)C(O)N(R)_2$, $(CH_2)_{0-4}N(R)C(S)N(R)_2$, $(CH_2)_{0-4}N(COR)COR$, $(CH_2)_{0-4}N(OR)R$, $(CH_2)_{0-4}C(=NH)N(R_2)$, $(CH_2)_{0-4}C(O)N(OR)R$, $(CH_2)_{0-4}C(=NOR)R$, $(C_{1-4})$alkyl, $(C_{1-4})$alkoxy, $(C_{1-4})$acyloxy, cycloalkyl, heterocyclyl, aryl, and heteroaryl; wherein any alkyl, alkoxy, acyloxy, cycloalkyl, heterocyclyl, aryl, heteroaryl can be mono- or independently multi-substituted with J, $(C_{1-6})$alkyl, $(C_{2-6})$alkenyl, $(C_{2-6})$alkynyl, $(C_{1-6})$haloalkyl, $(C_{1-6})$alkoxy, $(C_{1-6})$haloalkoxy, cycloalkyl$(C_{1-6})$alkyl, heterocyclyl$(C_{0-6})$alkyl, aryl$(C_{0-6})$alkyl, or heteroaryl$(C_{0-6})$alkyl; wherein any alkyl, alkenyl, alkynyl, haloalkyl, alkoxy, haloalkoxy, cycloalkyl, aryl, heterocyclyl, or heteroaryl can be further substituted with J;

wherein m and n are each independently 0, 1, 2, or 3, provided m plus n is less or equal to 4;

wherein J independently at each occurrence is selected from the group consisting of F, Cl, Br, I, OR, CN, CF$_3$, OCF$_3$, NO$_2$, R, O, S, C(O), C(S), S(O), methylenedioxy, ethylenedioxy, N(R)$_2$, SR, SOR, SO$_2$R, SO$_2$N(R)$_2$, SO$_3$R, C(O)R, C(O)C(O)R, C(O)CH$_2$C(O)R, C(S)R, C(O)OR, OC(O)R, OC(O)OR, C(O)N(R)$_2$, OC(O)N(R)$_2$, C(S)N(R)$_2$, (CH$_2$)$_{0-4}$NHC(O)R, N(R)N(R)C(O)R, N(R)N(R)C(O)OR, N(R)N(R)CON(R$_2$), N(R)SO$_2$R, N(R)SO$_2$N(R)$_2$, N(R)C(O)OR, N(R)C(O)R, N(R)C(S)R, N(R)C(O)N(R)$_2$, N(R)C(S)N(R)$_2$, N(COR)COR, N(OR)R, C(=NH)N(R$_2$), C(O)N(OR)R, C(=NOR)R, (C$_{1-4}$)alkyl, (C$_{1-4}$)alkoxy, (C$_{1-4}$)acyloxy, cycloalkyl, heterocyclyl, aryl, and heteroaryl; wherein any alkyl, alkoxy, acyloxy, cycloalkyl, heterocyclyl, aryl, hetero aryl can be mono- or independently multi-substituted with R, (C$_{1-6}$)alkyl, (C$_{2-6}$)alkenyl, (C$_{2-6}$)alkynyl, (C$_{1-6}$)haloalkyl, (C$_{1-6}$)alkoxy, (C$_{1-6}$)haloalkoxy, cycloalkyl(C$_{0-6}$)alkyl, heterocyclyl(C$_{0-6}$)alkyl, aryl(C$_{0-6}$)alkyl, or heteroaryl(C$_{0-6}$)alkyl; wherein any alkyl, alkenyl, alkynyl, haloalkyl, alkoxy, haloalkoxy, cycloalkyl, aryl, heterocyclyl, or heteroaryl can be further mono- or independently multi-substituted with R; or wherein two R groups together with a nitrogen atom or with two adjacent nitrogen atoms to which they are bonded can together form a (C$_{3-8}$)heterocyclyl mono- or multi-substituted with R; optionally further including 1-3 additional hetero atoms selected from the group consisting of O, N, S, S(O) and S(O)$_2$;

wherein R is independently at each occurrence is selected from the group consisting of hydrogen, deuterium, F, Cl, Br, I, OH, CN, CF$_3$, OCF$_3$, NO$_2$, alkyl, cycloalkyl, cycloalkylalkyl, aryl, aralkyl, heterocyclyl, heterocyclylalkyl, heteroaryl, and heteroarylalkyl; wherein any alkyl, cycloalkyl, cycloalkylalkyl, aryl, aralkyl, heterocyclyl, heterocyclylalkyl, heteroaryl, or heteroarylalkyl is substituted with 0-3 J$^R$; or wherein two R groups together with a nitrogen atom or with two adjacent nitrogen atoms to which they are bonded can together form a (C$_{3-8}$)heterocyclyl substituted with 0-3 J$^R$; optionally further comprising 1-3 additional hetero atoms selected from the group consisting of O, N, S, S(O) and S(O)$_2$;

wherein any cycloalkyl, aryl, heterocyclyl, or heteroaryl can be fused, bridged, or in a spiro configuration with one or more additional optionally mono- or independently multi-J$^R$ substituted cycloalkyl, aryl, heterocyclyl, and heteroaryl, monocyclic, bicyclic, bicyclic or polycyclic, saturated, partially unsaturated, or aromatic rings;

wherein J$^R$ is independently at each occurrence is selected from the group consisting of F, Cl, Br, I, OR, CN, CF$_3$, OCF$_3$, NO$_2$, O, S, C(O), C(S), S(O), methylenedioxy, ethylenedioxy, N(R)$_2$, SR, SOR, SO$_2$R, SO$_2$N(R)$_2$, SO$_3$R, C(O)R, C(O)C(O)R, C(O)CH$_2$C(O)R, C(S)R, C(O)OR, OC(O)R, OC(O)OR, C(O)N(R)$_2$, OC(O)N(R)$_2$, C(S)N(R)$_2$, (CH$_2$)$_{0-4}$NHC(O)R, N(R)N(R)C(O)R, N(R)N(R)C(O)OR, N(R)N(R)CON(R$_2$), N(R)SO$_2$R, N(R)SO$_2$N(R)$_2$, N(R)C(O)OR, N(R)C(O)R, N(R)C(S)R, N(R)C(O)N(R)$_2$, N(R)C(S)N(R)$_2$, N(COR)COR, N(OR)R, C(=NH)N(R$_2$), C(O)N(OR)R, C(=NOR)R, (C$_{1-4}$)alkoxy, (C$_{1-4}$)acyloxy, cycloalkyl, heterocyclyl, aryl, and heteroaryl;

provided that the compound of formula (I) is not any of the following:

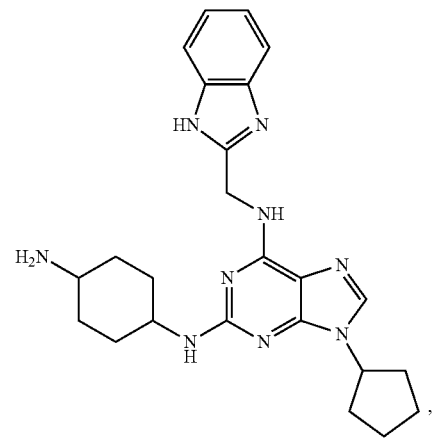

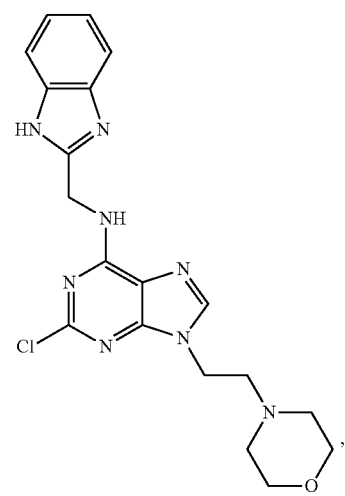

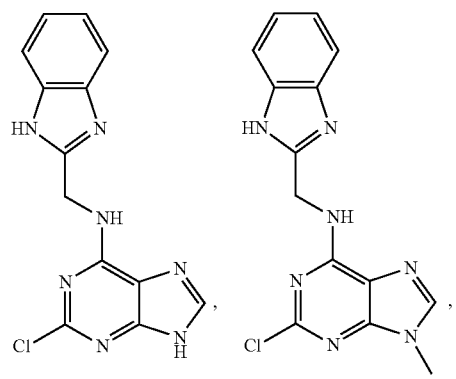

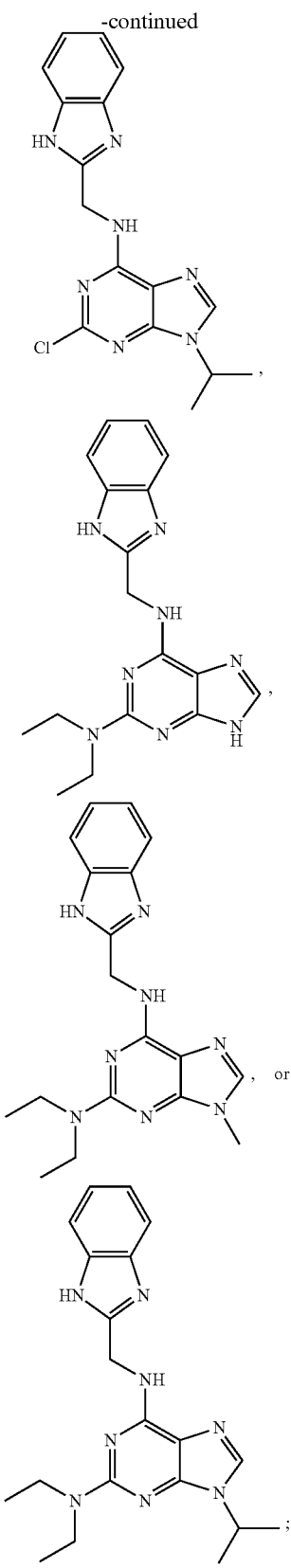

wherein the compound of formula (I) can be any stereoisomer thereof, or any salt, hydrate, solvate, prodrug, or metabolite thereof.

In various embodiments, the invention provides pharmaceutical compositions and combinations including a compound of the invention and a pharmaceutically acceptable carrier.

In various embodiments, the invention provides a method of reducing amyloid beta 40 production, including contacting one or more cells with an effective amount of a compound of the invention.

In various embodiments, the invention provides a method of reducing cell proliferation, including contacting one or more cells with an effective amount of a compound of the invention.

In various embodiments, the invention provides a method of inhibiting the degradation of Wee1, including contacting one or more cells with an effective amount of a compound of the invention.

In various embodiments, the invention provides a method of inhibiting casein kinase 1 (CK1), including contacting one or more cells with an effective amount of a compound of the invention.

In various embodiments, the invention provides a method of treating a malcondition in a patient for which inhibition of Wee1 is medically indicated, including administering to the patient a compound of the invention in a dose, at a frequency, and for a duration sufficient to provide a beneficial effect to the patient. In various embodiments, the malcondition can include cancer, Alzheimer's, and other malconditions, including: neurological disorders, psychiatric disorders, and inflammation-related disorders.

In various embodiments, the invention provides a method of synthesis of a compound of the invention.

BRIEF DESCRIPTION OF THE FIGURES

FIG. 7C is a bar chart of K328M-Wee1-Luciferase RLU of DMSO or sutent FIG. 7, D, is a bar chart of Luciferase Vector RLU of DMSO or sutent.

FIG. 10, B, is a Wee1 and Phospho-Y-Cdc2 Western blot of purified GCPs treated with DMSO, SR-653234, or SR-1277, with Skp-1 used as a loading control.

DETAILED DESCRIPTION OF THE INVENTION

Definitions

Figure 1A:
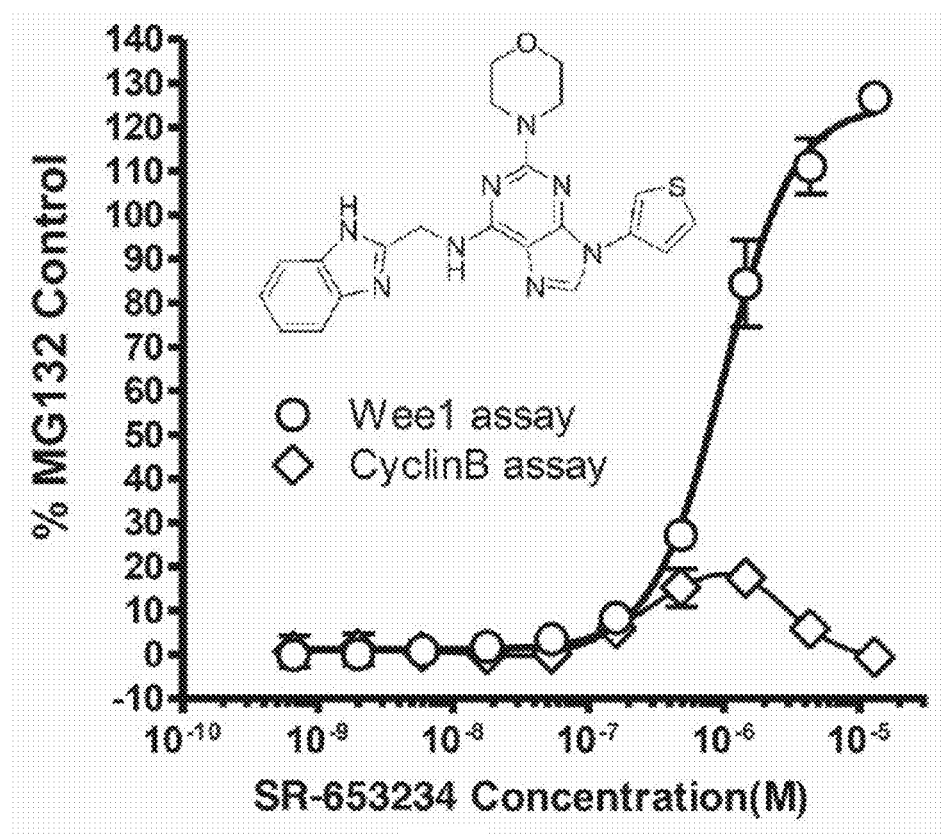
FIG. 1A is a graph of percent MG132 control versus SR-653234 concentration.
Figure 1B:
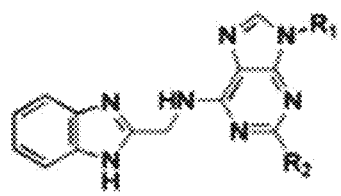
FIG. 1B is a list of structures of SR-653234 analogs with corresponding EC50 values for stabilization of K328M-Wee1-luciferase.
Figure 1C:
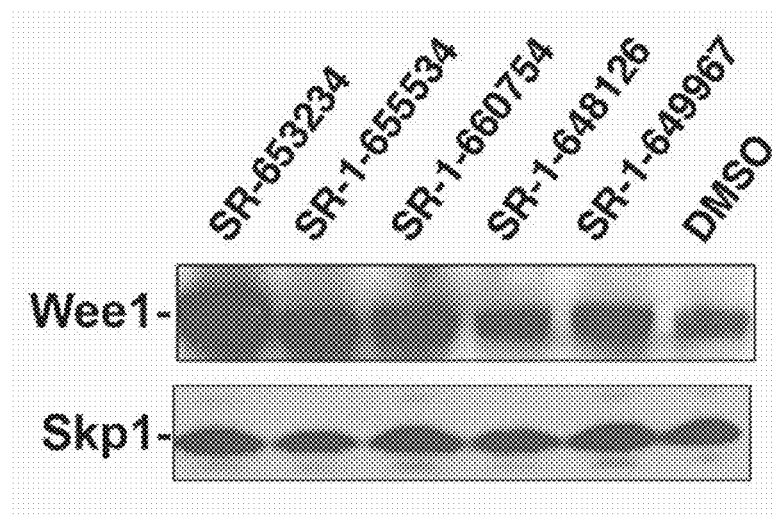
FIG. 1C is a Western blot of endogenous Wee1 or Skp1 (loading control) of HeLa cells.
Figure 1D:
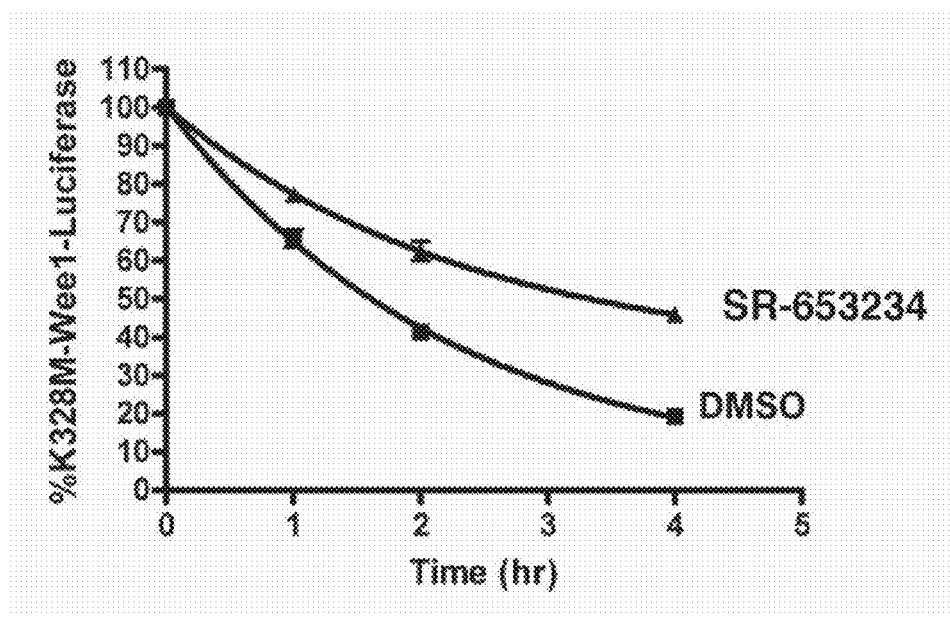
FIG. 1D is a graph of percent K328M-Wee1-Luciferase versus time for DMSO or SR-653234.
Figure 1E:
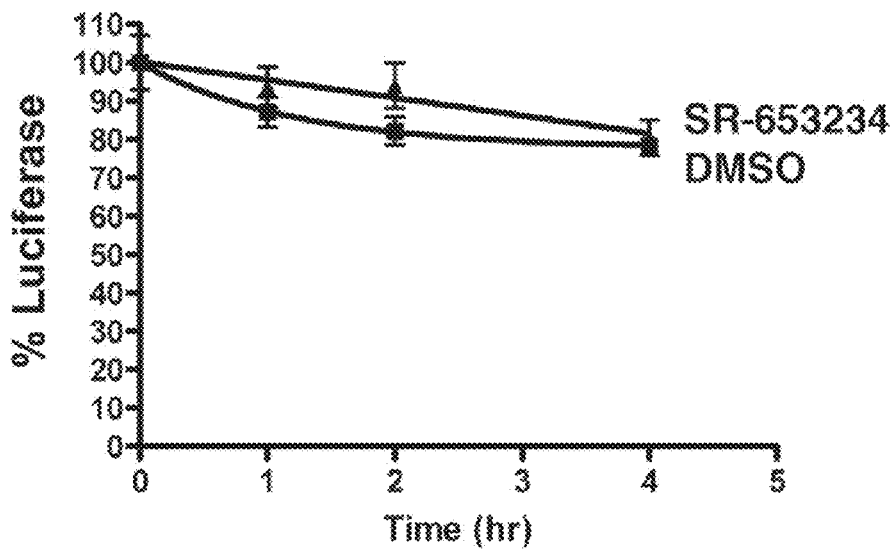
FIG. 1E is a graph of percent luciferase versus time for DMSO or SR-653234.
Figure 2A:
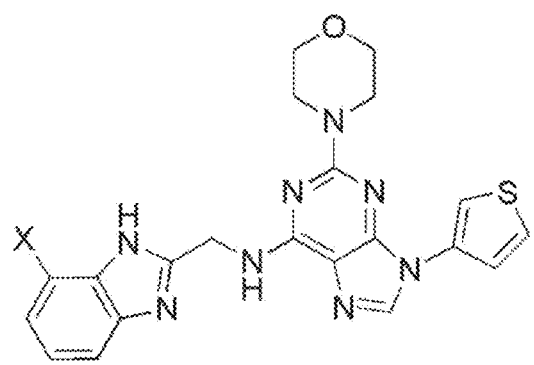
FIG. 2A depicts the chemical structures of SR-653234 and SR-1277.
Figure 2B:
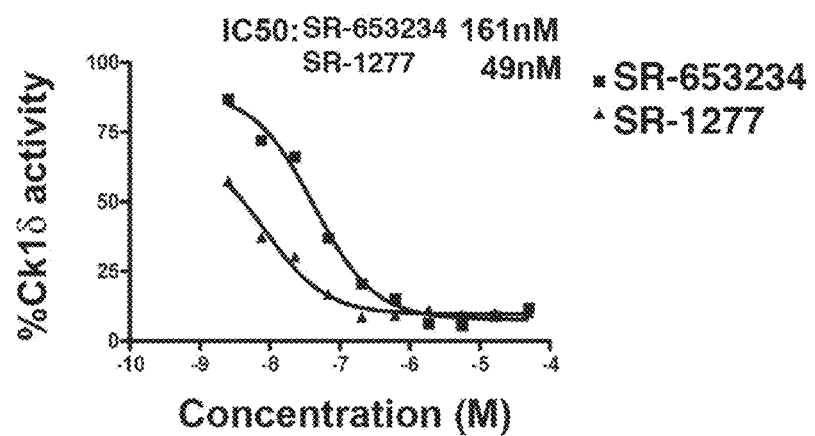
FIG. 2B is a graph of CK1δ activity versus concentration of SR-653234 or SR-1277.
Figure 2C:
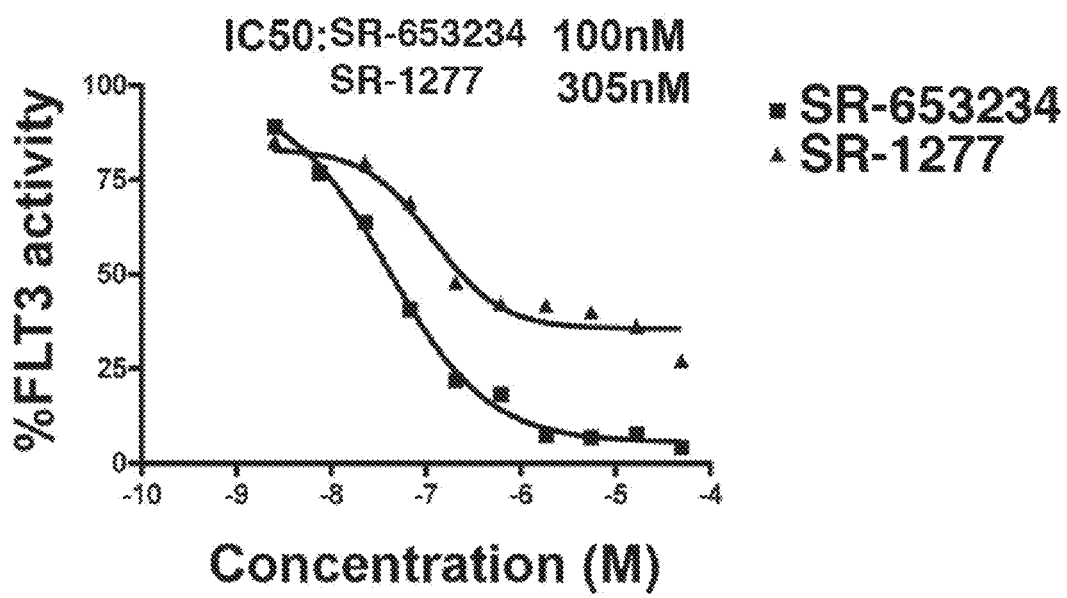
FIG. 2C is a graph of percent FLT3 activity versus concentration of SR-653234 or SR-1277.
Figure 2D:
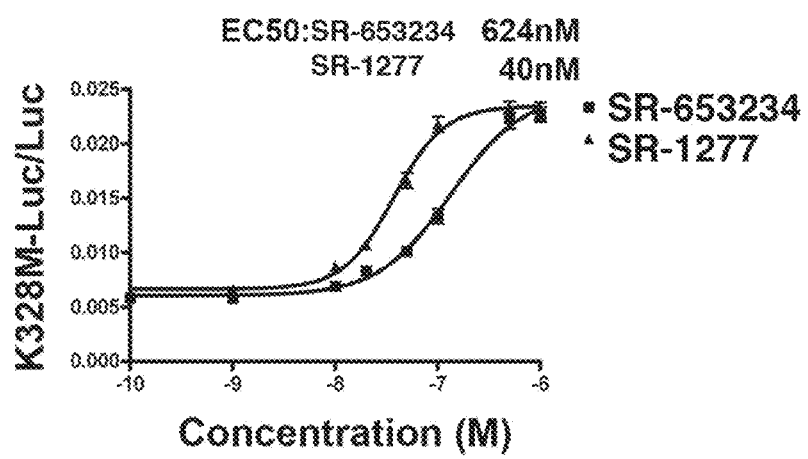
FIG. 2D is a graph of the steady-state level of K328M-Wee1-Luciferase (K328M-Wee1-Luc) divided by the Luciferase level (Luc) versus concentration of SR-653234 or SR-1277.

As used in the specification and the appended claims, the singular forms "a," "an" and "the" include plural referents unless the context clearly dictates otherwise.

The term "about" as used herein, when referring to a numerical value or range, allows for a degree of variability in the value or range, for example, within 10%, or within 5% of a stated value or of a stated limit of a range.

As used herein, "individual" (as in the subject of the treatment) means both mammals and non-mammals. Mammals include, for example, humans; non-human primates, e.g. apes and monkeys; and non-primates, e.g. dogs, cats, cattle, horses, sheep, and goats. Non-mammals include, for example, fish and birds.

The term "disease" or "disorder" or "malcondition" are used interchangeably, and are used to refer to diseases or conditions wherein a therapeutically beneficial effect can be achieved by inhibiting the degradation of Wee1, or by inhibiting casein kinase 1 (CK1), or by reducing cell proliferation, or by reducing amyloid beta 40 production, or a combination thereof.

The expression "effective amount", when used to describe therapy to an individual suffering from a disorder, refers to the amount of a compound of the invention that is effective to inhibit the degradation of Wee1 in the individual's tissues, or to inhibit casein kinase 1 (CK1), or to reduce cell proliferation, or to reduce amyloid beta 40 production, or a combination thereof, wherein such inhibition or other action occurs to an extent sufficient to produce a beneficial therapeutic effect.

"Substantially" as the term is used herein means completely or almost completely; for example, a composition that is "substantially free" of a component either has none of the component or contains such a trace amount that any relevant functional property of the composition is unaffected by the presence of the trace amount, or a compound is "substantially pure" is there are only negligible traces of impurities present.

"Treating" or "treatment" within the meaning herein refers to an alleviation of symptoms associated with a disorder or disease, or inhibition of further progression or worsening of those symptoms, or prevention or prophylaxis of the disease or disorder, or curing the disease or disorder. Similarly, as used herein, an "effective amount" or a "therapeutically effective amount" of a compound of the invention refers to an amount of the compound that alleviates, in whole or in part, symptoms associated with the disorder or condition, or halts or slows further progression or worsening of those symptoms, or prevents or provides prophylaxis for the disorder or condition. In particular, a "therapeutically effective amount" refers to an amount effective, at dosages and for periods of time necessary, to achieve the desired therapeutic result. A therapeutically effective amount is also one in which any toxic or detrimental effects of compounds of the invention are outweighed by the therapeutically beneficial effects.

By "chemically feasible" is meant a bonding arrangement or a compound where the generally understood rules of organic structure are not violated; for example a structure within a definition of a claim that would contain in certain situations a pentavalent carbon atom that would not exist in nature would be understood to not be within the claim. The structures disclosed herein, in all of their embodiments are intended to include only "chemically feasible" structures, and any recited structures that are not chemically feasible, for example in a structure shown with variable atoms or groups, are not intended to be disclosed or claimed herein.

When a substituent is specified to be an atom or atoms of specified identity, "or a bond", a configuration is referred to when the substituent is "a bond" that the groups that are immediately adjacent to the specified substituent are directly connected to each other in a chemically feasible bonding configuration.

All chiral, diastereomeric, racemic forms of a structure are intended, unless a particular stereochemistry or isomeric form is specifically indicated. Compounds used in the present invention can include enriched or resolved optical isomers at any or all asymmetric atoms as are apparent from the depictions, at any degree of enrichment. Both racemic and diastereomeric mixtures, as well as the individual optical isomers can be isolated or synthesized so as to be substantially free of their enantiomeric or diastereomeric partners, and these are all within the scope of the invention.

The inclusion of an isotopic form of one or more atoms in a molecule that is different from the naturally occurring isotopic distribution of the atom in nature is referred to as an "isotopically labeled form" of the molecule. All isotopic forms of atoms are included as options in the composition of any molecule, unless a specific isotopic form of an atom is indicated. For example, any hydrogen atom or set thereof in a molecule can be any of the isotopic forms of hydrogen, i.e., protium ($^1$H), deuterium ($^2$H), or tritium ($^3$H) in any combination. Similarly, any carbon atom or set thereof in a molecule can be any of the isotopic form of carbons, such as $^{11}$C, $^{12}$C, $^{13}$C, or $^{14}$C, or any nitrogen atom or set thereof in a molecule can be any of the isotopic forms of nitrogen, such as $^{13}$N, $^{14}$N or $^{15}$N. A molecule can include any combination of isotopic forms in the component atoms making up the molecule, the isotopic form of every atom forming the molecule being independently selected. In a multi-molecular sample of a compound, not every individual molecule necessarily has the same isotopic composition. For example, a sample of a compound can include molecules containing various different isotopic compositions, such as in a tritium or $^{14}C$ radiolabeled sample where only some fraction of the set of molecules making up the macroscopic sample contains a radioactive atom. It is also understood that many elements that are not artificially isotopically enriched themselves are mixtures of naturally occurring isotopic forms, such as $^{14}N$ and $^{15}N$, $^{32}S$ and $^{34}N$ and so forth. A molecule as recited herein is defined as including isotopic forms of all its constituent elements at each position in the molecule. As is well known in the art, isotopically labeled compounds can be prepared by the usual methods of chemical synthesis, except substituting an isotopically labeled precursor molecule. The isotopes, radiolabeled or stable, can be obtained by any method known in the art, such as generation by neutron absorption of a precursor nuclide in a nuclear reactor, by cyclotron reactions, or by isotopic separation such as by mass spectrometry. The isotopic forms are incorporated into precursors as required for use in any particular synthetic route. For example, $^{14}C$ and $^{3}H$ can be prepared using neutrons generated in a nuclear reactor. Following nuclear transformation, $^{14}C$ and $^{3}H$ are incorporated into precursor molecules, followed by further elaboration as needed.

In general, "substituted" refers to an organic group as defined herein in which one or more bonds to a hydrogen atom contained therein are replaced by one or more bonds to a non-hydrogen atom such as, but not limited to, a halogen (i.e., F, Cl, Br, and I); an oxygen atom in groups such as hydroxyl groups, alkoxy groups, aryloxy groups, aralkyloxy groups, oxo(carbonyl) groups, carboxyl groups including carboxylic acids, carboxylates, and carboxylate esters; a sulfur atom in groups such as thiol groups, alkyl and aryl sulfide groups, sulfoxide groups, sulfone groups, sulfonyl groups, and sulfonamide groups; a nitrogen atom in groups such as amines, hydroxylamines, nitriles, nitro groups, N-oxides, hydrazides, azides, and enamines; and other heteroatoms in various other groups. Non-limiting examples of substituents that can be bonded to a substituted carbon (or other) atom include F, Cl, Br, I, OR, OC(O)N(R)$_2$, CN, NO, NO$_2$, ONO$_2$, azido, CF$_3$, OCF$_3$, R, O (oxo), S (thiono), C(O), S(O), methylenedioxy, ethylenedioxy, N(R)$_2$, SR, SOR, SO$_2$R, SO$_2$N(R)$_2$, SO$_3$R, C(O)R, C(O)C(O)R, C(O)CH$_2$C(O)R, C(S)R, C(O)OR, OC(O)R, C(O)N(R)$_2$, OC(O)N(R)$_2$, C(S)N(R)$_2$, (CH$_2$)$_{0-2}$N(R)C(O)R, (CH$_2$)$_{0-2}$N(R)N(R)$_2$, N(R)N(R)C(O)R, N(R)N(R)C(O)OR, N(R)N(R)CON(R)$_2$, N(R)SO$_2$R, N(R)SO$_2$N(R)$_2$, N(R)C(O)OR, N(R)C(O)R, N(R)C(S)R, N(R)C(O)N(R)$_2$, N(R)C(S)N(R)$_2$, N(COR)COR, N(OR)R, C(=NH)N(R)$_2$, C(O)N(OR)R, or C(=NOR)R wherein R can be hydrogen or a carbon-based moiety, and wherein the carbon-based moiety can itself be further substituted.

When a group is said to be "each independently" chosen or selected "independently at each occurrence," each individual group designated by a variable (e.g., an "R" group or a "J" group) is independent of any other similarly designated groups in the structure and need not be the same as another such group selected from a list of options recited. For example, in a group such as —CR$_2$—, when each R is "independently" selected, the two R groups on the carbon atom need not be the same group. Similarly, if a ring, for example, is substituted with n number of J substituent groups, each J can be the same or different from other J groups within the overall list of optional groups at that position.

When a substituent is monovalent, such as, for example, F or Cl, it is bonded to the atom it is substituting by a single bond. When a substituent is more than monovalent, such as O, which is divalent, it can be bonded to the atom it is substituting by more than one bond, i.e., a divalent substituent is bonded by a double bond; for example, a C substituted with O forms a carbonyl group, C=O, which can also be written as "CO", "C(O)", or "C(=O)", wherein the C and the O are double bonded. When a carbon atom is substituted with a double-bonded oxygen (=O) group, the oxygen substituent is termed an "oxo" group. When a divalent substituent such as NR is double-bonded to a carbon atom, the resulting C(=NR) group is termed an "imino" group. When a divalent substituent such as S is double-bonded to a carbon atom, the results C(=S) group is termed a "thiocarbonyl" group.

Alternatively, a divalent substituent such as O, S, C(O), S(O), or S(O)$_2$ can be connected by two single bonds to two different carbon atoms. For example, O, a divalent substituent, can be bonded to each of two adjacent carbon atoms to provide an epoxide group, or the O can form a bridging ether group, termed an "oxy" group, between adjacent or non-adjacent carbon atoms, for example bridging the 1,4-carbons of a cyclohexyl group to form a [2.2.1]-oxabicyclo system. Further, any substituent can be bonded to a carbon or other atom by a linker, such as (CH$_2$)$_n$ or (CR$_2$)$_n$ wherein n is 1, 2, 3, or more, and each R is independently selected.

C(O) and S(O)$_2$ groups can be bound to one or two heteroatoms, such as nitrogen, rather than to a carbon atom. For example, when a C(O) group is bound to one carbon and one nitrogen atom, the resulting group is called an "amide" or "carboxamide." When a C(O) group is bound to two nitrogen atoms, the functional group is termed a "urea". When a S(O)$_2$ group is bound to one carbon and one nitrogen atom, the resulting unit is termed a "sulfonamide." When a S(O)$_2$ group is bound to two nitrogen atoms, the resulting unit is termed a "sulfamide."

Substituted alkyl, alkenyl, alkynyl, cycloalkyl, and cycloalkenyl groups as well as other substituted groups also include groups in which one or more bonds to a hydrogen atom are replaced by one or more bonds, including double or triple bonds, to a carbon atom, or to a heteroatom such as, but not limited to, oxygen in carbonyl (oxo), carboxyl, ester, amide, imide, urethane, and urea groups; and nitrogen in imines, hydroxyimines, oximes, hydrazones, amidines, guanidines, and nitriles.

Substituted ring groups such as substituted cycloalkyl, aryl, heterocyclyl and heteroaryl groups also include rings and fused ring systems in which a bond to a hydrogen atom is replaced with a bond to a carbon atom. Therefore, substituted cycloalkyl, aryl, heterocyclyl and heteroaryl groups can also be substituted with alkyl, alkenyl, and alkynyl groups as defined herein.

By a "ring system" as the term is used herein is meant a moiety including one, two, three or more rings, which can be substituted with non-ring groups or with other ring systems, or both, which can be fully saturated, partially unsaturated, fully unsaturated, or aromatic, and when the ring system includes more than a single ring, the rings can be fused, bridging, or spirocyclic. By "spirocyclic" is meant the class of structures wherein two rings are fused at a single tetrahedral carbon atom, as is well known in the art.

As to any of the groups described herein, which contain one or more substituents, it is understood, of course, that such groups do not contain any substitution or substitution patterns which are sterically impractical and/or synthetically nonfeasible. In addition, the compounds of this disclosed subject matter include all stereochemical isomers arising from the substitution of these compounds.

Selected substituents within the compounds described herein are present to a recursive degree. In this context, "recursive substituent" means that a substituent may recite another instance of itself. Because of the recursive nature of such substituents, theoretically, a large number may be present in any given claim. One of ordinary skill in the art of medicinal chemistry and organic chemistry understands that the total number of such substituents is reasonably limited by the desired properties of the compound intended. Such properties include, by of example and not limitation, physical properties such as molecular weight, solubility or log P, application properties such as activity against the intended target, and practical properties such as ease of synthesis.

Recursive substituents are an intended aspect of the disclosed subject matter. One of ordinary skill in the art of medicinal and organic chemistry understands the versatility of such substituents. To the degree that recursive substituents are present in a claim of the disclosed subject matter, the total number should be determined as set forth above.

Alkyl groups include straight chain and branched alkyl groups and cycloalkyl groups having from 1 to about 20 carbon atoms, and typically from 1 to 12 carbons or, in some embodiments, from 1 to 8 carbon atoms. Examples of straight chain alkyl groups include those with from 1 to 8 carbon atoms such as methyl, ethyl, n-propyl, n-butyl, n-pentyl, n-hexyl, n-heptyl, and n-octyl groups. Examples of branched alkyl groups include, but are not limited to, isopropyl, iso-butyl, sec-butyl, t-butyl, neopentyl, isopentyl, and 2,2-dimethylpropyl groups. Representative substituted alkyl groups can be substituted one or more times with any of the groups listed above, for example, amino, hydroxy, cyano, carboxy, nitro, thio, alkoxy, and halogen groups.

Cycloalkyl groups are cyclic alkyl groups such as, but not limited to, cyclopropyl, cyclobutyl, cyclopentyl, cyclohexyl, cycloheptyl, and cyclooctyl groups. In some embodiments, the cycloalkyl group can have 3 to about 8-12 ring members, whereas in other embodiments the number of ring carbon atoms range from 3 to 4, 5, 6, or 7. Cycloalkyl groups further include polycyclic cycloalkyl groups such as, but not limited to, norbornyl, adamantyl, bornyl, camphenyl, isocamphenyl, and carenyl groups, and fused rings such as, but not limited to, decalinyl, and the like. Cycloalkyl groups also include rings that are substituted with straight or branched chain alkyl groups as defined above. Representative substituted cycloalkyl groups can be mono-substituted or substituted more than once, such as, but not limited to, 2,2-, 2,3-, 2,4-2,5- or 2,6-disubstituted cyclohexyl groups or mono-, di- or tri-substituted norbornyl or cycloheptyl groups, which can be substituted with, for example, amino, hydroxy, cyano, carboxy, nitro, thio, alkoxy, and halogen groups. The term "cycloalkenyl" alone or in combination denotes a cyclic alkenyl group.

The terms "carbocyclic," "carbocyclyl," and "carbocycle" denote a ring structure wherein the atoms of the ring are carbon, such as a cycloalkyl group or an aryl group. In some embodiments, the carbocycle has 3 to 8 ring members, whereas in other embodiments the number of ring carbon atoms is 4, 5, 6, or 7. Unless specifically indicated to the contrary, the carbocyclic ring can be substituted with as many as N-1 substituents wherein N is the size of the carbocyclic ring with, for example, alkyl, alkenyl, alkynyl, amino, aryl, hydroxy, cyano, carboxy, heteroaryl, heterocyclyl, nitro, thio, alkoxy, and halogen groups, or other groups as are listed above. A carbocyclyl ring can be a cycloalkyl ring, a cycloalkenyl ring, or an aryl ring. A carbocyclyl can be monocyclic or polycyclic, and if polycyclic each ring can be independently be a cycloalkyl ring, a cycloalkenyl ring, or an aryl ring.

(Cycloalkyl)alkyl groups, also denoted cycloalkylalkyl, are alkyl groups as defined above in which a hydrogen or carbon bond of the alkyl group is replaced with a bond to a cycloalkyl group as defined above.

Alkenyl groups include straight and branched chain and cyclic alkyl groups as defined above, except that at least one double bond exists between two carbon atoms. Thus, alkenyl groups have from 2 to about 20 carbon atoms, and typically from 2 to 12 carbons or, in some embodiments, from 2 to 8 carbon atoms. Examples include, but are not limited to vinyl, $-CH=CH(CH_3)$, $-CH=C(CH_3)_2$, $-C(CH_3)=CH_2$, $-C(CH_3)=CH(CH_3)$, $-C(CH_2CH_3)=CH_2$, cyclohexenyl, cyclopentenyl, cyclohexadienyl, butadienyl, pentadienyl, and hexadienyl among others.

Cycloalkenyl groups include cycloalkyl groups having at least one double bond between 2 carbons. Thus for example, cycloalkenyl groups include but are not limited to cyclohexenyl, cyclopentenyl, and cyclohexadienyl groups. Cycloalkenyl groups can have from 3 to about 8-12 ring members, whereas in other embodiments the number of ring carbon atoms range from 3 to 5, 6, or 7. Cycloalkyl groups further include polycyclic cycloalkyl groups such as, but not limited to, norbornyl, adamantyl, bornyl, camphenyl, isocamphenyl, and carenyl groups, and fused rings such as, but not limited to, decalinyl, and the like, provided they include at least one double bond within a ring. Cycloalkenyl groups also include rings that are substituted with straight or branched chain alkyl groups as defined above.

(Cycloalkenyl)alkyl groups are alkyl groups as defined above in which a hydrogen or carbon bond of the alkyl group is replaced with a bond to a cycloalkenyl group as defined above.

Alkynyl groups include straight and branched chain alkyl groups, except that at least one triple bond exists between two carbon atoms. Thus, alkynyl groups have from 2 to about 20 carbon atoms, and typically from 2 to 12 carbons or, in some embodiments, from 2 to 8 carbon atoms. Examples include, but are not limited to $-C\equiv CH$, $-C\equiv C(CH_3)$, $-C\equiv C(CH_2CH_3)$, $-CH_2C\equiv CH$, $-CH_2C\equiv C(CH_3)$, and $-CH_2C\equiv C(CH_2CH_3)$ among others.

The term "heteroalkyl" by itself or in combination with another term means, unless otherwise stated, a stable straight or branched chain alkyl group consisting of the stated number of carbon atoms and one or two heteroatoms selected from the group consisting of O, N, and S, and wherein the nitrogen and sulfur atoms may be optionally oxidized and the nitrogen heteroatom may be optionally quaternized. The heteroatom(s) may be placed at any position of the heteroalkyl group, including between the rest of the heteroalkyl group and the fragment to which it is attached, as well as attached to the most distal carbon atom in the heteroalkyl group. Examples include: $-O-CH_2-CH_2-CH_3$, $-CH_2-CH_2CH_2-OH$, $-CH_2-CH_2-NH-CH_3$, $-CH_2-S-CH_2-CH_3$, $-CH_2CH_2-S(=O)-CH_3$, and $-CH_2CH_2-O-CH_2CH_2-O-CH_3$. Up to two heteroatoms may be consecutive, such as, for example, $-CH_2-NH-OCH_3$, or $CH_2-CH_2-S-S-CH_3$.

A "cycloheteroalkyl" ring is a cycloalkyl ring containing at least one heteroatom. A cycloheteroalkyl ring can also be termed a "heterocyclyl," described below.

The term "heteroalkenyl" by itself or in combination with another term means, unless otherwise stated, a stable straight or branched chain monounsaturated or di-unsaturated hydrocarbon group consisting of the stated number of carbon atoms and one or two heteroatoms selected from the group consisting of O, N, and S, and wherein the nitrogen and sulfur atoms may optionally be oxidized and the nitrogen heteroatom may optionally be quaternized. Up to two heteroatoms may be placed consecutively. Examples include —CH═CH—O—CH₃, —CH═CH—CH₂—OH, —CH₂—CH═N—OCH₃, —CH═CH—N(CH₃)—CH₃, —CH₂—CH═CH—CH₂—SH, and and —CH═CH—O—CH₂CH₂—O—CH₃.

Aryl groups are cyclic aromatic hydrocarbons that do not contain heteroatoms in the ring. Thus aryl groups include, but are not limited to, phenyl, azulenyl, heptalenyl, biphenyl, indacenyl, fluorenyl, phenanthrenyl, triphenylenyl, pyrenyl, naphthacenyl, chrysenyl, biphenylenyl, anthracenyl, and naphthyl groups. In some embodiments, aryl groups contain about 6 to about 14 carbons in the ring portions of the groups. Aryl groups can be unsubstituted or substituted, as defined above. Representative substituted aryl groups can be mono-substituted or substituted more than once, such as, but not limited to, 2-, 3-, 4-, 5-, or 6-substituted phenyl or 2-8 substituted naphthyl groups, which can be substituted with carbon or non-carbon groups such as those listed above.

Aralkyl groups are alkyl groups as defined above in which a hydrogen or carbon bond of an alkyl group is replaced with a bond to an aryl group as defined above. Representative aralkyl groups include benzyl and phenylethyl groups and fused (cycloalkylaryl)alkyl groups such as 4-ethyl-indanyl. Aralkenyl group are alkenyl groups as defined above in which a hydrogen or carbon bond of an alkyl group is replaced with a bond to an aryl group as defined above.

Heterocyclyl groups or the term "heterocyclyl" includes aromatic and non-aromatic ring compounds containing 3 or more ring members, of which, one or more is a heteroatom such as, but not limited to, N, O, and S. Thus a heterocyclyl can be a cycloheteroalkyl, or a heteroaryl, or if polycyclic, any combination thereof. In some embodiments, heterocyclyl groups include 3 to about 20 ring members, whereas other such groups have 3 to about 15 ring members. A heterocyclyl group designated as a C₂-heterocyclyl can be a 5-ring with two carbon atoms and three heteroatoms, a 6-ring with two carbon atoms and four heteroatoms and so forth. Likewise a C₄-heterocyclyl can be a 5-ring with one heteroatom, a 6-ring with two heteroatoms, and so forth. The number of carbon atoms plus the number of heteroatoms sums up to equal the total number of ring atoms. A heterocyclyl ring can also include one or more double bonds. A heteroaryl ring is an embodiment of a heterocyclyl group. The phrase "heterocyclyl group" includes fused ring species including those that include fused aromatic and non-aromatic groups. For example, a dioxolanyl ring and a benzdioxolanyl ring system (methylenedioxyphenyl ring system) are both heterocyclyl groups within the meaning herein. The phrase also includes polycyclic ring systems containing a heteroatom such as, but not limited to, quinuclidyl. Heterocyclyl groups can be unsubstituted, or can be substituted as discussed above. Heterocyclyl groups include, but are not limited to, pyrrolidinyl, piperidinyl, piperazinyl, morpholinyl, pyrrolyl, pyrazolyl, triazolyl, tetrazolyl, oxazolyl, isoxazolyl, thiazolyl, pyridinyl, thiophenyl, benzothiophenyl, benzofuranyl, dihydrobenzofuranyl, indolyl, dihydroindolyl, azaindolyl, indazolyl, benzimidazolyl, azabenzimidazolyl, benzoxazolyl, benzothiazolyl, benzothiadiazolyl, imidazopyridinyl, isoxazolopyridinyl, thianaphthalenyl, purinyl, xanthinyl, adeninyl, guaninyl, quinolinyl, isoquinolinyl, tetrahydroquinolinyl, quinoxalinyl, and quinazolinyl groups. Representative substituted heterocyclyl groups can be mono-substituted or substituted more than once, such as, but not limited to, piperidinyl or quinolinyl groups, which are 2-, 3-, 4-, 5-, or 6-substituted, or disubstituted with groups such as those listed above.

Heteroaryl groups are aromatic ring compounds containing 5 or more ring members, of which, one or more is a heteroatom such as, but not limited to, N, O, and S; for instance, heteroaryl rings can have 5 to about 8-12 ring members. A heteroaryl group is a variety of a heterocyclyl group that possesses an aromatic electronic structure. A heteroaryl group designated as a C₂-heteroaryl can be a 5-ring with two carbon atoms and three heteroatoms, a 6-ring with two carbon atoms and four heteroatoms and so forth. Likewise a C₄-heteroaryl can be a 5-ring with one heteroatom, a 6-ring with two heteroatoms, and so forth. The number of carbon atoms plus the number of heteroatoms sums up to equal the total number of ring atoms. Heteroaryl groups include, but are not limited to, groups such as pyrrolyl, pyrazolyl, triazolyl, tetrazolyl, oxazolyl, isoxazolyl, thiazolyl, pyridinyl, thiophenyl, benzothiophenyl, benzofuranyl, indolyl, azaindolyl, indazolyl, benzimidazolyl, azabenzimidazolyl, benzoxazolyl, benzothiazolyl, benzothiadiazolyl, imidazopyridinyl, isoxazolopyridinyl, thianaphthalenyl, purinyl, xanthinyl, adeninyl, guaninyl, quinolinyl, isoquinolinyl, tetrahydroquinolinyl, quinoxalinyl, and quinazolinyl groups. Heteroaryl groups can be unsubstituted, or can be substituted with groups as is discussed above. Representative substituted heteroaryl groups can be substituted one or more times with groups such as those listed above.

Additional examples of aryl and heteroaryl groups include but are not limited to phenyl, biphenyl, indenyl, naphthyl (1-naphthyl, 2-naphthyl), N-hydroxytetrazolyl, N-hydroxytriazolyl, N-hydroxyimidazolyl, anthracenyl (1-anthracenyl, 2-anthracenyl, 3-anthracenyl), thiophenyl (2-thienyl, 3-thienyl), furyl (2-furyl, 3-furyl), indolyl, oxadiazolyl, isoxazolyl, quinazolinyl, fluorenyl, xanthenyl, isoindanyl, benzhydryl, acridinyl, thiazolyl, pyrrolyl (2-pyrrolyl), pyrazolyl (3-pyrazolyl), imidazolyl (1-imidazolyl, 2-imidazolyl, 4-imidazolyl, 5-imidazolyl), triazolyl (1,2,3-triazol-1-yl, 1,2,3-triazol-2-yl 1,2,3-triazol-4-yl, 1,2,4-triazol-3-yl), oxazolyl (2-oxazolyl, 4-oxazolyl, 5-oxazolyl), thiazolyl (2-thiazolyl, 4-thiazolyl, 5-thiazolyl), pyridyl (2-pyridyl, 3-pyridyl, 4-pyridyl), pyrimidinyl (2-pyrimidinyl, 4-pyrimidinyl, 5-pyrimidinyl, 6-pyrimidinyl), pyrazinyl, pyridazinyl (3-pyridazinyl, 4-pyridazinyl, 5-pyridazinyl), quinolyl (2-quinolyl, 3-quinolyl, 4-quinolyl, 5-quinolyl, 6-quinolyl, 7-quinolyl, 8-quinolyl), isoquinolyl (1-isoquinolyl, 3-isoquinolyl, 4-isoquinolyl, 5-isoquinolyl, 6-isoquinolyl, 7-isoquinolyl, 8-isoquinolyl), benzo[b]furanyl (2-benzo[b]furanyl, 3-benzo[b]furanyl, 4-benzo[b]furanyl, 5-benzo[b]furanyl, 6-benzo[b]furanyl, 7-benzo[b]furanyl), 2,3-dihydro-benzo[b]furanyl (2-(2,3-dihydro-benzo[b]furanyl), 3-(2,3-dihydro-benzo[b]furanyl), 4-(2,3-dihydro-benzo[b]furanyl), 5-(2,3-dihydro-benzo[b]furanyl), 6-(2,3-dihydro-benzo[b]furanyl), 7-(2,3-dihydro-benzo[b]furanyl), benzo[b]thiophenyl (2-benzo[b]thiophenyl, 3-benzo[b]thiophenyl, 4-benzo[b]thiophenyl, 5-benzo[b]thiophenyl, 6-benzo[b]thiophenyl, 7-benzo[b]thiophenyl), 2,3-dihydro-benzo[b]thiophenyl, (2-(2,3-dihydro-benzo[b]thiophenyl), 3-(2,3-dihydro-benzo[b]thiophenyl), 4-(2,3-dihydro-benzo[b]thiophenyl), 5-(2,3-dihydro-benzo[b]thiophenyl), 6-(2,3-dihydro-benzo[b]thiophenyl), 7-(2,3-dihydro-benzo[b]thiophenyl), indolyl (1-indolyl, 2-indolyl, 3-indolyl, 4-indolyl, 5-indolyl, 6-indolyl, 7-indolyl), indazole (1-indazolyl, 3-indazolyl, 4-indazolyl, 5-indazolyl, 6-indazolyl, 7-indazolyl), benzimidazolyl (1-benzimidazolyl, 2-benzimidazolyl, 4-benzimidazolyl, 5-benzimidazolyl, 6-benzimidazolyl, 7-benzimidazolyl, 8-benzimidazolyl), benzoxazolyl (1-benzoxazolyl, 2-benzoxazolyl), benzothiazolyl (1-benzothiazolyl, 2-benzothiazolyl, 4-benzothiazolyl, 5-benzothiazolyl, 6-benzothiazolyl, 7-benzothiazolyl), carbazolyl (1-carbazolyl, 2-carbazolyl, 3-carbazolyl, 4-carbazolyl), 5H-dibenzMazepine (5H-dibenz[b,f]azepin-1-yl, 5H-dibenz[b,f]azepine-2-yl, 5H-dibenz[b,f]azepine-3-yl, 5H-dibenz[b,f]azepine-4-yl, 5H-dibenz[b,f]azepine-5-yl), 10,11-dihydro-5H-dibenz[b,f]azepine (10,11-dihydro-5H-dibenz[b,f]azepine-1-yl, 10,11-dihydro-5H-dibenz[b,f]azepine-2-yl, 10,11-dihydro-5H-dibenz UM azepine-3-yl, 10,11-dihydro-5H-dibenz[b,f]azepine-4-yl, 10,11-dihydro-5H-dibenz[b,f]azepine-5-yl), and the like.

Heterocyclylalkyl groups are alkyl groups as defined above in which a hydrogen or carbon bond of an alkyl group as defined above is replaced with a bond to a heterocyclyl group as defined above. Representative heterocyclyl alkyl groups include, but are not limited to, furan-2-yl methyl, furan-3-yl methyl, pyridine-3-yl methyl, tetrahydrofuran-2-yl ethyl, and indol-2-yl propyl.

Heteroarylalkyl groups are alkyl groups as defined above in which a hydrogen or carbon bond of an alkyl group is replaced with a bond to a heteroaryl group as defined above.

The term "alkoxy" refers to an oxygen atom connected to an alkyl group, including a cycloalkyl group, as are defined above. Examples of linear alkoxy groups include but are not limited to methoxy, ethoxy, propoxy, butoxy, pentyloxy, hexyloxy, and the like. Examples of branched alkoxy include but are not limited to isopropoxy, sec-butoxy, tert-butoxy, isopentyloxy, isohexyloxy, and the like. Examples of cyclic alkoxy include but are not limited to cyclopropyloxy, cyclobutyloxy, cyclopentyloxy, cyclohexyloxy, and the like. An alkoxy group can include one to about 12-20 carbon atoms bonded to the oxygen atom, and can further include double or triple bonds, and can also include heteroatoms. For example, an allyloxy group is an alkoxy group within the meaning herein. A methoxyethoxy group is also an alkoxy group within the meaning herein, as is a methylenedioxy group in a context where two adjacent atoms of a structures are substituted therewith.

The terms "halo" or "halogen" or "halide" by themselves or as part of another substituent mean, unless otherwise stated, a fluorine, chlorine, bromine, or iodine atom, preferably, fluorine, chlorine, or bromine.

A "haloalkyl" group includes mono-halo alkyl groups, poly-halo alkyl groups wherein all halo atoms can be the same or different, and per-halo alkyl groups, wherein all hydrogen atoms are replaced by halogen atoms, such as fluoro. Examples of haloalkyl include trifluoromethyl, 1,1-dichloroethyl, 1,2-dichloroethyl, 1,3-dibromo-3,3-difluoropropyl, perfluorobutyl, and the like.

A "haloalkoxy" group includes mono-halo alkoxy groups, poly-halo alkoxy groups wherein all halo atoms can be the same or different, and per-halo alkoxy groups, wherein all hydrogen atoms are replaced by halogen atoms, such as fluoro. Examples of halo alkoxy include trifluoromethoxy, 1,1-dichloroethoxy, 1,2-dichloroethoxy, 1,3-dibromo-3,3-difluoropropoxy, perfluorobutoxy, and the like.

The term "$(C_x$-$C_y)$perfluoroalkyl," wherein x<y, means an alkyl group with a minimum of x carbon atoms and a maximum of y carbon atoms, wherein all hydrogen atoms are replaced by fluorine atoms. Preferred is —$(C_1$-$C_6)$ perfluoroalkyl, more preferred is —$(C_1$-$C_3)$perfluoroalkyl, most preferred is —$CF_3$.

The term "$(C_x$-$C_y)$perfluoroalkylene," wherein x<y, means an alkyl group with a minimum of x carbon atoms and a maximum of y carbon atoms, wherein all hydrogen atoms are replaced by fluorine atoms. Preferred is —$(C_1$-$C_6)$perfluoroalkylene, more preferred is —$(C_1$-$C_3)$perfluoroalkylene, most preferred is —$CF_2$—.

The terms "aryloxy" and "arylalkoxy" refer to, respectively, an aryl group bonded to an oxygen atom and an aralkyl group bonded to the oxygen atom at the alkyl moiety. Examples include but are not limited to phenoxy, naphthyloxy, and benzyloxy.

An "acyl" group as the term is used herein refers to a group containing a carbonyl moiety wherein the group is bonded via the carbonyl carbon atom. The carbonyl carbon atom is also bonded to another carbon atom, which can be part of an alkyl, aryl, aralkyl cycloalkyl, cycloalkylalkyl, heterocyclyl, heterocyclylalkyl, heteroaryl, heteroarylalkyl group or the like. In the special case wherein the carbonyl carbon atom is bonded to a hydrogen, the group is a "formyl" group, an acyl group as the term is defined herein. An acyl group can include 0 to about 12-20 additional carbon atoms bonded to the carbonyl group. An acyl group can include double or triple bonds within the meaning herein. An acryloyl group is an example of an acyl group. An acyl group can also include heteroatoms within the meaning here. A nicotinoyl group (pyridyl-3-carbonyl) group is an example of an acyl group within the meaning herein. Other examples include acetyl, benzoyl, phenylacetyl, pyridylacetyl, cinnamoyl, and acryloyl groups and the like. When the group containing the carbon atom that is bonded to the carbonyl carbon atom contains a halogen, the group is termed a "haloacyl" group. An example is a trifluoroacetyl group.

The term "amine" includes primary, secondary, and tertiary amines having, e.g., the formula N(group)$_3$ wherein each group can independently be H or non-H, such as alkyl, aryl, and the like Amines include but are not limited to R—$NH_2$, for example, alkylamines, arylamines, alkylarylamines; $R_2NH$ wherein each R is independently selected, such as dialkylamines, diarylamines, aralkylamines, heterocyclylamines and the like; and $R_3N$ wherein each R is independently selected, such as trialkylamines, dialkylarylamines, alkyldiarylamines, triarylamines, and the like. The term "amine" also includes ammonium ions as used herein.

An "amino" group is a substituent of the form —$NH_2$, —NHR, —$NR_2$, —$NR_3^+$, wherein each R is independently selected, and protonated forms of each, except for —$NR_3^+$, which cannot be protonated. Accordingly, any compound substituted with an amino group can be viewed as an amine. An "amino group" within the meaning herein can be a primary, secondary, tertiary or quaternary amino group. An "alkylamino" group includes a monoalkylamino, dialkylamino, and trialkylamino group.

An "ammonium" ion includes the unsubstituted ammonium ion $NH_4^+$, but unless otherwise specified, it also includes any protonated or quaternarized forms of amines. Thus, trimethylammonium hydrochloride and tetramethylammonium chloride are both ammonium ions, and amines, within the meaning herein.

The term "amide" (or "amido") includes C- and N-amide groups, i.e., —C(O)$NR_2$, and —NRC(O)R groups, respectively. Amide groups therefore include but are not limited to primary carboxamide groups (—C(O)$NH_2$) and formamide groups (—NHC(O)H). A "carboxamido" group is a group of the formula C(O)NR$_2$, wherein R can be H, alkyl, aryl, etc.

The term "azido" refers to an N$_3$ group. An "azide" can be an organic azide or can be a salt of the azide (N$_3^-$) anion. The term "nitro" refers to an NO$_2$ group bonded to an organic moiety. The term "nitroso" refers to an NO group bonded to an organic moiety. The term nitrate refers to an ONO$_2$ group bonded to an organic moiety or to a salt of the nitrate (NO$_3^-$) anion.

The term "urethane" ("carbamoyl" or "carbamyl") includes N- and O-urethane groups, i.e., —NRC(O)OR and OC(O)NR$_2$ groups, respectively.

The term "sulfonamide" (or "sulfonamido") includes S- and N-sulfonamide groups, i.e., —SO$_2$NR$_2$ and NRSO$_2$R groups, respectively. Sulfonamide groups therefore include but are not limited to sulfamoyl groups (—SO$_2$NH$_2$). An organosulfur structure represented by the formula —S(O)(NR)— is understood to refer to a sulfoximine, wherein both the oxygen and the nitrogen atoms are bonded to the sulfur atom, which is also bonded to two carbon atoms.

The term "amidine" or "amidino" includes groups of the formula —C(NR)NR$_2$. Typically, an amidino group is —C(NH)NH$_2$.

The term "guanidine" or "guanidino" includes groups of the formula —NRC(NR)NR$_2$. Typically, a guanidino group is —NHC(NH)NH$_2$.

A "salt" as is well known in the art includes an organic compound such as a carboxylic acid, a sulfonic acid, or an amine, in ionic form, in combination with a counterion. For example, acids in their anionic form can form salts with cations such as metal cations, for example sodium, potassium, and the like; with ammonium salts such as NH$_4^+$ or the cations of various amines, including tetraalkyl ammonium salts such as tetramethylammonium, or other cations such as trimethylsulfonium, and the like. A "pharmaceutically acceptable" or "pharmacologically acceptable" salt is a salt formed from an ion that has been approved for human consumption and is generally non-toxic, such as a chloride salt or a sodium salt. A "zwitterion" is an internal salt such as can be formed in a molecule that has at least two ionizable groups, one forming an anion and the other a cation, which serve to balance each other. For example, amino acids such as glycine can exist in a zwitterionic form. A "zwitterion" is a salt within the meaning herein. The compounds of the present invention may take the form of salts. The term "salts" embraces addition salts of free acids or free bases which are compounds of the invention. Salts can be "pharmaceutically-acceptable salts." The term "pharmaceutically-acceptable salt" refers to salts which possess toxicity profiles within a range that affords utility in pharmaceutical applications. Pharmaceutically unacceptable salts may nonetheless possess properties such as high crystallinity, which have utility in the practice of the present invention, such as for example utility in process of synthesis, purification or formulation of compounds of the invention.

Suitable pharmaceutically-acceptable acid addition salts may be prepared from an inorganic acid or from an organic acid. Examples of inorganic acids include hydrochloric, hydrobromic, hydriodic, nitric, carbonic, sulfuric, and phosphoric acids. Appropriate organic acids may be selected from aliphatic, cycloaliphatic, aromatic, araliphatic, heterocyclic, carboxylic and sulfonic classes of organic acids, examples of which include formic, acetic, propionic, succinic, glycolic, gluconic, lactic, malic, tartaric, citric, ascorbic, glucuronic, maleic, fumaric, pyruvic, aspartic, glutamic, benzoic, anthranilic, 4-hydroxybenzoic, phenylacetic, mandelic, embonic (pamoic), methanesulfonic, ethanesulfonic, benzenesulfonic, pantothenic, trifluoromethanesulfonic, 2-hydroxyethanesulfonic, p-toluenesulfonic, sulfanilic, cyclohexylaminosulfonic, stearic, alginic, β-hydroxybutyric, salicylic, galactaric and galacturonic acid. Examples of pharmaceutically unacceptable acid addition salts include, for example, perchlorates and tetrafluoroborates.

Suitable pharmaceutically acceptable base addition salts of compounds of the invention include, for example, metallic salts including alkali metal, alkaline earth metal and transition metal salts such as, for example, calcium, magnesium, potassium, sodium and zinc salts. Pharmaceutically acceptable base addition salts also include organic salts made from basic amines such as, for example, N,N'-dibenzylethylenediamine, chloroprocaine, choline, diethanolamine, ethylenediamine, meglumine (N-methylglucamine) and procaine. Examples of pharmaceutically unacceptable base addition salts include lithium salts and cyanate salts. Although pharmaceutically unacceptable salts are not generally useful as medicaments, such salts may be useful, for example as intermediates in the synthesis of Formula (I) compounds, for example in their purification by recrystallization. All of these salts may be prepared by conventional means from the corresponding compound according to Formula (I) by reacting, for example, the appropriate acid or base with the compound according to Formula (I). The term "pharmaceutically acceptable salts" refers to nontoxic inorganic or organic acid and/or base addition salts, see, for example, Lit et al., Salt Selection for Basic Drugs (1986), *Int J. Pharm.*, 33, 201-217, incorporated by reference herein.

A "hydrate" is a compound that exists in a composition with water molecules. The composition can include water in stoichiometric quantities, such as a monohydrate or a dihydrate, or can include water in random amounts. As the term is used herein a "hydrate" refers to a solid form, i.e., a compound in water solution, while it may be hydrated, is not a hydrate as the term is used herein.

A "solvate" is a similar composition except that a solvent other that water replaces the water. For example, methanol or ethanol can form an "alcoholate", which can again be stoichiometic or non-stoichiometric. As the term is used herein a "solvate" refers to a solid form, i.e., a compound in solution in a solvent, while it may be solvated, is not a solvate as the term is used herein.

A "prodrug" as is well known in the art is a substance that can be administered to a patient where the substance is converted in vivo by the action of biochemicals within the patient's body, such as enzymes, to the active pharmaceutical ingredient. Examples of prodrugs include esters of carboxylic acid groups, which can be hydrolyzed by endogenous esterases as are found in the bloodstream of humans and other mammals. Conventional procedures for the selection and preparation of suitable prodrug derivatives are described, for example, in "Design of Prodrugs", ed. H. Bundgaard, Elsevier, 1985.

In addition, where features or aspects of the invention are described in terms of Markush groups, those skilled in the art will recognize that the invention is also thereby described in terms of any individual member or subgroup of members of the Markush group. For example, if X is described as selected from the group consisting of bromine, chlorine, and iodine, claims for X being bromine and claims for X being bromine and chlorine are fully described. Moreover, where features or aspects of the invention are described in terms of Markush groups, those skilled in the art will recognize that the invention is also thereby described in terms of any combination of individual members or subgroups of members of Markush groups. Thus, for example, if X is described as selected from the group consisting of bromine, chlorine, and iodine, and Y is described as selected from the group consisting of methyl, ethyl, and propyl, claims for X being bromine and Y being methyl are fully described.

In various embodiments, the compound or set of compounds, such as are used in the inventive methods, can be any one of any of the combinations and/or sub-combinations of the above-listed embodiments.

The present invention further embraces isolated compounds according to formula (I). The expression "isolated compound" refers to a preparation of a compound of formula (I), or a mixture of compounds according to formula (I), wherein the isolated compound has been separated from the reagents used, and/or byproducts formed, in the synthesis of the compound or compounds. "Isolated" does not mean that the preparation is technically pure (homogeneous), but it is sufficiently pure to compound in a form in which it can be used therapeutically. Preferably an "isolated compound" refers to a preparation of a compound of formula (I) or a mixture of compounds according to formula (I), which contains the named compound or mixture of compounds according to formula (I) in an amount of at least 10 percent by weight of the total weight. Preferably the preparation contains the named compound or mixture of compounds in an amount of at least 50 percent by weight of the total weight; more preferably at least 80 percent by weight of the total weight; and most preferably at least 90 percent, at least 95 percent or at least 98 percent by weight of the total weight of the preparation.

The compounds of the invention and intermediates may be isolated from their reaction mixtures and purified by standard techniques such as filtration, liquid-liquid extraction, solid phase extraction, distillation, recrystallization or chromatography, including flash column chromatography, or HPLC.

Tautomerism

Within the present invention it is to be understood that a compound of the formula (I) or a salt thereof may exhibit the phenomenon of tautomerism whereby two chemical compounds that are capable of facile interconversion by exchanging a hydrogen atom between two atoms, to either of which it forms a covalent bond. Since the tautomeric compounds exist in mobile equilibrium with each other they may be regarded as different isomeric forms of the same compound. It is to be understood that the formulae drawings within this specification can represent only one of the possible tautomeric forms. However, it is also to be understood that the invention encompasses any tautomeric form, and is not to be limited merely to any one tautomeric form utilized within the formulae drawings. The formulae drawings within this specification can represent only one of the possible tautomeric forms and it is to be understood that the specification encompasses all possible tautomeric forms of the compounds drawn not just those forms which it has been convenient to show graphically herein. For example, tautomerism may be exhibited by a pyrazolyl group bonded as indicated by the wavy line. While both substituents would be termed a 3-methyl-4-pyrazolyl group, it is evident that a different nitrogen atom bears the hydrogen atom in each structure.

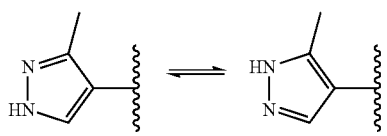

Such tautomerism can also occur with substituted pyrazoles such as 3-methyl, 5-methyl, or 3,5-dimethylpyrazoles, and the like. Another example of tautomerism is amido-imido (lactam-lactim when cyclic) tautomerism, such as is seen in heterocyclic compounds bearing a ring oxygen atom adjacent to a ring nitrogen atom. For example, the equilibrium:

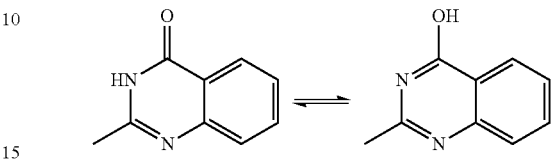

is an example of tautomerism. Accordingly, a structure depicted herein as one tautomer is intended to also include the other tautomer.

Optical Isomerism

It will be understood that, when compounds of the present invention contain one or more chiral centers, the compounds may exist in, and may be isolated as pure enantiomeric or diastereomeric forms or as racemic mixtures. The present invention therefore includes any possible enantiomers, diastereomers, racemates or mixtures thereof of the compounds of the invention.

The isomers resulting from the presence of a chiral center include a pair of non-superimposable isomers that are called "enantiomers." Single enantiomers of a pure compound are optically active, i.e., they are capable of rotating the plane of plane polarized light. Single enantiomers are designated according to the Cahn-Ingold-Prelog system. The priority of substituents is ranked based on atomic weights, a higher atomic weight, as determined by the systematic procedure, having a higher priority ranking Once the priority ranking of the four groups is determined, the molecule is oriented so that the lowest ranking group is pointed away from the viewer. Then, if the descending rank order of the other groups proceeds clockwise, the molecule is designated (R) and if the descending rank of the other groups proceeds counterclockwise, the molecule is designated (S). In the example in Scheme 14, the Cahn-Ingold-Prelog ranking is A>B>C>D. The lowest ranking atom, D is oriented away from the viewer.

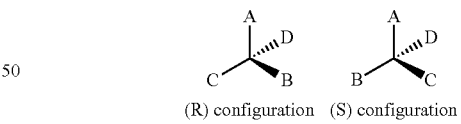

(R) configuration   (S) configuration

The present invention is meant to encompass diastereomers as well as their racemic and resolved, diastereomerically and enantiomerically pure forms and salts thereof. Diastereomeric pairs may be resolved by known separation techniques including normal and reverse phase chromatography, and crystallization.

"Isolated optical isomer" means a compound which has been substantially purified from the corresponding optical isomer(s) of the same formula. Preferably, the isolated isomer is at least about 80%, more preferably at least 90% pure, even more preferably at least 98% pure, most preferably at least about 99% pure, by weight.

Isolated optical isomers may be purified from racemic mixtures by well-known chiral separation techniques.

According to one such method, a racemic mixture of a compound of the invention, or a chiral intermediate thereof, is separated into 99% wt. % pure optical isomers by HPLC using a suitable chiral column, such as a member of the series of DAICEL® CHIRALPAK® family of columns (Daicel Chemical Industries, Ltd., Tokyo, Japan). The column is operated according to the manufacturer instructions.

Rotational Isomerism

It is understood that due to chemical properties (i.e., resonance lending some double bond character to the C—N bond) of restricted rotation about the amide bond linkage (as illustrated below) it is possible to observe separate rotamer species and even, under some circumstances, to isolate such species (see below). It is further understood that certain structural elements, including steric bulk or substituents on the amide nitrogen, may enhance the stability of a rotamer to the extent that a compound may be isolated as, and exist indefinitely, as a single stable rotamer. The present invention therefore includes any possible stable rotamers of formula (I) which are biologically active in the treatment of cancer or other proliferative disease states.

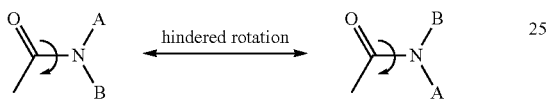

Regioisomerism

The preferred compounds of the present invention have a particular spatial arrangement of substituents on the aromatic rings, which is related to the structure activity relationship demonstrated by the compound class. Often such substitution arrangement is denoted by a numbering system; however, numbering systems are often not consistent between different ring systems. In six-membered aromatic systems, the spatial arrangements are specified by the common nomenclature "para" for 1,4-substitution, "meta" for 1,3-substitution and "ortho" for 1,2-substitution as shown below.

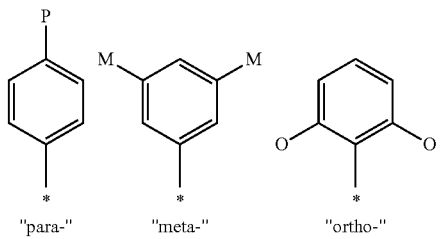

In various embodiments, the compound or set of compounds, such as are among the inventive compounds or are used in the inventive methods, can be any one of any of the combinations and/or sub-combinations of the above-listed embodiments.

In various embodiments, a compound as shown in any of the Examples, or among the exemplary compounds, is provided. Provisos may apply to any of the disclosed categories or embodiments wherein any one or more of the other above disclosed embodiments or species may be excluded from such categories or embodiments.

The compounds of the invention and intermediates may be isolated from their reaction mixtures and purified by standard techniques such as filtration, liquid-liquid extraction, solid phase extraction, distillation, recrystallization or chromatography, including flash column chromatography, or HPLC.

DESCRIPTION

In various embodiments, the invention provides a compound of formula (I),

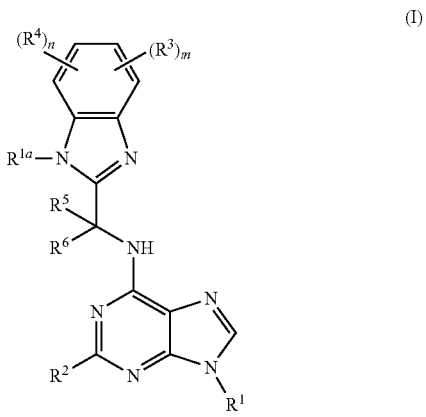

wherein $R^1$ and $R^{1a}$ are each independently selected from the group consisting of hydrogen, deuterium, $(CH_2)_{0-4}N(R)_2$, $(CH_2)_{0-4}SO_3R$, $(CH_2)_{0-4}C(O)R$, $(CH_2)_{0-4}C(O)C(O)R$, $(CH_2)_{0-4}C(O)CH_2C(O)R$, $(CH_2)_{0-4}C(S)R$, $(CH_2)_{0-4}C(O)OR$, $(CH_2)_{0-4}OC(O)R$, $(CH_2)_{0-4}OC(O)OR$, $(CH_2)_{0-4}C(O)N(R)_2$, $OC(O)N(R)_2$, $(CH_2)_{0-4}C(S)N(R)_2$, $(CH_2)_{0-4}NHC(O)R$, $(CH_2)_{0-4}N(R)SO_2R$, $(CH_2)_{0-4}N(R)SO_2N(R)_2$, $(CH_2)_{0-4}N(R)C(O)OR$, $(CH_2)_{0-4}N(R)C(O)R$, $(CH_2)_{0-4}N(R)C(S)R$, $(CH_2)_{0-4}N(R)C(O)N(R)_2$, $(CH_2)_{0-4}N(R)C(S)N(R)_2$, $(CH_2)_{0-4}N(COR)COR$, $(CH_2)_{0-4}N(OR)R$, $(CH_2)_{0-4}C(=NH)N(R_2)$, $(CH_2)_{0-4}C(O)N(OR)R$, $(CH_2)_{0-4}C(=NOR)R$, $(C_{1-4})$alkyl, $(C_{1-4})$alkoxy, $(C_{1-4})$acyloxy, cycloalkyl, heterocyclyl, aryl, and heteroaryl; wherein any alkyl, alkoxy, acyloxy, cycloalkyl, heterocyclyl, aryl, heteroaryl can be mono- or independently multi-substituted with J, $(C_{1-6})$alkyl, $(C_{2-6})$alkenyl, $(C_{2-6})$alkynyl, $(C_{1-6})$haloalkyl, $(C_{1-6})$alkoxy, $(C_{1-6})$haloalkoxy, cycloalkyl$(C_{0-6})$alkyl, heterocyclyl$(C_{1-6})$alkyl, aryl$(C_{0-6})$alkyl, or heteroaryl$(C_{0-6})$alkyl, of which any alkyl, alkenyl, alkynyl, haloalkyl, alkoxy, haloalkoxy, cycloalkyl, aryl, heterocyclyl, or heteroaryl can be further substituted with J;

$R^2$, $R^3$, $R^4$, $R^5$, and $R^6$ each are independently selected from the group consisting of F, Cl, Br, I, OR, CN, $CF_3$, $OCF_3$, $NO_2$, R, $(CH_2)_{0-4}N(R)_2$, $(CH_2)_{0-4}SR$, $(CH_2)_{0-4}SOR$, $(CH_2)_{0-4}SO_2R$, $(CH_2)_{0-4}SO_2N(R)_2$, $(CH_2)_{0-4}SO_3R$, $(CH_2)_{0-4}C(O)R$, $(CH_2)_{0-4}C(O)C(O)R$, $(CH_2)_{0-4}C(O)CH_2C(O)R$, $(CH_2)_{0-4}C(S)R$, $(CH_2)_{0-4}C(O)OR$, $(CH_2)_{0-4}OC(O)R$, $(CH_2)_{0-4}OC(O)OR$, $(CH_2)_{0-4}C(O)N(R)_2$, $(CH_2)_{0-4}OC(O)N(R)_2$, $(CH_2)_{0-4}C(S)N(R)_2$, $(CH_2)_{0-4}NHC(O)R$, $(CH_2)_{0-4}N(R)N(R)C(O)R$, $(CH_2)_{0-4}N(R)N(R)C(O)OR$, $(CH_2)_{0-4}N(R)N(R)CON(R_2)$, $(CH_2)_{0-4}N(R)SO_2R$, $(CH_2)_{0-4}N(R)SO_2N(R)_2$, $(CH_2)_{0-4}N(R)C(O)OR$, $(CH_2)_{0-4}N(R)C(O)R$, $(CH_2)_{0-4}N(R)C(S)R$, $(CH_2)_{0-4}N(R)C(O)N(R)_2$, $(CH_2)_{0-4}N(R)C(S)N(R)_2$, $(CH_2)_{0-4}N(COR)COR$, $(CH_2)_{0-4}N(OR)R$, $(CH_2)_{0-4}C(=NH)N(R_2)$, $(CH_2)_{0-4}C(O)N(OR)R$, $(CH_2)_{0-4}C(=NOR)R$, $(C_{1-4})$alkyl, $(C_{1-4})$alkoxy, $(C_{1-4})$acyloxy, cycloalkyl, heterocyclyl, aryl, and heteroaryl; wherein any alkyl, alkoxy, acyloxy, cycloalkyl, heterocyclyl, aryl, heteroaryl can be mono- or independently multi-substituted with J, $(C_{1-6})$alkyl, $(C_{2-6})$alkenyl, $(C_{2-6})$alkynyl, $(C_{1-6})$haloalkyl, $(C_{1-6})$alkoxy, $(C_{1-6})$haloalkoxy, cycloalkyl$(C_{0-6})$alkyl, heterocyclyl$(C_{0-6})$alkyl, aryl$(C_{0-6})$alkyl, or heteroaryl$(C_{0-6})$alkyl; wherein any alkyl, alkenyl, alkynyl, haloalkyl, alkoxy, haloalkoxy, cycloalkyl, aryl, heterocyclyl, or heteroaryl can be further substituted with J;

wherein m and n are each independently 0, 1, 2, or 3, provided m plus n is less than or equal to 4;

wherein J independently at each occurrence is selected from the group consisting of F, Cl, Br, I, OR, CN, $CF_3$, $OCF_3$, $NO_2$, R, O, S, C(O), C(S), S(O), methylenedioxy, ethylenedioxy, $N(R)_2$, SR, SOR, $SO_2R$, $SO_2N(R)_2$, $SO_3R$, C(O)R, C(O)C(O)R, C(O)CH$_2$C(O)R, C(S)R, C(O)OR, OC(O)R, OC(O)OR, C(O)N(R)$_2$, OC(O)N(R)$_2$, C(S)N(R)$_2$, $(CH_2)_{0-4}$NHC(O)R, N(R)N(R)C(O)R, N(R)N(R)C(O)OR, N(R)N(R)CON(R$_2$), N(R)SO$_2$R, N(R)SO$_2$N(R)$_2$, N(R)C(O)OR, N(R)C(O)R, N(R)C(S)R, N(R)C(O)N(R)$_2$, N(R)C(S)N(R)$_2$, N(COR)COR, N(OR)R, C(=NH)N(R$_2$), C(O)N(OR)R, C(=NOR)R, $(C_{1-4})$alkyl, $(C_{1-4})$alkoxy, $(C_{1-4})$acyloxy, cycloalkyl, heterocyclyl, aryl, and heteroaryl; wherein any alkyl, alkoxy, acyloxy, cycloalkyl, heterocyclyl, aryl, hetero aryl can be mono- or independently multi-substituted with R, $(C_{1-6})$alkyl, $(C_{2-6})$alkenyl, $(C_{2-6})$alkynyl, $(C_{1-6})$haloalkyl, $(C_{1-6})$alkoxy, $(C_{1-6})$haloalkoxy, cycloalkyl$(C_{0-6})$alkyl, heterocyclyl$(C_{0-6})$alkyl, aryl$(C_{0-6})$alkyl, or heteroaryl$(C_{0-6})$alkyl; wherein any alkyl, alkenyl, alkynyl, haloalkyl, alkoxy, haloalkoxy, cycloalkyl, aryl, heterocyclyl, or heteroaryl can be further mono- or independently multi-substituted with R; or wherein two R groups together with a nitrogen atom or with two adjacent nitrogen atoms to which they are bonded can together form a $(C_{3-8})$heterocyclyl mono- or multi-substituted with R; optionally further including 1-3 additional heteroatoms selected from the group consisting of O, N, S, S(O) and $S(O)_2$;

wherein R is independently at each occurrence is selected from the group consisting of hydrogen, deuterium, F, Cl, Br, I, OH, CN, $CF_3$, $OCF_3$, $NO_2$, alkyl, cycloalkyl, cycloalkylalkyl, aryl, aralkyl, heterocyclyl, heterocyclylalkyl, heteroaryl, and heteroarylalkyl; wherein any alkyl, cycloalkyl, cycloalkylalkyl, aryl, aralkyl, heterocyclyl, heterocyclylalkyl, heteroaryl, or heteroarylalkyl is substituted with 0-3 J; or wherein two R groups together with a nitrogen atom or with two adjacent nitrogen atoms to which they are bonded can together form a $(C_{3-8})$heterocyclyl substituted with 0-3 J; optionally further including 1-3 additional heteroatoms selected from the group consisting of O, N, S, S(O) and $S(O)_2$;

wherein any cycloalkyl, aryl, heterocyclyl, or heteroaryl can be fused, bridged, or in a spiro configuration with one or more additional optionally mono- or independently multi-J substituted cycloalkyl, aryl, heterocyclyl, and hetero aryl, monocyclic, bicyclic, bicyclic or polycyclic, saturated, partially unsaturated, or aromatic rings;

wherein the compound of formula (I) can be any stereoisomer thereof, or any salt, hydrate, solvate, prodrug, or metabolite thereof.

In various embodiments, the invention provides a compound of formula (I),

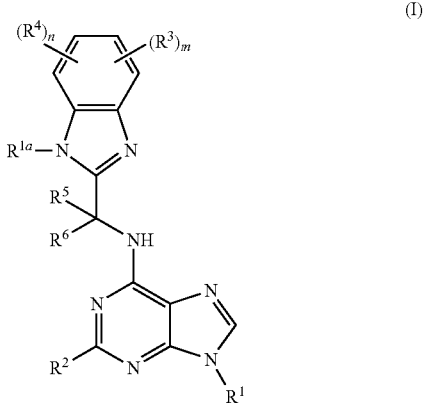

wherein
$R^1$ and $R^{1a}$ are each independently selected from the group consisting of hydrogen, deuterium, $(CH_2)_{0-4}N(R)_2$, $(CH_2)_{0-4}SO_3R$, $(CH_2)_{0-4}C(O)R$, $(CH_2)_{0-4}C(O)C(O)R$, $(CH_2)_{0-4}C(O)CH_2C(O)R$, $(CH_2)_{0-4}C(S)R$, $(CH_2)_{0-4}C(O)OR$, $(CH_2)_{0-4}OC(O)R$, $(CH_2)_{0-4}OC(O)OR$, $(CH_2)_{0-4}C(O)N(R)_2$, $OC(O)N(R)_2$, $(CH_2)_{0-4}C(S)N(R)_2$, $(CH_2)_{0-4}NHC(O)R$, $(CH_2)_{0-4}N(R)SO_2R$, $(CH_2)_{0-4}N(R)SO_2N(R)_2$, $(CH_2)_{0-4}N(R)C(O)OR$, $(CH_2)_{0-4}N(R)C(O)R$, $(CH_2)_{0-4}N(R)C(S)R$, $(CH_2)_{0-4}N(R)C(O)N(R)_2$, $(CH_2)_{0-4}N(R)C(S)N(R)_2$, $(CH_2)_{0-4}N(COR)COR$, $(CH_2)_{0-4}N(OR)R$, $(CH_2)_{0-4}C(=NH)N(R_2)$, $(CH_2)_{0-4}C(O)N(OR)R$, $(CH_2)_{0-4}C(=NOR)R$, $(C_{1-4})$alkyl, $(C_{1-4})$alkoxy, $(C_{1-4})$acyloxy, cycloalkyl, heterocyclyl, aryl, and heteroaryl; wherein any alkyl, alkoxy, acyloxy, cycloalkyl, heterocyclyl, aryl, heteroaryl can be mono- or independently multi-substituted with J, $(C_{1-6})$alkyl, $(C_{2-6})$alkenyl, $(C_{2-6})$alkyayl, $(C_{1-6})$haloalkyl, $(C_{1-6})$alkoxy, $(C_{1-6})$haloalkoxy, cycloalkyl$(C_{0-6})$alkyl, heterocyclyl$(C_{0-6})$alkyl, aryl$(C_{0-6})$alkyl, or heteroaryl$(C_{0-6})$alkyl, of which any alkyl, alkenyl, alkynyl, haloalkyl, alkoxy, haloalkoxy, cycloalkyl, aryl, heterocyclyl, or heteroaryl can be further substituted with J;

$R^2$, $R^3$, $R^4$, $R^5$, and $R^6$ each are independently selected from the group consisting of F, Cl, Br, I, OR, CN, $CF_3$, $OCF_3$, $NO_2$, R, $(CH_2)_{0-4}N(R)_2$, $(CH_2)_{0-4}SR$, $(CH_2)_{0-4}SOR$, $(CH_2)_{0-4}SO_2R$, $(CH_2)_{0-4}SO_2N(R)_2$, $(CH_2)_{0-4}SO_3R$, $(CH_2)_{0-4}C(O)R$, $(CH_2)_{0-4}C(O)C(O)R$, $(CH_2)_{0-4}C(O)CH_2C(O)R$, $(CH_2)_{0-4}C(S)R$, $(CH_2)_{0-4}C(O)OR$, $(CH_2)_{0-4}OC(O)R$, $(CH_2)_{0-4}OC(O)OR$, $(CH_2)_{0-4}C(O)N(R)_2$, $(CH_2)_{0-4}OC(O)N(R)_2$, $(CH_2)_{0-4}C(S)N(R)_2$, $(CH_2)_{0-4}NHC(O)R$, $(CH_2)_{0-4}N(R)N(R)C(O)R$, $(CH_2)_{0-4}N(R)N(R)C(O)OR$, $(CH_2)_{0-4}N(R)N(R)CON(R_2)$, $(CH_2)_{0-4}N(R)SO_2R$, $(CH_2)_{0-4}N(R)SO_2N(R)_2$, $(CH_2)_{0-4}N(R)C(O)OR$, $(CH_2)_{0-4}N(R)C(O)R$, $(CH_2)_{0-4}N(R)C(S)R$, $(CH_2)_{0-4}N(R)C(O)N(R)_2$, $(CH_2)_{0-4}N(R)C(S)N(R)_2$, $(CH_2)_{0-4}N(COR)COR$, $(CH_2)_{0-4}N(OR)R$, $(CH_2)_{0-4}C(=NH)N(R_2)$, $(CH_2)_{0-4}C(O)N(OR)R$, $(CH_2)_{0-4}C(=NOR)R$, $(C_{1-4})$alkyl, $(C_{1-4})$alkoxy, $(C_{1-4})$acyloxy, cycloalkyl, heterocyclyl, aryl, and heteroaryl; wherein any alkyl, alkoxy, acyloxy, cycloalkyl, heterocyclyl, aryl, heteroaryl can be mono- or independently multi-substituted with J, $(C_{1-6})$alkyl, $(C_{2-6})$alkenyl, $(C_{2-6})$alkynyl, $(C_{1-6})$haloalkyl, $(C_{1-6})$alkoxy, $(C_{1-6})$haloalkoxy, cycloalkyl$(C_{0-6})$alkyl, heterocyclyl$(C_{0-6})$alkyl, aryl$(C_{0-6})$alkyl, or heteroaryl$(C_{0-6})$alkyl; wherein any alkyl, alkenyl, alkynyl, haloalkyl, alkoxy, haloalkoxy, cycloalkyl, aryl, heterocyclyl, or heteroaryl can be further substituted with J;

wherein m and n are each independently 0, 1, 2, or 3, provided m plus n is less than or equal to 4;

wherein J independently at each occurrence is selected from the group consisting of F, Cl, Br, I, OR, CN, $CF_3$, $OCF_3$, $NO_2$, R, O, S, C(O), C(S), S(O), methylenedioxy, ethylenedioxy, $N(R)_2$, SR, SOR, $SO_2R$, $SO_2N(R)_2$, $SO_3R$, C(O)R, C(O)C(O)R, $C(O)CH_2C(O)R$, C(S)R, C(O)OR, OC(O)R, OC(O)OR, $C(O)N(R)_2$, $OC(O)N(R)_2$, $C(S)N(R)_2$, $(CH_2)_{0-4}NHC(O)R$, N(R)N(R)C(O)R, N(R)N(R)C(O)OR, $N(R)N(R)CON(R_2)$, $N(R)SO_2R$, $N(R)SO_2N(R)_2$, N(R)C(O)OR, N(R)C(O)R, N(R)C(S)R, $N(R)C(O)N(R)_2$, $N(R)C(S)N(R)_2$, N(COR)COR, N(OR)R, $C(=NH)N(R_2)$, C(O)N(OR)R, C(=NOR)R, $(C_{1-4})$alkyl, $(C_{1-4})$alkoxy, $(C_{1-4})$acyloxy, cycloalkyl, heterocyclyl, aryl, and heteroaryl; wherein any alkyl, alkoxy, acyloxy, cycloalkyl, heterocyclyl, aryl, hetero aryl can be mono- or independently multi-substituted with R, $(C_{1-6})$alkyl, $(C_{2-6})$alkenyl, $(C_{2-6})$alkynyl, $(C_{1-6})$haloalkyl, $(C_{1-6})$alkoxy, $(C_{1-6})$haloalkoxy, cycloalkyl$(C_{0-6})$alkyl, heterocyclyl$(C_{0-6})$alkyl, aryl$(C_{0-6})$alkyl, or heteroaryl$(C_{0-6})$alkyl; wherein any alkyl, alkenyl, alkynyl, haloalkyl, alkoxy, haloalkoxy, cycloalkyl, aryl, heterocyclyl, or heteroaryl can be further mono- or independently multi-substituted with R; or wherein two R groups together with a nitrogen atom or with two adjacent nitrogen atoms to which they are bonded can together form a $(C_{3-8})$heterocyclyl mono- or multi-substituted with R; optionally further including 1-3 additional hetero atoms selected from the group consisting of O, N, S, S(O) and $S(O)_2$;

wherein R is independently at each occurrence is selected from the group consisting of hydrogen, deuterium, F, Cl, Br, I, OH, CN, $CF_3$, $OCF_3$, $NO_2$, alkyl, cycloalkyl, cycloalkylalkyl, aryl, aralkyl, heterocyclyl, heterocyclylalkyl, heteroaryl, and heteroarylalkyl; wherein any alkyl, cycloalkyl, cycloalkylalkyl, aryl, aralkyl, heterocyclyl, heterocyclylalkyl, heteroaryl, or heteroarylalkyl is substituted with 0-3 $J^R$; or wherein two R groups together with a nitrogen atom or with two adjacent nitrogen atoms to which they are bonded can together form a $(C_{3-8})$heterocyclyl substituted with 0-3 $J^R$; optionally further comprising 1-3 additional hetero atoms selected from the group consisting of O, N, S, S(O) and $S(O)_2$;

wherein any cycloalkyl, aryl, heterocyclyl, or heteroaryl can be fused, bridged, or in a spiro configuration with one or more additional optionally mono- or independently multi-$J^R$ substituted cycloalkyl, aryl, heterocyclyl, and heteroaryl, monocyclic, bicyclic, bicyclic or polycyclic, saturated, partially unsaturated, or aromatic rings;

wherein $J^R$ is independently at each occurrence is selected from the group consisting of F, Cl, Br, I, OR, CN, $CF_3$, $OCF_3$, $NO_2$, O, S, C(O), C(S), S(O), methylenedioxy, ethylenedioxy, $N(R)_2$, SR, SOR, $SO_2R$, $SO_2N(R)_2$, $SO_3R$, C(O)R, C(O)C(O)R, $C(O)CH_2C(O)R$, C(S)R, C(O)OR, OC(O)R, OC(O)OR, $C(O)N(R)_2$, $OC(O)N(R)_2$, $C(S)N(R)_2$, $(CH_2)_{0-4}NHC(O)R$, N(R)N(R)C(O)R, N(R)N(R)C(O)OR, $N(R)N(R)CON(R_2)$, $N(R)SO_2R$, $N(R)SO_2N(R)_2$, N(R)C(O)OR, N(R)C(O)R, N(R)C(S)R, $N(R)C(O)N(R)_2$, $N(R)C(S)N(R)_2$, N(COR)COR, N(OR)R, $C(=NH)N(R_2)$, C(O)N(OR)R, C(=NOR)R, $(C_{1-4})$alkyl, $(C_{1-4})$alkoxy, $(C_{1-4})$acyloxy, cycloalkyl, heterocyclyl, aryl, and heteroaryl;

provided that the compound of formula (I) is not any of the following:

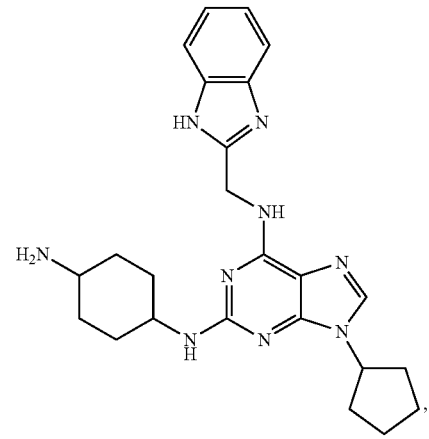

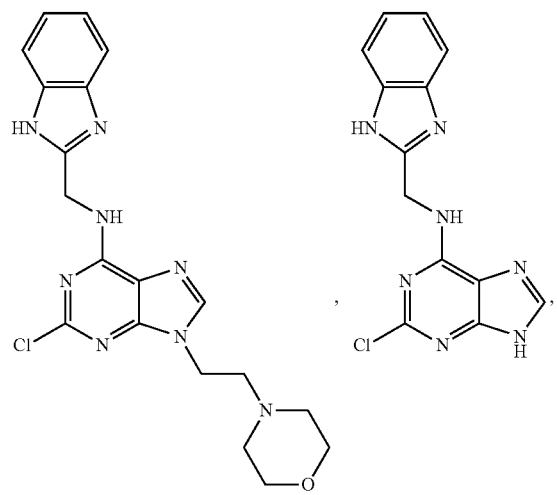

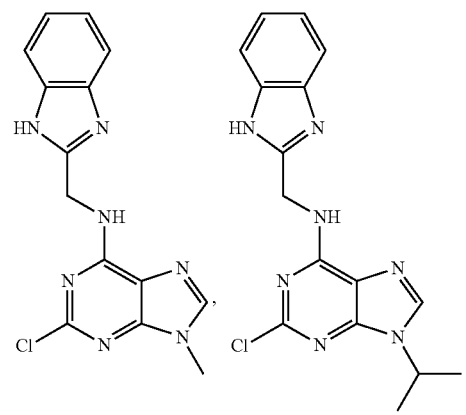

-continued

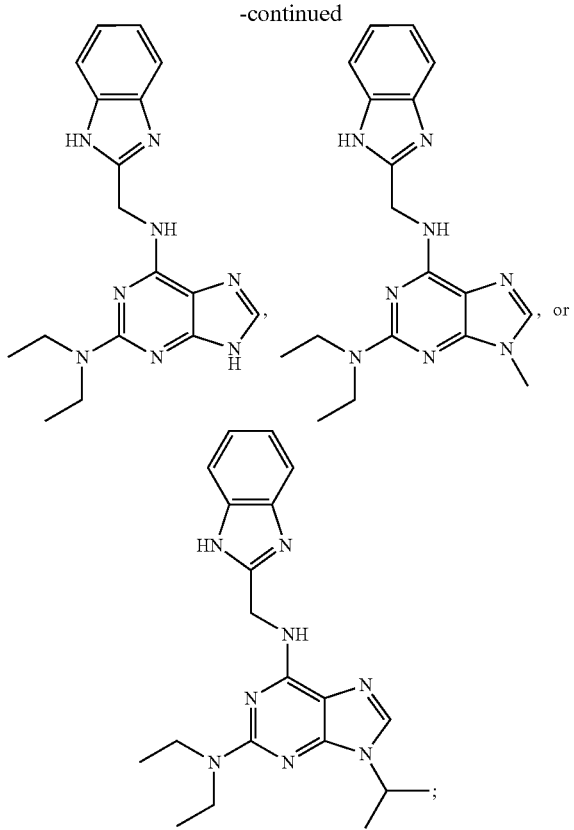

wherein the compound of formula (I) can be any stereoisomer thereof, or any salt, hydrate, solvate, prodrug, or metabolite thereof.

In various embodiments, the invention provides any of the compounds as listed below in "Table 1: Exemplary Compounds of the Invention," or any salt, hydrate, prodrug, or metabolite thereof.

In various embodiments, $R^1$ can be 2-thiophenyl, 3-furanyl, 2-furanyl, 3-1H-pyrrolyl, 2-1H-pyrrolyl, 4-1H-imidazolyl, 2-1H-imidazolyl, 5-oxazolyl, 4-thiazolyl, 2-oxooxazolidin-4-yl, 2-pyridinyl, 3-pyridinyl, 4-pyridinyl, 5-pyrimidinyl, or 2-pyrazinyl. In various embodiments, $R^1$ can be 3-thiophenyl, isopropyl, cyclopentyl, tetrahydro-2H-pyran-2-yl, or H. For example, $R^1$ can be 3-thiophenyl. In another example, $R^1$ can be isopropyl.

In various embodiments, $R^{1a}$ can be 2-thiophenyl, 3-furanyl, 2-furanyl, 3-1H-pyrrolyl, 2-1H-pyrrolyl, 4-1H-imidazolyl, 2-1H-imidazolyl, 5-oxazolyl, 4-thiazolyl, 2-oxooxazolidin-4-yl, 2-pyridinyl, 3-pyridinyl, 4-pyridinyl, 5-pyrimidinyl, or 2-pyrazinyl. In various embodiments, $R^{1a}$ can be 3-thiophenyl, isopropyl, cyclopentyl, tetrahydro-2H-pyran-2-yl, or H. For example, $R^{1a}$ can be 3-thiophenyl. In another example, $R^{1a}$ can be isopropyl.

In various embodiments, $R^1$ can be 3-thiophenyl, isopropyl, cyclopentyl, tetrahydro-2H-pyran-2-yl, or H. In various embodiments, $R^1$ can be 2-thiophenyl, 3-furanyl, 2-furanyl, 3-1H-pyrrolyl, 2-1H-pyrrolyl, 4-1H-imidazolyl, 2-1H-imidazolyl, 5-oxazolyl, 4-thiazolyl, 2-oxooxazolidin-4-yl, 2-pyridinyl, 3-pyridinyl, 4-pyridinyl, 5-pyrimidinyl, or 2-pyrazinyl.

In various embodiments, $R^{1a}$ can be 3-thiophenyl, isopropyl, cyclopentyl, tetrahydro-2H-pyran-2-yl, or H. In various embodiments, $R^{1a}$ can be 2-thiophenyl, 3-furanyl, 2-furanyl, 3-1H-pyrrolyl, 2-1H-pyrrolyl, 4-1H-imidazolyl, 2-1H-imidazolyl, 5-oxazolyl, 4-thiazolyl, 2-oxooxazolidin-4-yl, 2-pyridinyl, 3-pyridinyl, 4-pyridinyl, 5-pyrimidinyl, or 2-pyrazinyl.

In various embodiments, $R^2$ can be 1-pyrrolidinyl, 1-piperidinyl, 1-piperazinyl, 4-methylpiperazin-1-yl, thiomorpholino, 4-(2-hydroxyethyl)piperazin-1-yl, (2-morpholinoethyl)amino, indolin-1-yl, or (R)-2-(1-phenylethyl)-amino. In various embodiments, $R^2$ can be morpholino, 3-pyridinylamino, 2-pyrazinylamino, 4-pyrimidinylamino, 4-(2-pyridinyl)piperazin-1-yl, or 4-(cyclopropylcarbamoyl)phenyl. For example, $R^2$ can be morpholino.

In various embodiments, $R^3$ can be 4-amino, 5-amino, 5-chloro, 4,5-difluoro, 4-nitro, 4-ethoxycarbonyl, 4-carboxylic acid, 4-methylsulfonamido, 4-methylphenylsulfonamido, 4-carbamoyl, 4-hydroxycarbamoyl, 4-methoxycarbamoyl, 4-(N—R-carbamoyl), 4-(5-R-sulfonyl)carbamoyl, 4-(3-hydroxyisoxazol-5-yl), 4-(3-hydroxyisothiazol-5-yl), 4-(5-hydroxyisoxazol-3-yl), 4-(3-hydroxy-1-methyl-1H-pyrazol-5-yl), 4-(1-hydroxy-1H-imadazol-5-yl), 4-(1-hydroxy-1H-imidazol-2-yl), 4-(1H-tetrazol-5-yl), 4-(3,5-difluoro-4-hydroxyphenyl), 4-(3-methyl-1,2,4-thiadiazol-5-yl), 4-(3-methyl-1,2,4-oxadiazol-5-yl), 4-(5-methyl-1,3,4-oxadiazol-2-yl), 4-(4-methoxy-1,2,5-oxadiazol-3-yl), 4-(5-methoxy-2-methyl-2H-1,2,3-triazol-4-yl), and 4-(2-methyl-2H-tetrazol-5-yl), wherein R is as defined above. In the above groups, the letter R refers to the substituent R as defined, not to a stereochemical designation of the configuration of a chiral center.

In various embodiments, $R^3$ can be 4-trifluoromethanyl, 5-trifluoromethanyl, 5-fluoro, 5-cyano, 5-nitro, 5-methoxy, 5-chloro, 4-nitro, 4-ethoxycarbonyl, 5-ethoxycarbonyl, 4-$CO_2R$, 5-$CO_2R$, or H, wherein R is as defined above. In one example, $R^3$ can be 4-bromo, and $R^4$ can be 6-trifluromethyl. In another example $R^3$ can be 4-$NO_2$. In another example, the compound of formula (I) can have an $R^3$ that is $CO_2Et$ at the 4-position.

In various embodiments, $R^4$ can be 4-amino, 5-amino, 5-chloro, 4,5-difluoro, 4-nitro, 4-ethoxycarbonyl, 4-carboxylic acid, 4-methylsulfonamido, 4-methylphenylsulfonamido, 4-carbamoyl, 4-hydroxycarbamoyl, 4-methoxycarbamoyl, 4-(N—R-carbamoyl), 4-(S—R-sulfonyl)carbamoyl, 4-(3-hydroxyisoxazol-5-yl), 4-(3-hydroxyisothiazol-5-yl), 4-(5-hydroxyisoxazol-3-yl), 4-(3-hydroxy-1-methyl-1H-pyrazol-5-yl), 4-(1-hydroxy-1H-imadazol-5-yl), 4-(1-hydroxy-1H-imidazol-2-yl), 4-(1H-tetrazol-5-yl), 4-(3,5-difluoro-4-hydroxyphenyl), 4-(3-methyl-1,2,4-thiadiazol-5-yl), 4-(3-methyl-1,2,4-oxadiazol-5-yl), 4-(5-methyl-1,3,4-oxadiazol-2-yl), 4-(4-methoxy-1,2,5-oxadiazol-3-yl), 4-(5-methoxy-2-methyl-2H-1,2,3-triazol-4-yl), and 4-(2-methyl-2H-tetrazol-5-yl), wherein R is as defined above. In the above groups, the letter R refers to the substituent R as defined, not to a stereochemical designation of the configuration of a chiral center.

In various embodiments, $R^4$ can be 4-trifluoromethanyl, 5-trifluoromethanyl, 5-fluoro, 5-cyano, 5-nitro, 5-methoxy, 5-chloro, 4-nitro, 4-ethoxycarbonyl, 5-ethoxycarbonyl, 4-$CO_2R$, 5-$CO_2R$, or H, wherein R is as defined above. In one example $R^4$ can be 4-$NO_2$. In another example, the compound of formula (I) can have an $R^4$ that is $CO_2Et$ at the 4-position.

In various embodiments, $R^3$ and $R^4$ can together form a benzene ring fused at the f-side of the 1H-benzo[d]imidazole to give a 2-substituted-1H-naphtho[2,3-d]imidazole, or $R^3$ and $R^4$ can together form a pyridine ring 3,2-fused to the e-side of the 1H-benzo[d]imidazole to give a 2-substituted-3H-imidazo[4,5-f]quinoline.

In various embodiments, $R^4$ can be H (hydrogen) or D (deuterium). In various embodiments, $R^5$ and $R^6$ can be independently H or D.

In various embodiments, the compound of formula (I) can be any of

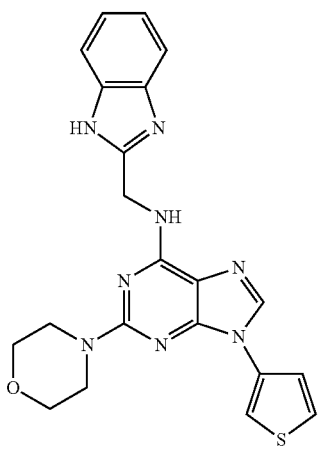

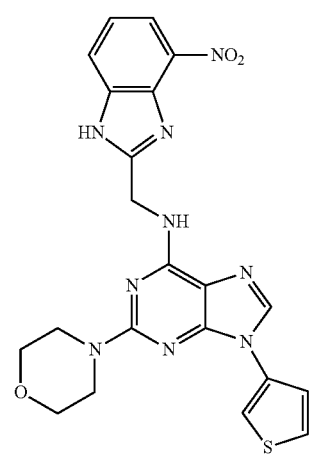

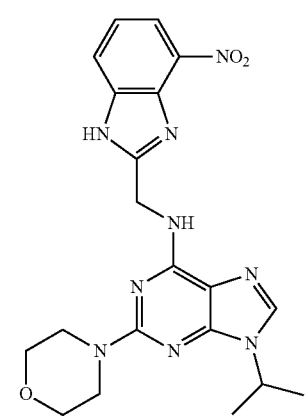

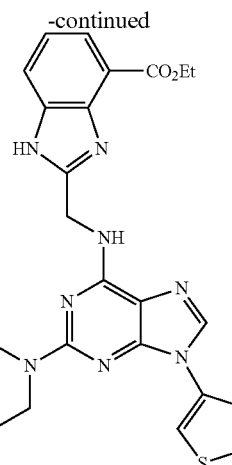

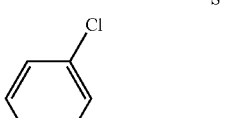

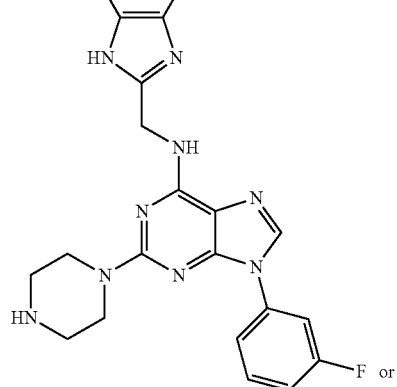

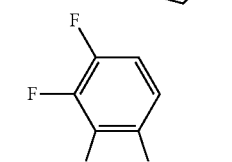

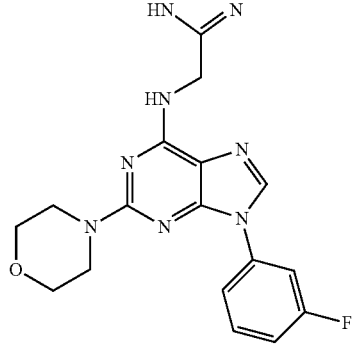

In various embodiments, the present invention provides a pharmaceutical composition that includes a compound of formula (I) and a pharmaceutically acceptable carrier.

In various embodiments, the present invention includes a compound of formula (I) wherein the compound reduces amyloid beta 40 production, or wherein the compound inhibits the degradation of Wee1, or wherein the compound inhibits cell proliferation, or wherein the compound inhibits casein kinase 1 (CK1), or any combination thereof.

In various embodiments, the present invention includes a method including contacting one or more cells with an effective amount of the compound of formula (I) wherein the method reduces amyloid beta 40 production, reduces cell proliferation, inhibits the degradation of Wee1, inhibits casein kinase 1 (CK1), or a combination thereof. The contacting one or more cells can include contacting in vivo in a human patient. The method can include an amount or concentration of the compound of formula (I) effective to selectively inhibit the degradation of Wee1.

In various embodiments, the present invention includes a method of treatment of a malcondition in a patient for which inhibition of the degradation of Wee1 is medically indicated, including administering to the patient a compound of formula (I) in a dose, at a frequency, and for a duration sufficient to provide a beneficial effect to the patient. The malcondition can include cancer, Alzheimer's, or other malconditions, including: neurological disorders, psychiatric disorders, inflammation-related disorders, and combinations thereof.

In various embodiments, the present invention provides the use of a compound of formula (I) in the treatment of a malcondition in a human patient. The malcondition can include those malconditions wherein inhibition of the degradation of Wee1 is medically indicated. The malcondition can include cancer, Alzheimer's, and other malconditions, including: neurological disorders, psychiatric disorders, and inflammation-related disorders, and combinations thereof.

In various embodiments, the present invention provides a method of synthesis of a compound of any one of claims 1-23, including: contacting a 2,6-dihalopurine with an $R^1$-substituted boronic acid, to provide a 9-$R^1$-substituted-2,6-dihalopurine; contacting the 9-R1-substituted-2,6-dihalopurine with an (1H-benzo[d]imidazol-2-yl)methanamine, to provide an N-((1H-benzo[d]imidazol-2-yl)methyl)-2-halo-9-$R^1$-substituted-purin-6-amine; and contacting the N-((1H-benzo[d]imidazol-2-yl)methyl)-2-halo-9-$R^1$-substituted-purin-6-amine with an H-substituted-$R^2$, to provide an N-((1H-benzo[d]imidazol-2-yl)methyl)-2-$R^2$-substituted-9-$R^1$-substituted-purin-6-amine of formula (I); wherein $R^1$ and $R^2$ are as defined in claim 1. $R^1$ can be 3-thiophenyl. $R^2$ can be morpholinyl.

In various embodiments, the present invention provides a method of synthesis of a compound of any one of claims 1-23, including: contacting a 2,6-dihalopurine with an $R^1$-substituted boronic acid, to provide a 9-$R^1$-substituted-2,6-dihalopurine; contacting a 3-$R^3$-substituted-benzene-1,2-diamine with N-[(9H-fluoren-9-ylmethoxy)carbonyl]glycine, to provide a (9H-fluoren-9-yl)methyl (2-((2-amino-3-$R^3$-substituted-phenyl)amino)-2-oxoethyl)carbamate; intramolecularly condensing the (9H-fluoren-9-yl)methyl (2-((2-amino-3-$R^3$-substituted-phenyl)amino)-2-oxoethyl)carbamate, to provide a (4-$R^3$-substituted-1H-benzo[d]imidazol-2-yl)methanamine; and contacting the (4-$R^3$-substituted-1H-benzo[d]imidazol-2-yl)methanamine with the 9-$R^1$-substituted-2,6-dihalopurine, followed by contacting the intermediate with an H-substituted-$R^2$, to provide an N-((4-$R^3$-substituted-1H-benzo[d]imidazol-2-yl)methyl)-2-$R^2$-substituted-9-$R^1$-substituted-purin-6-amine of formula (I); wherein $R^1$, $R^2$, and $R^3$ are as defined in claim 1. $R^1$ can be 3-thiophenyl. $R^2$ can be morpholinyl. $R^3$ can be nitro.

TABLE 1

Exemplary Compounds of the Invention

| Compound Number | Structure |
|---|---|
| SR-653234 | 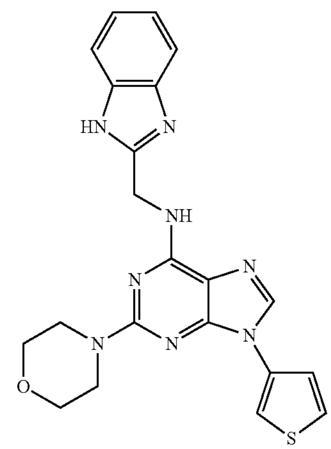 [SMILES: c1ccc2[nH]c(CNc3nc(N4CCOCC4)nc4c3ncn4-c3ccsc3)nc2c1] |
| SR-655534 | 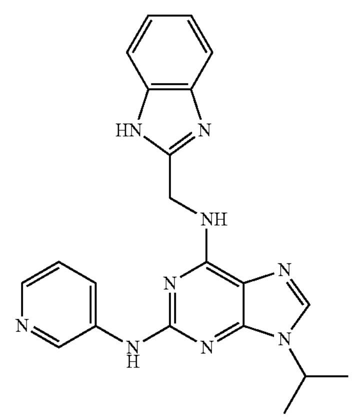 [SMILES: CC(C)n1cnc2c(NCc3nc4ccccc4[nH]3)nc(Nc3cccnc3)nc21] |
| SR-660754 | 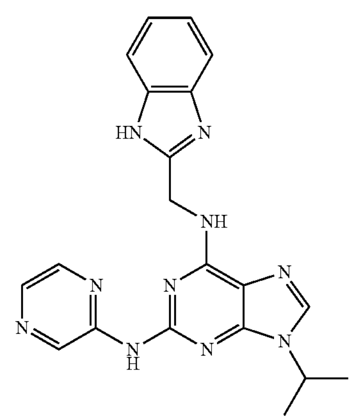 [SMILES: CC(C)n1cnc2c(NCc3nc4ccccc4[nH]3)nc(Nc3cnccn3)nc21] |

TABLE 1-continued
Exemplary Compounds of the Invention
| Compound Number | Structure |
|---|---|
| SR-648126 | 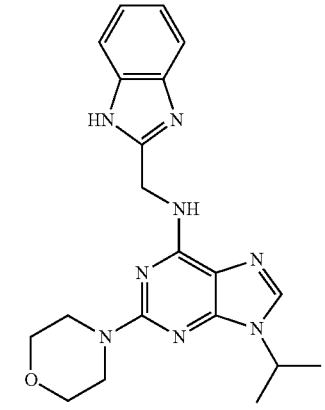 [SMILES: CC(C)n1cnc2c(NCc3nc4ccccc4[nH]3)nc(N3CCOCC3)nc21] |
| SR-649967 | 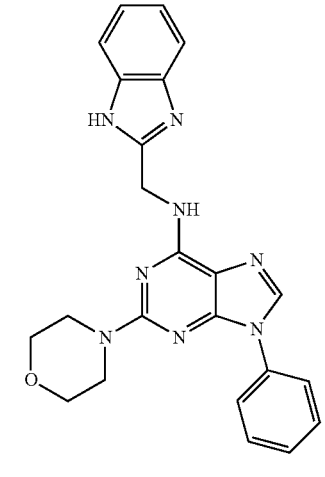 [SMILES: c1ccc(-n2cnc3c(NCc4nc5ccccc5[nH]4)nc(N4CCOCC4)nc32)cc1] |
| SR-656428 | 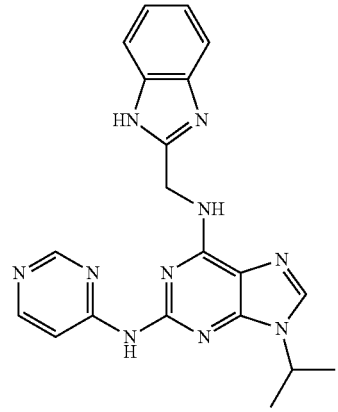 [SMILES: CC(C)n1cnc2c(NCc3nc4ccccc4[nH]3)nc(Nc3ccncn3)nc21] |
| SR-648378 | 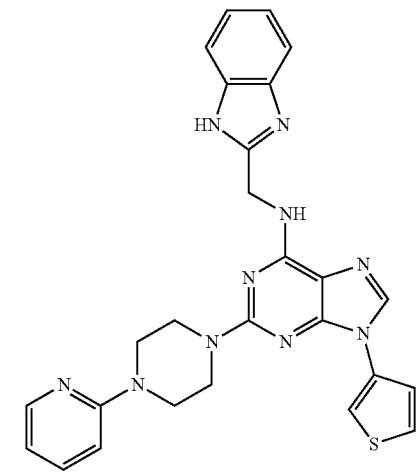 [SMILES: c1ccc(N2CCN(c3nc(NCc4nc5ccccc5[nH]4)c4ncn(-c5ccsc5)c4n3)CC2)nc1] |
| SR-658807 | 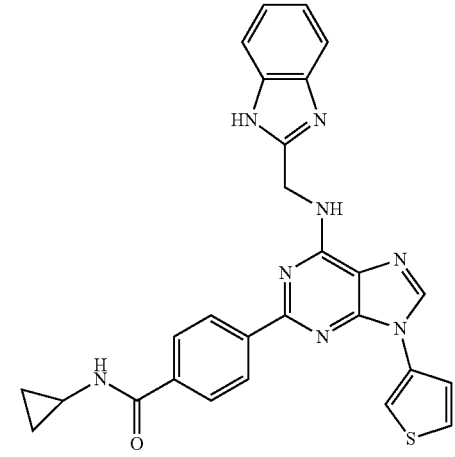 [SMILES: O=C(NC1CC1)c1ccc(-c2nc(NCc3nc4ccccc4[nH]3)c3ncn(-c4ccsc4)c3n2)cc1] |
| SR-660983 | 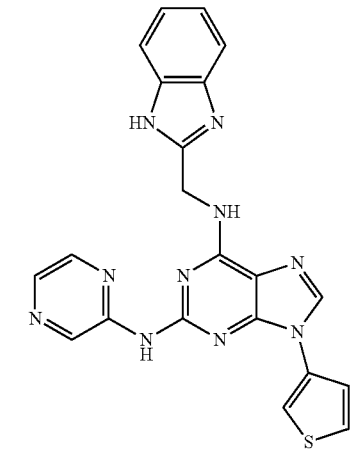 [SMILES: c1ccc2[nH]c(CNc3nc(Nc4cnccn4)nc4c3ncn4-c3ccsc3)nc2c1] |

TABLE 1-continued

Exemplary Compounds of the Invention

| Compound Number | Structure |
|---|---|
| SR-1272 | 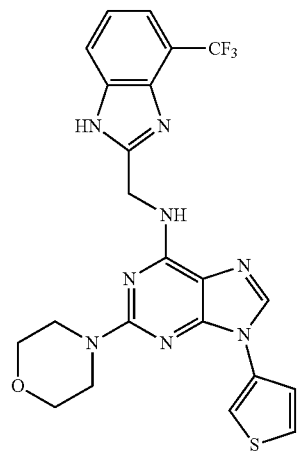 |
| SR-1273 | 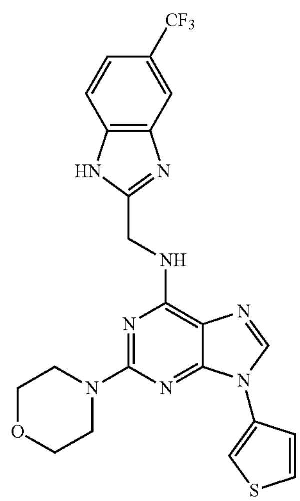 |
| SR-1275 | 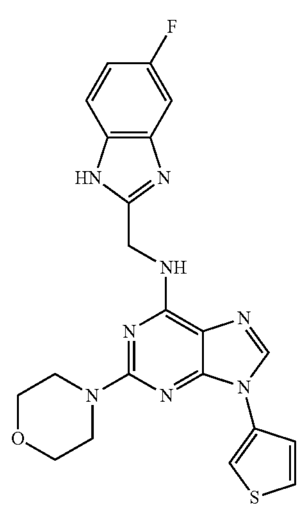 |
| SR-3176 | 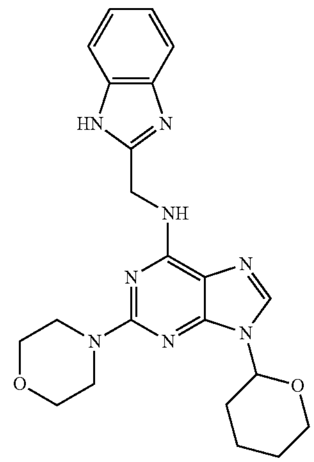 [SMILES: c1ccc2[nH]c(CNc3nc(N4CCOCC4)nc4c3ncn4C3CCCCO3)nc2c1] |
| SR-1276 | 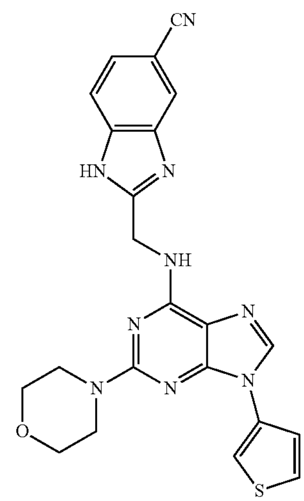 [SMILES: N#Cc1ccc2[nH]c(CNc3nc(N4CCOCC4)nc4c3ncn4-c3ccsc3)nc2c1] |
| SR-1281 | 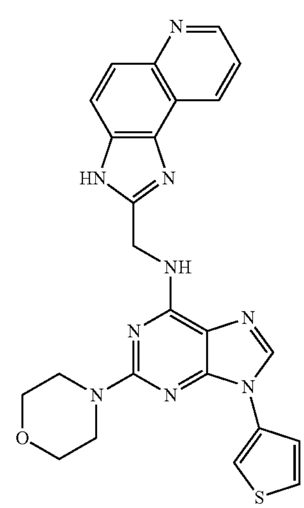 [SMILES: c1cnc2ccc3[nH]c(CNc4nc(N5CCOCC5)nc5c4ncn5-c4ccsc4)nc3c2c1] |

TABLE 1-continued

Exemplary Compounds of the Invention

| Compound Number | Structure |
|---|---|
| SR-1278 | (benzimidazole with 5-NO2)-CH2-NH-[2-morpholino-9-(thiophen-3-yl)-9H-purin-6-yl] |
| SR-1279 | (benzimidazole with 5-OMe)-CH2-NH-[2-morpholino-9-(thiophen-3-yl)-9H-purin-6-yl] |
| SR-1274 | (benzimidazole with 5-Cl)-CH2-NH-[2-morpholino-9-(thiophen-3-yl)-9H-purin-6-yl] |
| SR-1280 | (naphtho[2,3-d]imidazol-2-yl)-CH2-NH-[2-morpholino-9-(thiophen-3-yl)-9H-purin-6-yl] |
| SR-1277 | (benzimidazole with 4-NO2)-CH2-NH-[2-morpholino-9-(thiophen-3-yl)-9H-purin-6-yl] |
| SR-3177 | (1H-benzimidazol-2-yl)-CH2-NH-[2-morpholino-9H-purin-6-yl] |

TABLE 1-continued
Exemplary Compounds of the Invention
| Compound Number | Structure |
|---|---|
| SR-1285 | 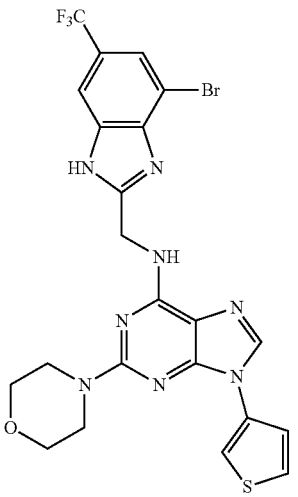 [SMILES: FC(F)(F)c1cc(Br)c2nc(CNc3nc(N4CCOCC4)nc4c3ncn4-c3ccsc3)[nH]c2c1] |
| SR-1287 | 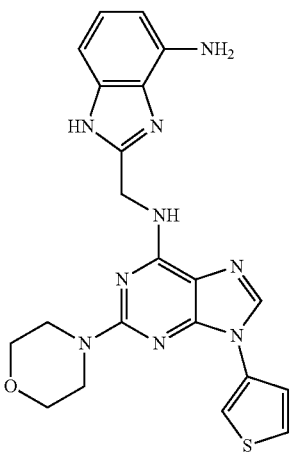 |
| SR-1286 | 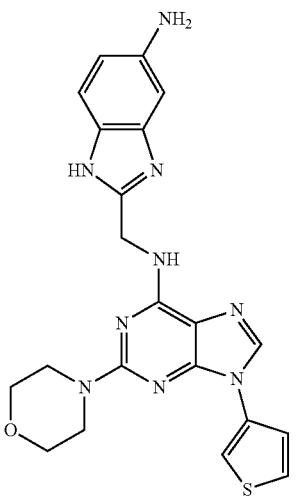 [SMILES: Nc1ccc2[nH]c(CNc3nc(N4CCOCC4)nc4c3ncn4-c3ccsc3)nc2c1] |
| SR-1284 | 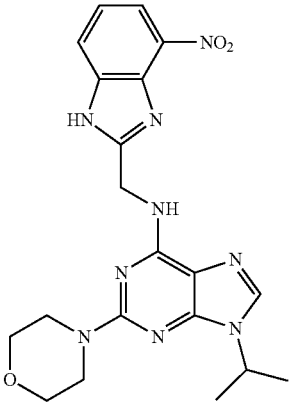 [SMILES: CC(C)n1cnc2c(NCc3nc4c([N+](=O)[O-])cccc4[nH]3)nc(N3CCOCC3)nc21] |
| SR-1282 | 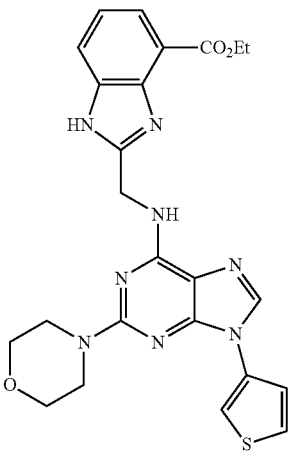 [SMILES: CCOC(=O)c1cccc2[nH]c(CNc3nc(N4CCOCC4)nc4c3ncn4-c3ccsc3)nc12] |
| SR-1283 | 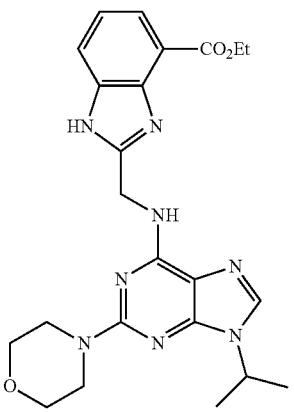 |

TABLE 1-continued

Exemplary Compounds of the Invention

| Compound Number | Structure |
|---|---|
| SR-1401 | 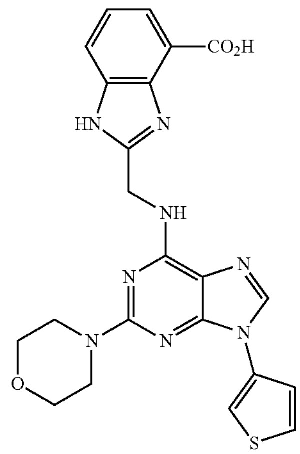 [SMILES: O=C(O)c1cccc2[nH]c(CNc3nc(N4CCOCC4)nc4c3ncn4-c3ccsc3)nc12] |
| SR-1402 | 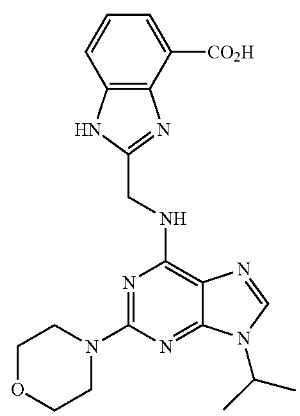 [SMILES: CC(C)n1cnc2c(NCc3nc4c(C(=O)O)cccc4[nH]3)nc(N3CCOCC3)nc21] |
| SR-1293 | 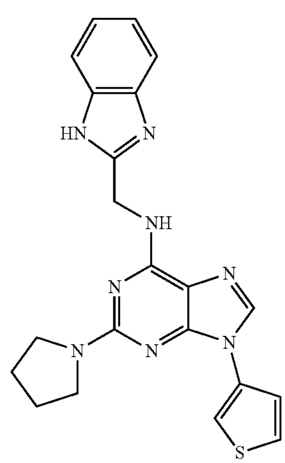 [SMILES: c1ccc2[nH]c(CNc3nc(N4CCCC4)nc4c3ncn4-c3ccsc3)nc2c1] |
| SR-1288 | |
| SR-1292 | |
| SR-1294 | |

TABLE 1-continued
Exemplary Compounds of the Invention
| Compound Number | Structure |
|---|---|
| SR-1291 | 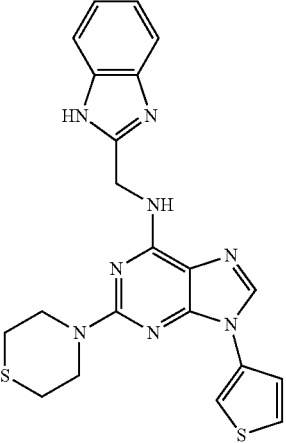 [SMILES: c1ccc2[nH]c(CNc3nc(N4CCSCC4)nc4c3ncn4-c3ccsc3)nc2c1] |
| SR-1296 | 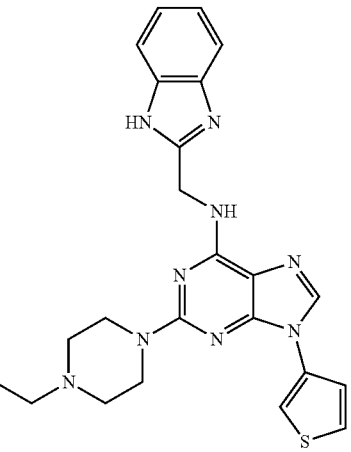 |
| SR-1299 | 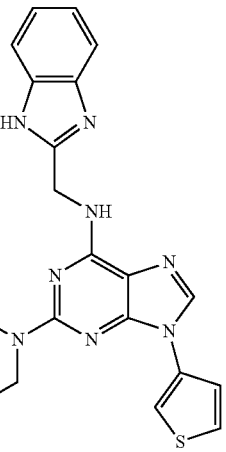 |
| SR-1298 | 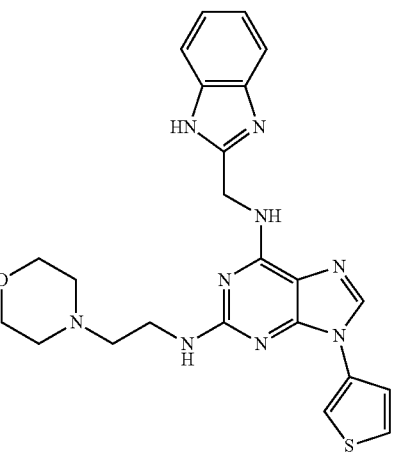 [SMILES: c1ccc2[nH]c(CNc3nc(NCCN4CCOCC4)nc4c3ncn4-c3ccsc3)nc2c1] |
| SR-1297 | 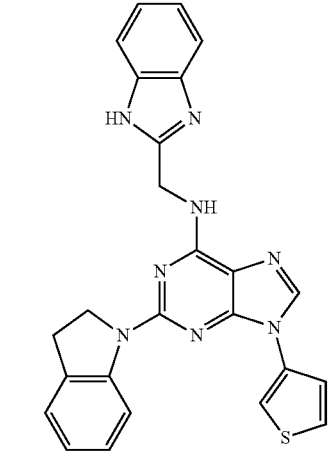 [SMILES: c1ccc2c(c1)CCN2c1nc(NCc2nc3ccccc3[nH]2)c2ncn(-c3ccsc3)c2n1] |
| SR-1289 | 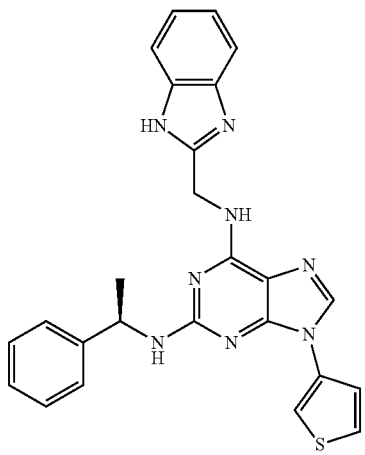 [SMILES: C[C@@H](Nc1nc(NCc2nc3ccccc3[nH]2)c2ncn(-c3ccsc3)c2n1)c1ccccc1] |

TABLE 1-continued

Exemplary Compounds of the Invention

| Compound Number | Structure |
|---|---|
| SR-2149 | 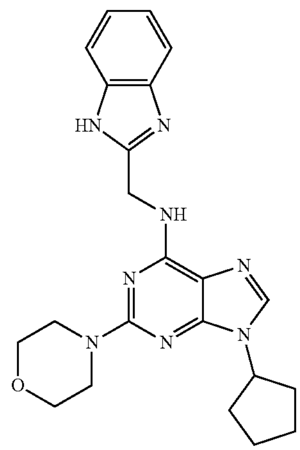 [SMILES: c1ccc2[nH]c(CNc3nc(N4CCOCC4)nc4c3ncn4C3CCCC3)nc2c1] |
| SR-2001 | 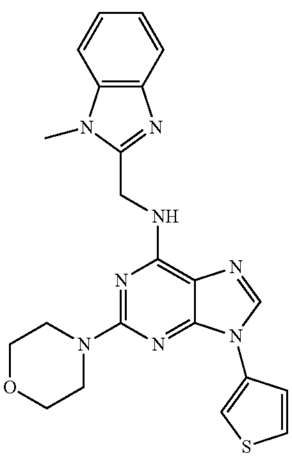 [SMILES: Cn1c(CNc2nc(N3CCOCC3)nc3c2ncn3-c2ccsc2)nc2ccccc21] |
| SR-1295 | 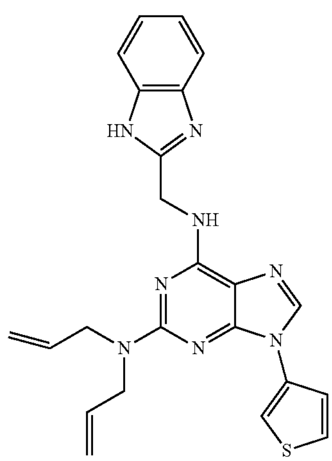 [SMILES: C=CCN(CC=C)c1nc(NCc2nc3ccccc3[nH]2)c2ncn(-c3ccsc3)c2n1] |
| SR-2007 | |
| SR-2362 | |
| SR-2364 | |

TABLE 1-continued
Exemplary Compounds of the Invention
| Compound Number | Structure |
|---|---|
| SR-2366 | 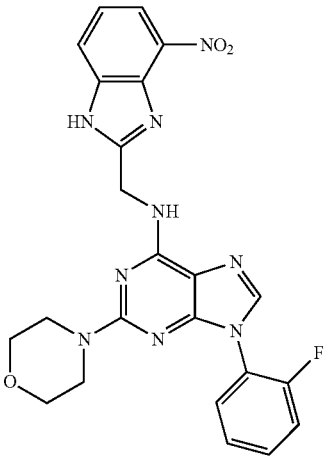 [SMILES: O=[N+]([O-])c1cccc2[nH]c(CNc3nc(N4CCOCC4)nc4c3ncn4-c3ccccc3F)nc12] |
| SR-2368 | 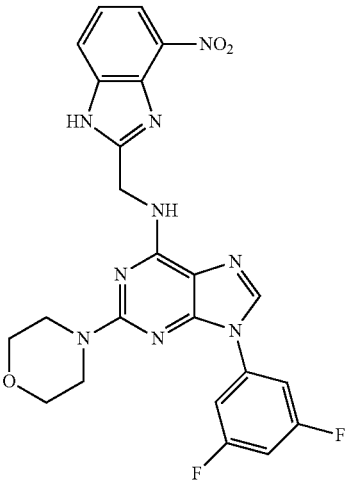 [SMILES: O=[N+]([O-])c1cccc2[nH]c(CNc3nc(N4CCOCC4)nc4c3ncn4-c3cc(F)cc(F)c3)nc12] |
| SR-2797 | 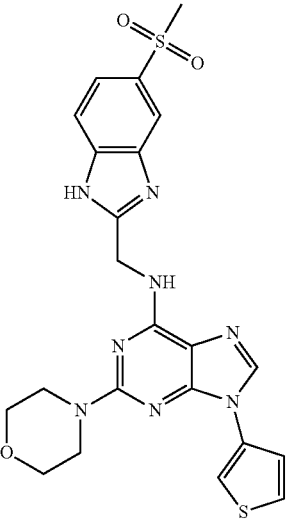 [SMILES: CS(=O)(=O)c1ccc2[nH]c(CNc3nc(N4CCOCC4)nc4c3ncn4-c3ccsc3)nc2c1] |
| SR-2805 | 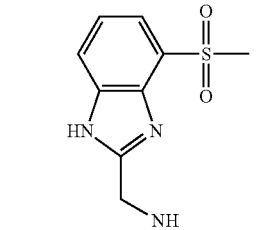 |
| SR-2848 | 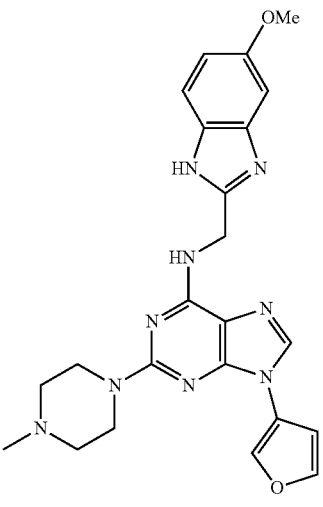 [SMILES: COc1ccc2[nH]c(CNc3nc(N4CCN(C)CC4)nc4c3ncn4-c3ccoc3)nc2c1] |
| SR-2849 | 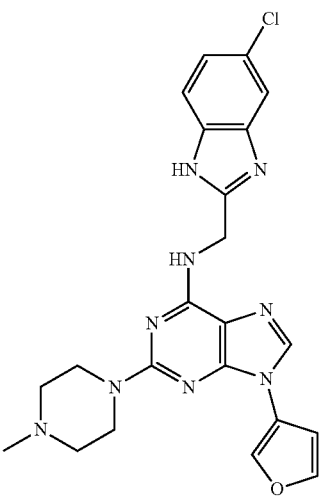 [SMILES: CN1CCN(c2nc(NCc3nc4cc(Cl)ccc4[nH]3)c3ncn(-c4ccoc4)c3n2)CC1] |

TABLE 1-continued
Exemplary Compounds of the Invention
| Compound Number | Structure |
|---|---|
| SR-2850 | 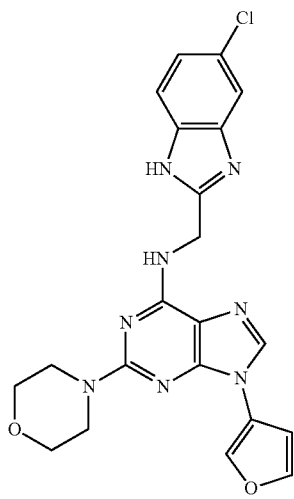 [SMILES: Clc1ccc2[nH]c(CNc3nc(N4CCOCC4)nc4c3ncn4-c3ccoc3)nc2c1] |
| SR-2866 | 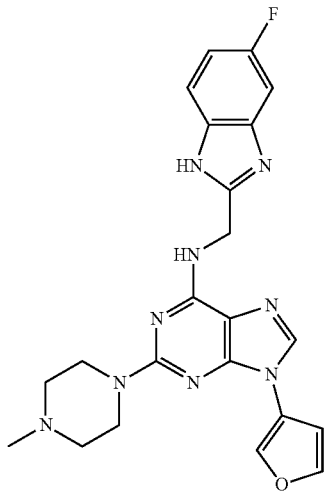 [SMILES: CN1CCN(c2nc(NCc3nc4cc(F)ccc4[nH]3)c3ncn(-c4ccoc4)c3n2)CC1] |
| SR-2867 | 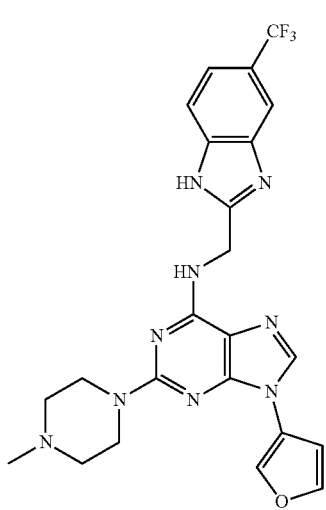 |
| SR-2870 | 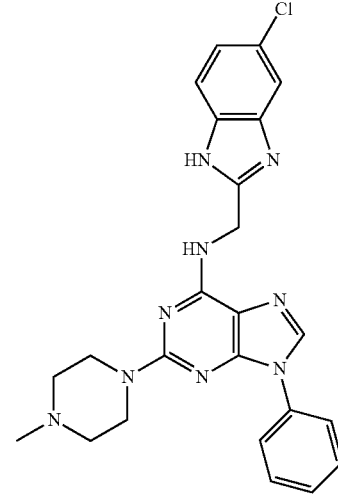 |
| SR-2871 | 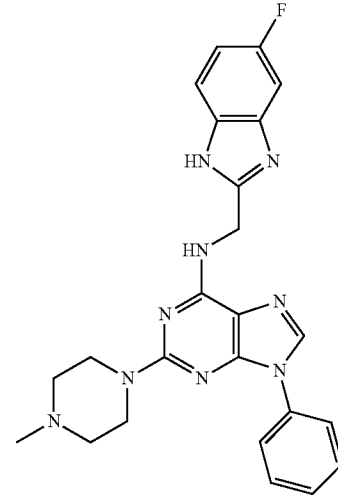 |
| SR-2875 | 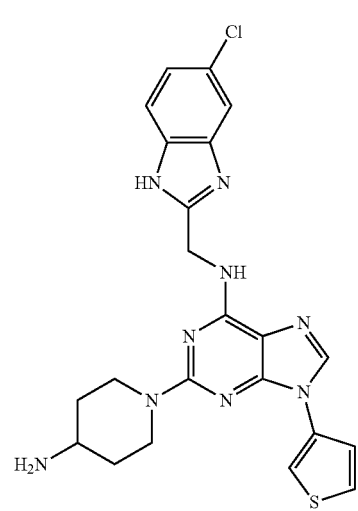 [SMILES: NC1CCN(c2nc(NCc3nc4cc(Cl)ccc4[nH]3)c3ncn(-c4ccsc4)c3n2)CC1] |

TABLE 1-continued

Exemplary Compounds of the Invention

| Compound Number | Structure |
|---|---|
| SR-2876 | 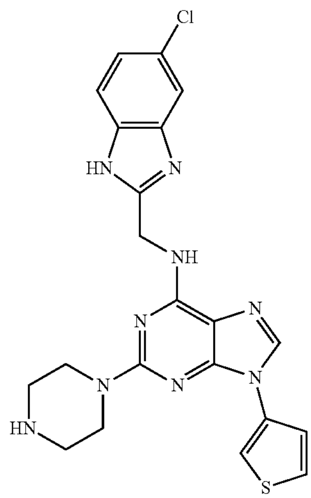 [SMILES: Clc1ccc2[nH]c(CNc3nc(N4CCNCC4)nc4c3ncn4-c3ccsc3)nc2c1] |
| SR-2889 | 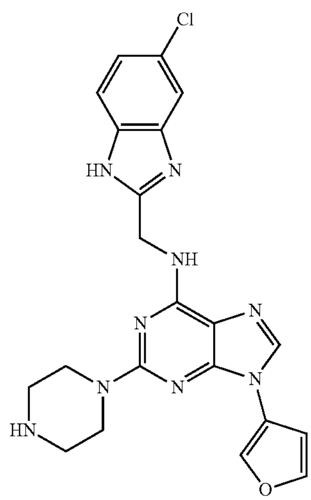 [SMILES: Clc1ccc2[nH]c(CNc3nc(N4CCNCC4)nc4c3ncn4-c3ccoc3)nc2c1] |
| SR-2890 | 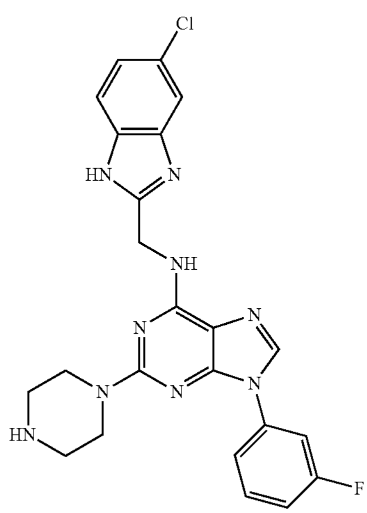 [SMILES: Fc1cccc(-n2cnc3c(NCc4nc5cc(Cl)ccc5[nH]4)nc(N4CCNCC4)nc32)c1] |
| SR-2891 | |
| SR-2914 | |
| SR-2915 | |

TABLE 1-continued

Exemplary Compounds of the Invention

| Compound Number | Structure |
|---|---|
| SR-2916 | 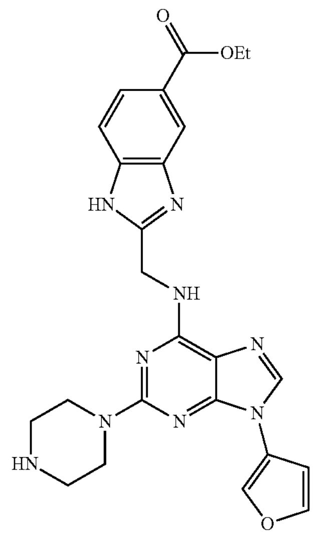 [SMILES: CCOC(=O)c1ccc2[nH]c(CNc3nc(N4CCNCC4)nc4c3ncn4-c3ccoc3)nc2c1] |
| SR-2917 | 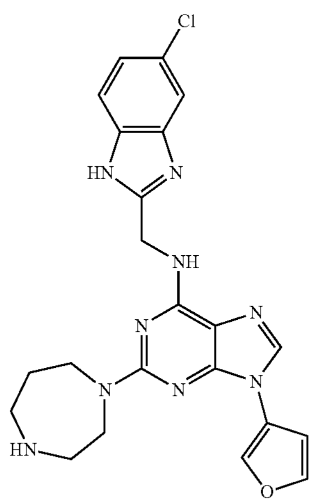 [SMILES: Clc1ccc2[nH]c(CNc3nc(N4CCCNCC4)nc4c3ncn4-c3ccoc3)nc2c1] |
| SR-2927 | 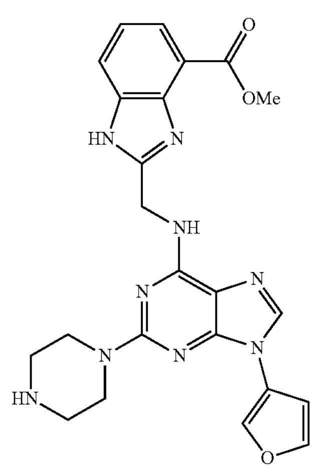 [SMILES: COC(=O)c1cccc2[nH]c(CNc3nc(N4CCNCC4)nc4c3ncn4-c3ccoc3)nc12] |
| SR-2928 | |
| SR-2931 | |
| SR-2932 | |

TABLE 1-continued
Exemplary Compounds of the Invention
| Compound Number | Structure |
|---|---|
| SR-2948 | 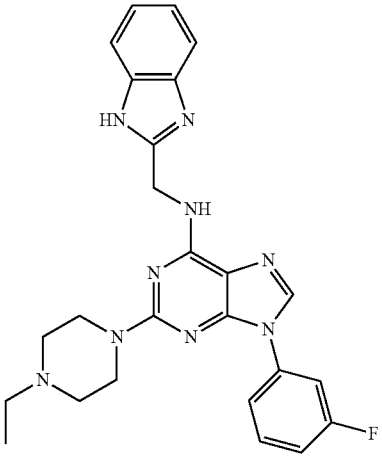 [SMILES: CCN1CCN(c2nc(NCc3nc4ccccc4[nH]3)c3ncn(-c4cccc(F)c4)c3n2)CC1] |
| SR-2949 | 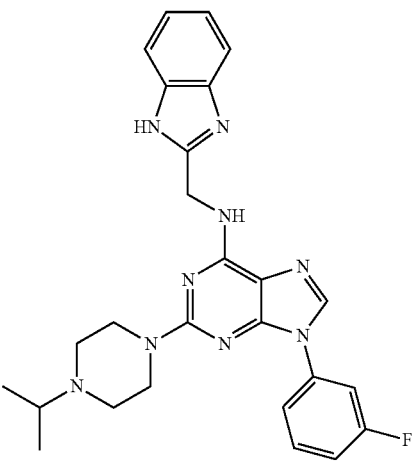 [SMILES: CC(C)N1CCN(c2nc(NCc3nc4ccccc4[nH]3)c3ncn(-c4cccc(F)c4)c3n2)CC1] |
| SR-2950 | 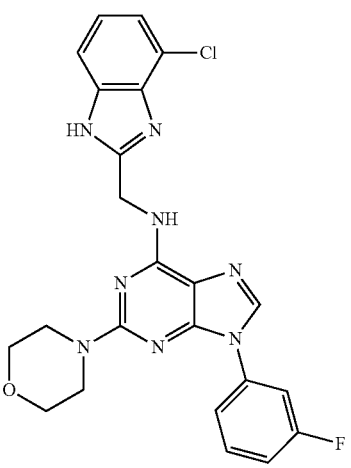 [SMILES: Fc1cccc(-n2cnc3c(NCc4nc5c(Cl)cccc5[nH]4)nc(N4CCOCC4)nc32)c1] |
| SR-3004 | 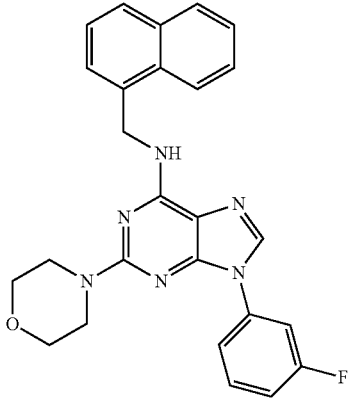 [SMILES: Fc1cccc(-n2cnc3c(NCc4cccc5ccccc45)nc(N4CCOCC4)nc32)c1] |
| SR-3005 | 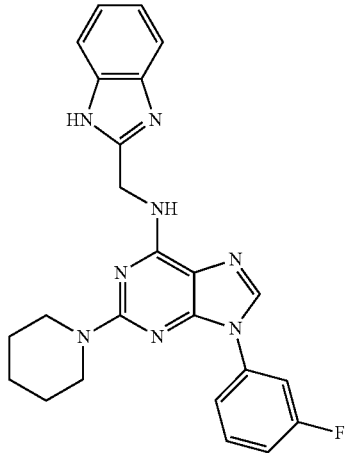 [SMILES: Fc1cccc(-n2cnc3c(NCc4nc5ccccc5[nH]4)nc(N4CCCCC4)nc32)c1] |
| SR-3006 | 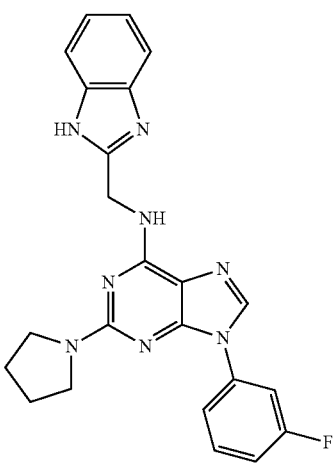 [SMILES: Fc1cccc(-n2cnc3c(NCc4nc5ccccc5[nH]4)nc(N4CCCC4)nc32)c1] |

TABLE 1-continued

Exemplary Compounds of the Invention

| Compound Number | Structure |
|---|---|
| SR-3029 | 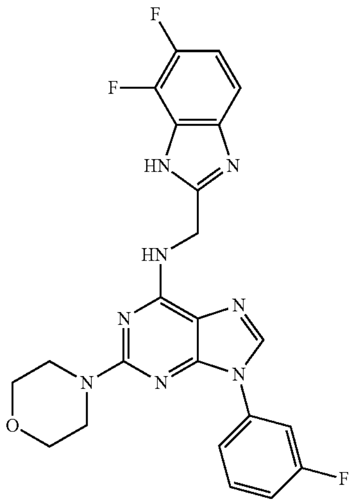 [SMILES: Fc1cccc(-n2cnc3c(NCc4nc5ccc(F)c(F)c5[nH]4)nc(N4CCOCC4)nc32)c1] |
| SR-3048 | 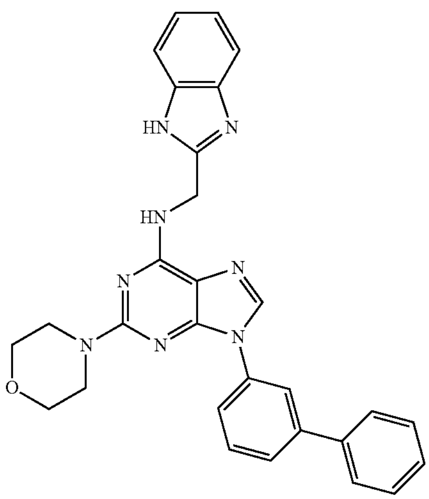 [SMILES: c1ccc(-c2cccc(-n3cnc4c(NCc5nc6ccccc6[nH]5)nc(N5CCOCC5)nc43)c2)cc1] |
| SR-3060 | 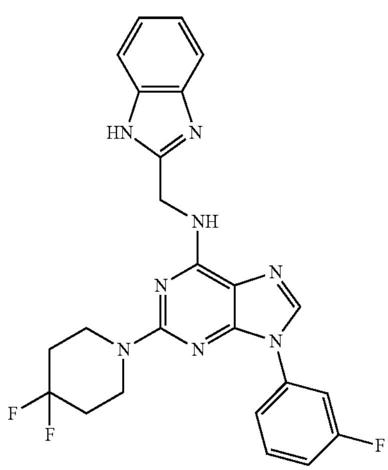 [SMILES: Fc1cccc(-n2cnc3c(NCc4nc5ccccc5[nH]4)nc(N4CCC(F)(F)CC4)nc32)c1] |
| SR-3061 | |
| SR-3084 | |
| SR-3086 | |

TABLE 1-continued
Exemplary Compounds of the Invention
| Compound Number | Structure |
|---|---|
| SR-3087 | 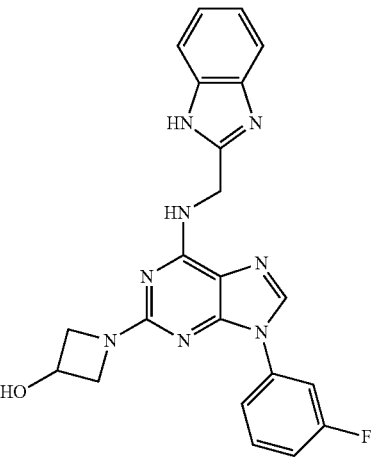 [SMILES: OC1CN(c2nc(NCc3nc4ccccc4[nH]3)c3ncn(-c4cccc(F)c4)c3n2)C1] |
| SR-3095 | 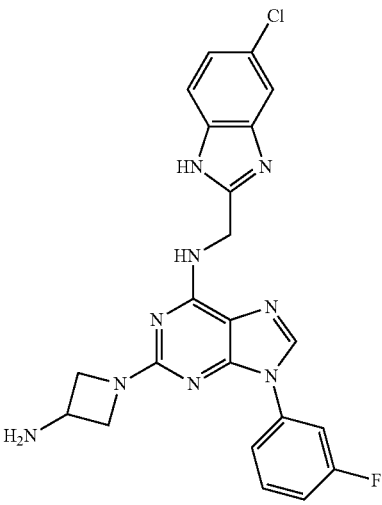 [SMILES: NC1CN(c2nc(NCc3nc4cc(Cl)ccc4[nH]3)c3ncn(-c4cccc(F)c4)c3n2)C1] |
| SR-3096 | 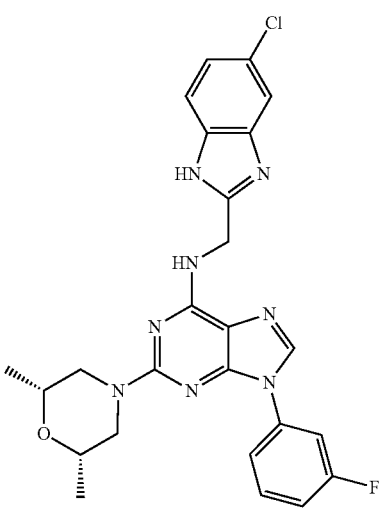 [SMILES: C[C@@H]1CN(c2nc(NCc3nc4cc(Cl)ccc4[nH]3)c3ncn(-c4cccc(F)c4)c3n2)C[C@H](C)O1] |
| SR-3098 | 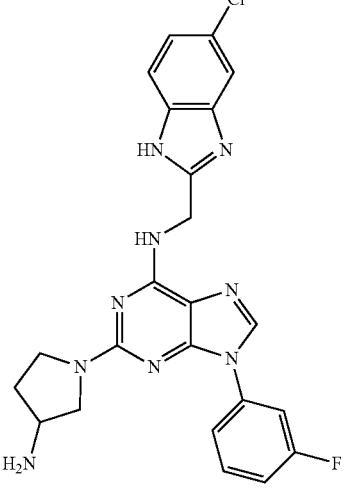 |
| SR-3162 | 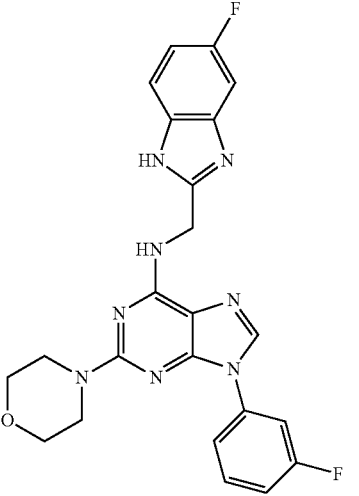 [SMILES: Fc1cccc(-n2cnc3c(NCc4nc5cc(F)ccc5[nH]4)nc(N4CCOCC4)nc32)c1] |
| SR-3163 | 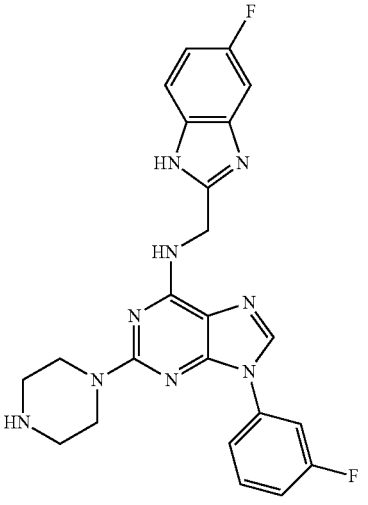 [SMILES: Fc1cccc(-n2cnc3c(NCc4nc5cc(F)ccc5[nH]4)nc(N4CCNCC4)nc32)c1] |
and any salt, hydrate, prodrug, and metabolite thereof.

It is within ordinary skill to evaluate any compound disclosed and claimed herein for effectiveness in inhibition of degradation of Wee1 and in the various cellular assays using the procedures described above or found in the scientific literature. Accordingly, the person of ordinary skill can prepare and evaluate any of the claimed compounds without undue experimentation.

Any compound found to be an effective inhibitor of Wee1 degradation can likewise be tested in animal models and in human clinical studies using the skill and experience of the investigator to guide the selection of dosages and treatment regimens.

Pharmaceutical Methods and Uses

"Treating" or "treatment" within the meaning herein refers to an alleviation of symptoms associated with a disorder or disease, or inhibition of further progression or worsening of those symptoms, or prevention or prophylaxis of the disease or disorder. Similarly, as used herein, an "effective amount" or a "therapeutically effective amount" of a compound of the invention refers to an amount of the compound that alleviates, in whole or in part, symptoms associated with the disorder or condition, or halts or slows further progression or worsening of those symptoms, or prevents or provides prophylaxis for the disorder or condition. In particular, a "therapeutically effective amount" refers to an amount effective, at dosages and for periods of time necessary, to achieve the desired therapeutic result. A therapeutically effective amount is also one in which any toxic or detrimental effects of compounds of the invention are outweighed by the therapeutically beneficial effects.

Another aspect of an embodiment of the invention provides compositions of the compounds of the invention, alone or in combination with another medicament. As set forth herein, compounds of the invention include stereoisomers, tautomers, solvates, prodrugs, pharmaceutically acceptable salts and mixtures thereof. Compositions containing a compound of the invention can be prepared by conventional techniques, e.g. as described in Remington: *The Science and Practice of Pharmacy,* 19th Ed., 1995, incorporated by reference herein. The compositions can appear in conventional forms, for example capsules, tablets, aerosols, solutions, suspensions or topical applications.

Typical compositions include a compound of the invention and a pharmaceutically acceptable excipient which can be a carrier or a diluent. For example, the active compound will usually be mixed with a carrier, or diluted by a carrier, or enclosed within a carrier which can be in the form of an ampoule, capsule, sachet, paper, or other container. When the active compound is mixed with a carrier, or when the carrier serves as a diluent, it can be solid, semi-solid, or liquid material that acts as a vehicle, excipient, or medium for the active compound. The active compound can be adsorbed on a granular solid carrier, for example contained in a sachet. Some examples of suitable carriers are water, salt solutions, alcohols, polyethylene glycols, polyhydroxyethoxylated castor oil, peanut oil, olive oil, gelatin, lactose, terra alba, sucrose, dextrin, magnesium carbonate, sugar, cyclodextrin, amylose, magnesium stearate, talc, gelatin, agar, pectin, acacia, stearic acid or lower alkyl ethers of cellulose, silicic acid, fatty acids, fatty acid amines, fatty acid monoglycerides and diglycerides, pentaerythritol fatty acid esters, polyoxyethylene, hydroxymethylcellulose and polyvinylpyrrolidone. Similarly, the carrier or diluent can include any sustained release material known in the art, such as glyceryl mono stearate or glyceryl distearate, alone or mixed with a wax.

The formulations can be mixed with auxiliary agents which do not deleteriously react with the active compounds. Such additives can include wetting agents, emulsifying and suspending agents, salt for influencing osmotic pressure, buffers and/or coloring substances, preserving agents, sweetening agents or flavoring agents. The compositions can also be sterilized if desired.

The route of administration can be any route which effectively transports the active compound of the invention to the appropriate or desired site of action, such as oral, nasal, pulmonary, buccal, subdermal, intradermal, transdermal or parenteral, e.g., rectal, depot, subcutaneous, intravenous, intraurethral, intramuscular, intranasal, ophthalmic solution or an ointment, the oral route being preferred.

If a solid carrier is used for oral administration, the preparation can be tabletted, placed in a hard gelatin capsule in powder or pellet form or it can be in the form of a troche or lozenge. If a liquid carrier is used, the preparation can be in the form of a syrup, emulsion, soft gelatin capsule or sterile injectable liquid such as an aqueous or non-aqueous liquid suspension or solution.

Injectable dosage forms generally include aqueous suspensions or oil suspensions which can be prepared using a suitable dispersant or wetting agent and a suspending agent Injectable forms can be in solution phase or in the form of a suspension, which is prepared with a solvent or diluent. Acceptable solvents or vehicles include sterilized water, Ringer's solution, or an isotonic aqueous saline solution. Alternatively, sterile oils can be employed as solvents or suspending agents. Preferably, the oil or fatty acid is non-volatile, including natural or synthetic oils, fatty acids, mono-, di- or tri-glycerides.

For injection, the formulation can also be a powder suitable for reconstitution with an appropriate solution as described above. Examples of these include, but are not limited to, freeze dried, rotary dried or spray dried powders, amorphous powders, granules, precipitates, or particulates. For injection, the formulations can optionally contain stabilizers, pH modifiers, surfactants, bioavailability modifiers and combinations of these. The compounds can be formulated for parenteral administration by injection such as by bolus injection or continuous infusion. A unit dosage form for injection can be in ampoules or in multi-dose containers.

The formulations of the invention can be designed to provide quick, sustained, or delayed release of the active ingredient after administration to the patient by employing procedures well known in the art. Thus, the formulations can also be formulated for controlled release or for slow release.

Compositions contemplated by the present invention can include, for example, micelles or liposomes, or some other encapsulated form, or can be administered in an extended release form to provide a prolonged storage and/or delivery effect. Therefore, the formulations can be compressed into pellets or cylinders and implanted intramuscularly or subcutaneously as depot injections. Such implants can employ known inert materials such as silicones and biodegradable polymers, e.g., polylactide-polyglycolide. Examples of other biodegradable polymers include poly(orthoesters) and poly(anhydrides).

For nasal administration, the preparation can contain a compound of the invention, dissolved or suspended in a liquid carrier, preferably an aqueous carrier, for aerosol application. The carrier can contain additives such as solubilizing agents, e.g., propylene glycol, surfactants, absorption enhancers such as lecithin (phosphatidylcholine) or cyclodextrin, or preservatives such as parabens.

For parenteral application, particularly suitable are injectable solutions or suspensions, preferably aqueous solutions with the active compound dissolved in polyhydroxylated castor oil.

Tablets, dragees, or capsules having talc and/or a carbohydrate carrier or binder or the like are particularly suitable for oral application. Preferable carriers for tablets, dragees, or capsules include lactose, corn starch, and/or potato starch. A syrup or elixir can be used in cases where a sweetened vehicle can be employed.

A typical tablet that can be prepared by conventional tabletting techniques can contain:

| Core: | |
|---|---|
| Active compound (as free compound or salt thereof) | 250 mg |
| Colloidal silicon dioxide (Aerosil) ® | 1.5 mg |
| Cellulose, microcryst. (Avicel) ® | 70 mg |
| Modified cellulose gum (Ac-Di-Sol) ® | 7.5 mg |
| Magnesium stearate | Ad. |
| Coating: | |
| HPMC approx. | 9 mg |
| *Mywacett 9-40 T approx. | 0.9 mg |

*Acylated monoglyceride as plasticizer for film coating.

A typical capsule for oral administration contains compounds of the invention (250 mg), lactose (75 mg) and magnesium stearate (15 mg). The mixture is passed through a 60 mesh sieve and packed into a No. 1 gelatin capsule. A typical injectable preparation is produced by aseptically placing 250 mg of compounds of the invention into a vial, aseptically freeze-drying and sealing. For use, the contents of the vial are mixed with 2 mL of sterile physiological saline, to produce an injectable preparation.

The compounds of the invention can be administered to a human in need of such treatment, prevention, elimination, alleviation or amelioration of a malcondition that is mediated through the inhibition of the degradation of Wee1, for example cancer, Alzheimer's, and other malconditions, including: neurological disorders, psychiatric disorders, and inflammation-related disorders.

The compounds of the invention are effective over a wide dosage range. For example, in the treatment of adult humans, dosages from about 0.05 to about 5000 mg, preferably from about 1 to about 2000 mg, and more preferably between about 2 and about 2000 mg per day can be used. A typical dosage is about 10 mg to about 1000 mg per day. In choosing a regimen for patients it can frequently be necessary to begin with a higher dosage and when the condition is under control to reduce the dosage. The exact dosage will depend upon the activity of the compound, mode of administration, on the therapy desired, form in which administered, the subject to be treated and the body weight of the subject to be treated, and the preference and experience of the physician or veterinarian in charge.

Generally, the compounds of the invention are dispensed in unit dosage form including from about 0.05 mg to about 1000 mg of active ingredient together with a pharmaceutically acceptable carrier per unit dosage.

Usually, dosage forms suitable for oral, nasal, pulmonal or transdermal administration include from about 125 µg to about 1250 mg, preferably from about 250 µg to about 500 mg, and more preferably from about 2.5 mg to about 250 mg, of the compounds admixed with a pharmaceutically acceptable carrier or diluent.

Dosage forms can be administered daily, or more than once a day, such as twice or thrice daily. Alternatively dosage forms can be administered less frequently than daily, such as every other day, or weekly, if found to be advisable by a prescribing physician.

An embodiment of the invention also encompasses prodrugs of a compound of the invention which on administration undergo chemical conversion by metabolic or other physiological processes before becoming active pharmacological substances. Conversion by metabolic or other physiological processes includes without limitation enzymatic (e.g, specific enzymatically catalyzed) and non-enzymatic (e.g., general or specific acid or base induced) chemical transformation of the prodrug into the active pharmacological substance. In general, such prodrugs will be functional derivatives of a compound of the invention which are readily convertible in vivo into a compound of the invention. Conventional procedures for the selection and preparation of suitable prodrug derivatives are described, for example, in Design of Prodrugs, ed. H. Bundgaard, Elsevier, 1985.

In another embodiment, there are provided methods of making a composition of a compound described herein including formulating a compound of the invention with a pharmaceutically acceptable carrier or diluent. In some embodiments, the pharmaceutically acceptable carrier or diluent is suitable for oral administration. In some such embodiments, the methods can further include the step of formulating the composition into a tablet or capsule. In other embodiments, the pharmaceutically acceptable carrier or diluent is suitable for parenteral administration. In some such embodiments, the methods further include the step of lyophilizing the composition to form a lyophilized preparation.

CNS neurogenesis requires Cdk1 activity regulated by the phosphatase Cdc25 and the tyrosine kinase Wee1[1]. Cdk1 activity decreases in normal adult neurons and is reactivated in neurological diseases such as Alzheimer's[2]. A major mechanism controlling Cdk1 activity in neurons is Wee1 degradation via the ubiquitin proteasome pathway[3]. It was sought to identify pathways controlling neuronal Wee1 degradation using cerebellar granule cells and a reporter of Wee1 turnover, K328M-Wee1-Luciferase[4]. A selective small molecule inhibitor of Wee1 degradation was identified, compound SR-653234. Characterization of SR-653234 demonstrated that it selectively inhibits CK1δ with an IC50 of 161 nM. Although previously described CK1δ and CK1ε inhibitors also target Cdk1[5], SR-653234 does not show any appreciable activity toward any cyclin dependent kinases tested, suggesting that CK1δ controls Wee1 degradation. SR-653234 optimization yielded the more selective CK1δ and CK1ε inhibitor, SR-1277. Correspondingly, SR-1277 inhibits Wee1 degradation and cerebellar granule cell proliferation more potently than SR-653234. These exemplary compounds uncovered a novel mechanism through which CK1δ and CK1ε regulates cell cycle transit.

Figures 5, 6:
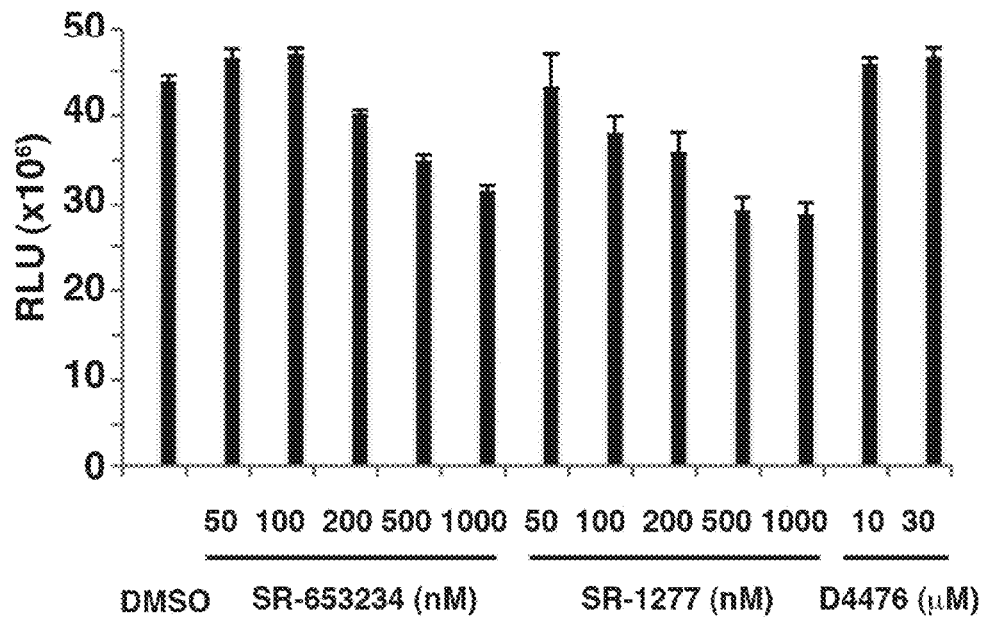
FIG. 5 is a bar graph of cell viability versus SR-653234 and SR-1277 concentration.
FIG. 6 is a chart of IC50s for SR-653234 and SR-1277 relative to staurosporine in FLT3, CK1δ, and CK1ε activity measurements.

Wee1 inhibits Cdk1/cyclin B1 before the G2/M transition by phosphorylating tyrosine 15 on Cdk1[8]. Wee1 is degraded during G2 and mitosis, thus tipping the balance to active Cdc25, which removes tyrosine phosphorylation on Cdk1[9-13]. Wee1 degradation is initiated via Cdk1, Plk1, and CK2 phosphorylation of its N-terminal domain, which induces interaction with an SCF ubiquitin ligase containing β-trcp[14,15]. However, there likely are other Wee1 domains and potentially other kinases controlling its turnover since an N-terminal deletion of Wee1 is rapidly turned over[4]. A chemical biology approach to uncover kinases controlling Wee1 proteolysis was utilized by identifying small molecule inhibitors stabilizing a reporter of Wee1 degradation, K328M-Wee1-luciferase[4]. A 16,000 compound kinase directed library was incubated with K328M-Wee1-luciferase expressing cells, identifying several structurally related members of a purine scaffold that increased the steady-state levels of K328M-Wee1-luciferase (FIG. 1). By contrast, this class did not affect the levels of another protein turned over via the proteasome, N-cyclin B-luciferase[16], suggesting that these compounds specifically inhibited K328M-Wee1-luciferase turnover (FIG. 1). The most potent of these particular compounds, SR-653234 inhibited degradation of K328M-Wee1-luciferase and not luciferase alone, without affecting cell viability (FIG. 5). It also increased the steady-state levels of endogenous Wee1, suggesting that it regulates Wee1 turnover (FIG. 1). Given the known kinase inhibition mediated by similar purine compounds[17], it was postulated that SR-653234 targeted a kinase required for Wee1 degradation.

SR-653234 is a potent inhibitor of CK1δ and CK1ε, LKB1 and FLT3 as judged by measuring the activities of a panel of kinases in the presence of SR-653234 (relative to DMSO control or to the highly promiscuous kinase inhibitor staurosporine; FIG. 2, FIG. 6). Dose response measurements of kinases that were inhibited by SR-653234 by 65% or more were performed in single dose measurements and determined that the IC50s for inhibiting LKB1, FLT3, CK1δ and CK1ε were 92, 161, 540, and 100 nM respectively (FIG. 2; FIG. 6). Furthermore, SR-653234 is a more active inhibitor of CK1δ and CK1ε than the broad-spectrum kinase inhibitor staurosporine. By contrast, staurosporine was a more potent inhibitor of FLT3 activity than SR-653234 (FIG. 6). These Examples suggested that SR-653234 mediated stabilization of Wee1 is due to inhibition of LKB1, FLT3, CK1δ, and/or CK1ε activities.

SR-653234 optimization suggested that CK1δ and/or CK1ε control Wee1 degradation. To distinguish between LKB1, FLT3, and CK1δ and CK1ε activities, a panel of SR-653234 analogs was generated and their activity was tested against LKB1, FLT3, CK1δ and CK1ε in vitro. As shown in FIG. 2 and FIG. 6, among the analogs tested, SR-1277 was a more potent inhibitor of CK1δ than SR-653234 (CK1δ IC50 of 161 nM for SR-653234 and 49 nM for SR-1277), and a weaker inhibitor of FLT3 and LKB1 (FLT3 IC50 of 100 nM for SR-653234 and 305 nM for SR-1277; SR-1277 was inactive toward LKB1). SR-1277 more potently stabilized K328M-Wee1-luciferase than SR-653234, suggesting that CK1δ and CK1ε activity is responsible for inducing Wee1 degradation (EC50 of 624 nM versus 40 nM). Further, a known inhibitor of CK1δ and CK1ε, D4476[18], also stabilized K328M-Wee1-luciferase while a known FLT3 inhibitor[19] did not (FIG. 7). D4476 is known to have poor cell penetration, consistent with the weak activity for this compound seen in the assay provided in FIG. 7. CK1 dependent control of Wee1 degradation was supported by siRNA mediated depletion of CK1δ and CK1ε which reduced Wee1 degradation (FIG. 3), as well as CK1 binding and phosphorylation of Wee1 (FIG. 8). Collectively, these Examples suggest that SR-653234 and SR-1277 inhibit Wee1 degradation by targeting CK1δ and CK1ε.

Figure 9:
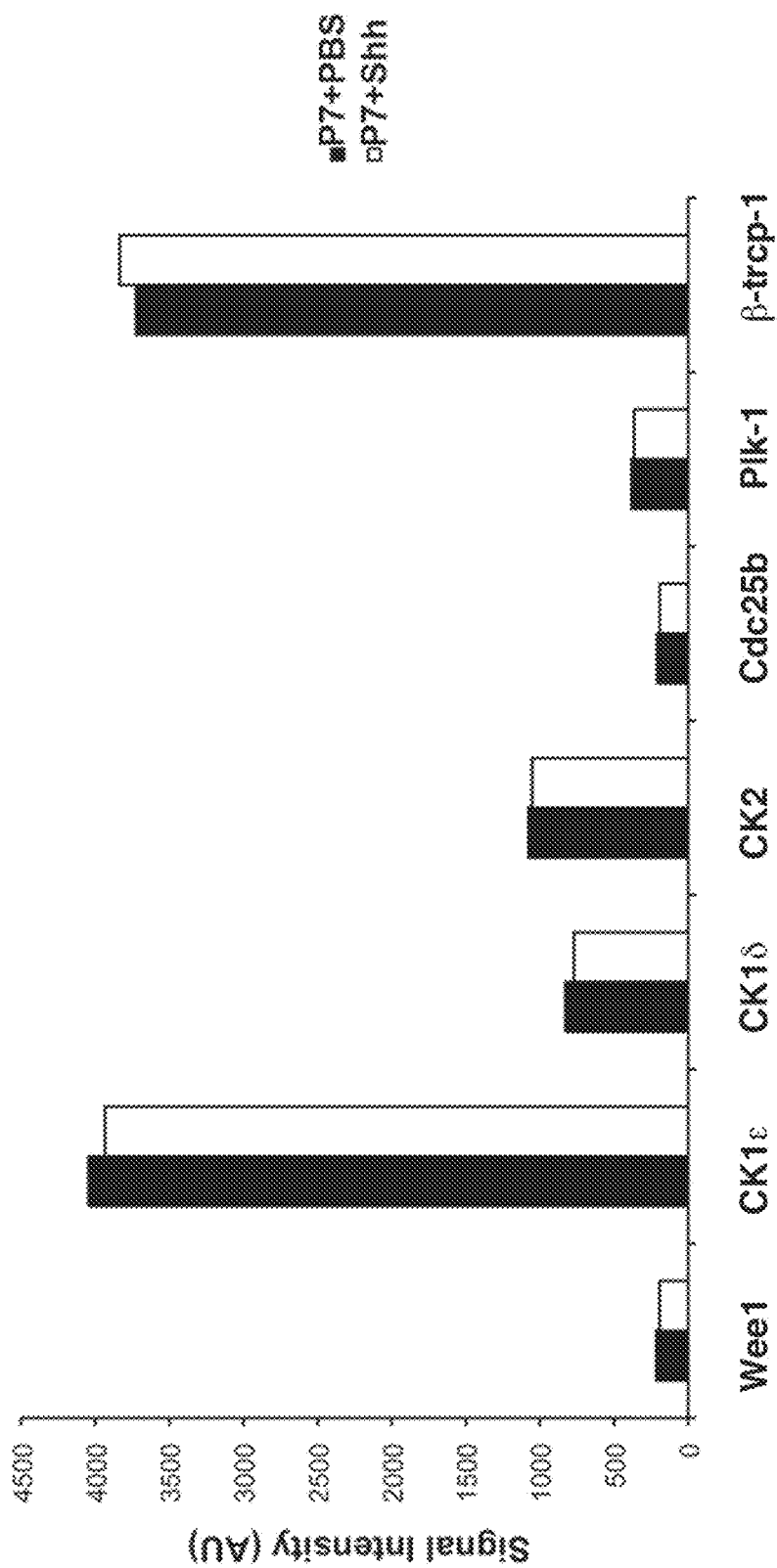
FIG. 9 shows a bar chart of signal intensity of CK1δ, CK1ε, and Wee1, and also CK2, Cdc25b, Plk-1, and β-trcp-1, in GCPs (cerebellar granule cell progenitors) isolated from P7 mice treated with either PBS or Shh.

Since Wee1 degradation is required for cell proliferation, it was tested whether disrupting CK1 activity would inhibit cell cycle transit using mouse cerebellar granule cell progenitors (GCPs), expressing high levels of Wee1 and CK1δ and CK1ε (FIG. 9). During normal brain development, GCPs undergo a remarkable expansion, generating 45 billion granule neurons out of a total of 100 billion neurons in human brain[20]. As this cell population is also thought to transform into medulloblastomas, the most prominent pediatric brain tumor, they provide a model for both normal development and cancer biology[21]. Since it was found that CK1δ and CK1ε are heavily expressed in the early postnatal period when GCPs proliferate rapidly and is upregulated in mouse models of medulloblastoma as well as in human medulloblastoma tumor tissue, it was postulated that it is a potential target for therapeutic intervention in children with medulloblastoma. Measurements of GCP proliferation in both a $^3$H-thymidine uptake assay and an organotypic cell migration assay (FIG. 3; FIG. 10) revealed robust inhibition in the presence of SR-653234 and SR-1277. Although both SR-653234 and SR-1277 inhibited proliferation of GCPs, SR-1277 was 5-10 times more potent as an inhibitor. Given that SR-1277 is more selective than SR-653234 at inhibiting CK1δ and CK1ε in vitro, this suggests that CK1δ and CK1ε activity is required for cerebellar granule cell proliferation. The known CK1δ and CK1ε inhibitor D4476 also inhibited GCP proliferation (FIG. 4B). SR-653234 and SR-1277 treatment induced an S/G2/M arrest (FIG. 11). Thus, CK1δ and CK1ε play an essential cell cycle role, are required for cerebellar granule cell proliferation in vitro and ex vivo, and are putative targets in cancers arising from GCPs.

CK1δ and CK1ε dependent control of cancer cell proliferation may be in part due to differential modulation of substrate degradation. E.g., it may be therapeutically attractive to inhibit CK1 activity and Wee1 degradation since reports demonstrated low Wee1 levels in tumors[22], while limiting Wee1 degradation reduced prostate cancer cell proliferation[23]. CK1 inhibition would enhance rather than limit degradation of the proto-oncogene Skp2[24]. CK1 inhibition would also affect the steady-state levels and activity of multiple proteins implicated in circadian rhythm, cell proliferation, and cancer such as Per-2 and β-catenin[6], and thus it will be important to determine the relative effects of modulating Wee1, Skp2, Per2, or β-catenin stability on cancer cell proliferation.

In addition to cancer, CK1δ and CK1ε dependent control of substrate turnover is important for understanding neurological disease. Although widely expressed, CK1δ and CK1ε mRNA and protein levels are high in the brain and are implicated in dopamine signaling, neurotransmitter release, and neurotransmitter receptor phosphorylation[6]. CK1δ has also been shown to induce tau phosphorylation, thereby initiating microtubule destabilization and neuronal cell death[6,25]. A potential role for CK1 has been described in cleavage of the amyloid precursor protein (APP)[7]. CK1 inhibitors reduced Aβ peptide production by disrupting APP γ-cleavage while constitutively active CK1 increased Aβ peptide production ([7], FIG. 12). Furthermore, CK1 mRNA and protein upregulation in Alzheimer's patients makes CK1 an attractive drug target for the treatment of Alzheimer's disease[7]. Since Wee1 is also present in neurons[3] and misregulated in Alzheimer's disease[26], it will be important to determine whether CK1 dependent regulation of Wee1 turnover contributes to neurological disease progression.

Table 2, below, shows Wee1 degradation activity of some of the compounds of the present invention, along with for some compounds Wee1 stabilization (μM), $IC_{50}$ (μM) for FLT3, and the $IC_{50}$ (μM) for CK1d.

TABLE 2

Wee1 Degradation Activity of Some Compounds of the Present Invention

| Compound Number | % Inhibition, Wee1 Degradation* | Wee1 Stabilization (µM) | IC$_{50}$ (µM) FLT3 | IC$_{50}$ (µM) CK1d |
|---|---|---|---|---|
| SR-1272 | 10.8 | | 0.262$^a$ | 0.128$^a$ |
| SR-1273 | 46.3 | | 0.509$^a$ | 0.013$^a$ |
| SR-1274 | 101.2 | 0.164 | 0.301$^a$ | 0.105$^a$ |
| SR-1275 | 81.4 | | 0.079$^a$ | 0.050$^a$ |
| SR-1276 | 85.9 | | 0.062$^a$ | 0.011$^a$ |
| SR-1277 | 100.0 | 0.040 | 0.305$^a$ | 0.049$^a$ |
| SR-1278 | 18.7 | | 0.240$^a$ | 0.021$^a$ |
| SR-1279 | 79.5 | | 0.014$^a$ | 0.017$^a$ |
| SR-1280 | 48.3 | | 0.975$^a$ | 0.129$^a$ |
| SR-1281 | 22.0 | | | |
| SR-1284 | 111.2 | 0.201 | 28.0$^a$ | 0.815$^a$ |
| SR-1285 | 13.4 | | 4.742$^a$ | 0.522$^a$ |
| SR-1286 | 8.3 | | | |
| SR-1287 | 15.6 | | | |
| SR-1288 | 10.5 | | | |
| SR-1289 | 9.2 | | | |
| SR-1291 | 11.4 | | | |
| SR-1292 | 14.5 | | 0.016$^a$ | 0.003$^a$ |
| SR-1293 | 9.9 | | | |
| SR-1294 | 14.1 | | 0.068$^a$ | 0.011$^a$ |
| SR-1295 | 8.2 | | | |
| SR-1296 | 10.0 | | | |
| SR-1297 | 7.9 | | | |
| SR-1298 | 8.1 | | | |
| SR-1299 | 8.6 | | | |
| SR-1282 | 97.3 | 0.207 | 0.548$^a$ | 0.361$^a$ |
| SR-1283 | 17.0 | | | |
| SR-1289 | 9.2 | | | |
| SR-1401 | 0.0 | | | |
| SR-1402 | 0.0 | | | |
| SR-2149 | 6.1 | | 0.401$^a$ | 0.046$^a$ |
| SR-2001 | 1.7 | | 0.125$^a$ | 0.022$^a$ |
| SR-2007 | 81.1 | | 0.345$^a$ | 0.018$^a$ |
| SR-653234 | 56.8 | 0.624 | 0.100$^a$ | 0.161$^a$ |
| SR-648378 | 4.0 | 4.3 | | |
| SR-648126 | 4.1 | 5.3 | | |
| SR-649967 | 4.0 | 4.3 | | |
| SR-655534 | 3.4 | 3.8 | | |
| SR-656428 | 4.0 | 4.4 | | |
| SR-658807 | 3.6 | 4.1 | | |
| SR-660754 | 5.3 | 4.0 | | |
| SR-660983 | 2.9 | 3.8 | | |
| SR-2007 | | | 0.345$^a$ | 0.019$^a$ |
| SR-2362 | | | | 1.13$^a$ |
| SR-2364 | | | | 0.046$^b$ |
| SR-2366 | | | | 0.114$^b$ |
| SR-2368 | | | | 0.075$^b$ |
| SR-2797 | | | 0.069$^a$ | 0.010$^a$ |
| SR-2805 | | | 0.057$^a$ | 0.016$^a$ |
| SR-2848 | | | 0.298$^a$ | 0.029$^a$ |
| SR-2849 | | | 0.182$^a$ | 0.011$^a$ |
| SR-2850 | | | 0.129$^a$ | 0.023$^a$ |
| SR-2866 | | | 0.216$^a$ | 0.020$^a$ |
| SR-2867 | | | | 0.199$^b$ |
| SR-2870 | | | | 0.828$^b$ |
| SR-2871 | | | | 0.190$^b$ |
| SR-2875 | | | | 0.119$^b$ |
| SR-2876 | | | | 0.051$^b$ |
| SR-2889 | | | 0.082$^a$ | 0.005$^a$ |
| SR-2890 | | | 0.809$^a$ | 0.004$^a$ |
| SR-2891 | | | 0.782$^a$ | 0.011$^a$ |
| SR-2914 | | | | 0.116$^b$ |
| SR-2915 | | | | 0.199$^b$ |
| SR-2916 | | | | 0.687$^b$ |
| SR-2917 | | | | 0.120$^b$ |
| SR-2927 | | | | 0.033$^b$ |
| SR-2928 | | | | 0.107$^b$ |
| SR-2931 | | | | 0.101$^b$ |
| SR-2932 | | | | 0.306$^b$ |
| SR-2948 | | | | 0.589$^b$ |
| SR-2949 | | | | 2.410$^b$ |
| SR-2950 | | | | 0.153$^b$ |
| SR-3004 | | | | 0.666$^b$ |
| SR-3005 | | | | >10$^b$ |
| SR-3006 | | | | 0.884$^b$ |
| SR-3029 | | | | 0.096$^b$ |
| SR-3048 | | | | >10$^b$ |
| SR-3060 | | | | >10$^b$ |
| SR-3061 | | | | 0.199$^b$ |
| SR-3084 | | | | 0.382$^b$ |
| SR-3086 | | | | 0.037$^b$ |
| SR-3087 | | | | 0.482$^b$ |
| SR-3095 | | | | 0.360$^b$ |
| SR-3096 | | | | 0.830$^b$ |
| SR-3098 | | | | 0.150$^b$ |
| SR-3162 | | | | 0.088$^b$ |
| SR-3163 | | | | 0.062$^b$ |

*% Inhibition of Wee1 degradation at 250 nM, reported relative to SR-1277 = 100%
$^a$Inhibition data determined by Reaction Biology Corporation;
$^b$Inhibition data determined from an in-house CK1d assay.

Table 3, below, illustrates the activity of some of the compounds of the present invention in the National Cancer Institute's Dose Growth Inhibition assay against several human tumor cell lines selected from the NCI-60 panel. The GI$_{50}$ data, generated by the NCI, define the concentrations of SR-653234 and SR-1277 that inhibit the growth the several indicated cancer cell lines by 50%.

TABLE 3

Activity of Some Compounds of the Present Invention Against Human Cancer Cell Lines

| Cancer cell lines | GI$_{50}$ data (µM) | | | | | |
|---|---|---|---|---|---|---|
| | SR-653234 | SR-1277 | SR-2849 | SR-2889 | SR-2890 | SR-2891 |
| COLO 205 (colon) | 0.026 | 0.015 | 0.025 | <0.010 | 0.029 | 0.030 |
| SNB-75 (CNS) | 0.025 | <0.010 | 0.019 | <0.010 | 0.046 | 0.024 |
| A498 (renal) | 0.072 | 0.017 | 0.113 | 0.024 | 0.207 | 0.321 |
| RXF393 (renal) | 0.026 | <0.010 | 0.017 | <0.010 | 0.041 | 0.049 |

TABLE 3-continued

Activity of Some Compounds of the Present Invention Against Human Cancer Cell Lines

| Cancer cell lines | GI$_{50}$ data (µM) | | | | | |
| --- | --- | --- | --- | --- | --- | --- |
| | SR-653234 | SR-1277 | SR-2849 | SR-2889 | SR-2890 | SR-2891 |
| MDA-MB-468 (breast) | 0.016 | <0.010 | <0.010 | <0.010 | 0.012 | <0.010 |
| UACC-62 (melanoma) | 0.068 | 0.014 | 0.130 | 0.017 | 0.182 | 0.174 |

FIG. 1 (FIGS. 1A, 1B, 1C, 1D, and 1E) generally illustrate a compound of the present invention (SR-653234) can selectively stabilize Wee1. FIG. 1A illustrates SR-653234 stabilizes Wee1-luciferase but not N-cyclin B1-luciferase. HeLa cells that were transfected with either K328M-Wee1-Luciferase or N-cyclin B1-luciferase were incubated with increasing concentration of SR-653234. The percentage of signal relative to the proteasome inhibitor MG132 is shown. FIG. 1B illustrates the structures of SR-653234 analogs that stabilized K328M-Wee1-Luciferase with the corresponding EC50s for stabilization of K328M-Wee1-luciferase. FIG. 1C illustrates a class of SR-653234 analogs selectively stabilizes endogenous Wee1. A Western blot is shown of endogenous Wee1 or Skp1 (loading control) of HeLa cells incubated with 5 µM of indicated compounds for 24 hours. FIG. 1D illustrates SR-653234 inhibits K328M-Wee1-luciferase degradation. HeLa cells transfected with K328M-Wee1-luciferase were incubated with cycloheximide along with either DMSO or 5 µM SR-653234 and the extent of Wee1 degradation was measured after luminescence detection. The 0 time point was set to 100%. FIG. 1E illustrates SR-653234 does not affect luciferase degradation. HeLa cells were transfected with PGL3 cDNA encoding luciferase, and subsequently incubated with cycloheximide along with DMSO or 5 µM SR-653234. The extent of degradation was measured as in FIG. D.

FIG. 2 (FIGS. 2A, 2B, 2C, and 2D) generally illustrates a compound of the present invention (SR-1277) can inhibit CK1δ and CK1ε more than another specific compound of the invention (SR-653234). FIG. 2A illustrates the structure of SR-1277 and SR-653234. 296 Kinases were profiled for activity in the presence of either SR-653234 or SR-1277 at Reaction Biology Corporation, and both were found to be highly selective for casein kinase among the set of 296 kinases tested. Among these, the most significant "off-target" activity was against FLT-3 (data not shown). FIG. 2B illustrates in vitro kinase activity of CK1δ in the presence of SR-653234 or SR-1277. FIG. 2C illustrates FLT3 kinase activity in the presence of SR-653234 or SR-1277. FIG. 2D illustrates K328M-Wee1-Luciferase stabilization in the presence of SR-653234 or SR-1277. HeLa cells were transfected with either K328M-Wee1-Luciferase or Luciferase alone and incubated with increasing concentration of SR-653234 or SR-1277. Steady-state level of K328M-Wee1-Luciferase (K328M-Wee1-Luc) was divided by Luciferase level (Luc) and plotted.

Figure 3:
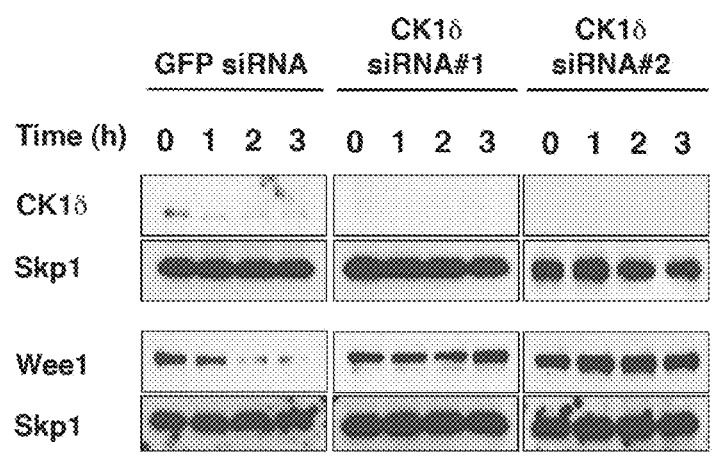
FIG. 3 demonstrates the amount of Wee1 remaining after siRNA mediated depletion of CK1δ

FIG. 3 generally illustrates CK1δ depletion can inhibit Wee1 degradation. HeLa cells were transfected with siRNAs targeting CK1δ or GFP control. HeLa cells depleted of CK1δ or GFP were analyzed for their ability to induce endogenous Wee1 degradation as determined by cycloheximide degradation analysis.

Figure 4A:
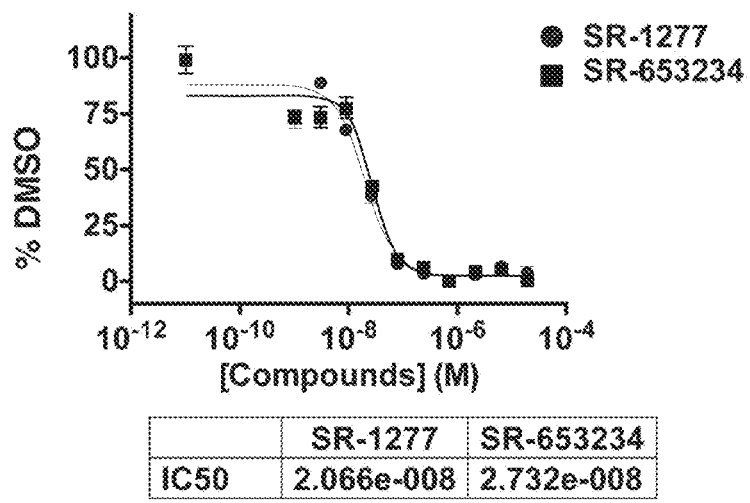
FIG. 4A is a graph of percent control (DMSO) measuring GCP proliferation ($^3$H-thymidine incorporation) versus concentration of SR-653234 or SR-1277.
Figure 4B:
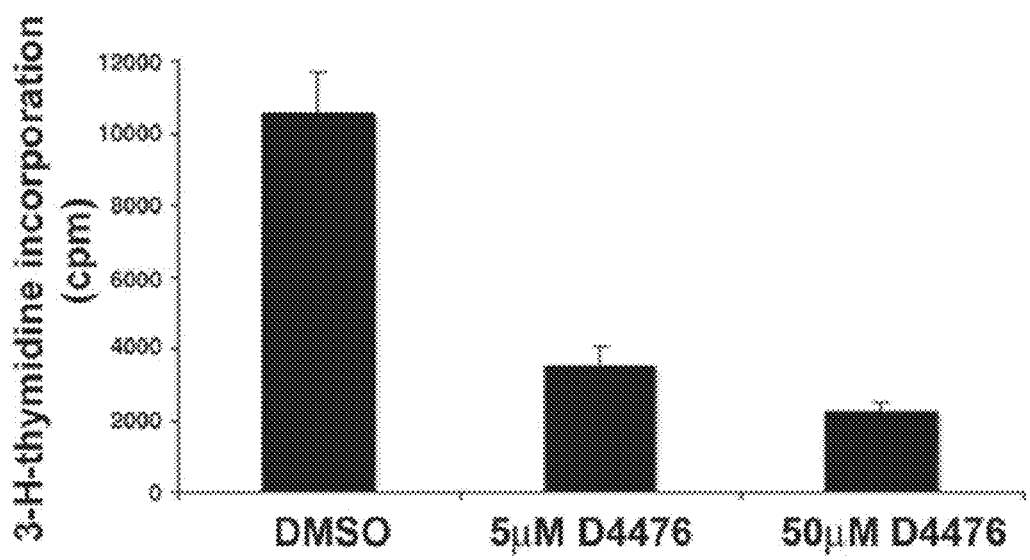
FIG. 4B is a bar graph of $^3$H-thymidine incorporation of GCPs incubated with DMSO, 5 μM D4476, or 50 μM D4476.

FIG. 4 (FIGS. 4A and 4B) generally illustrate CK1 is required for GCP (cerebellar granule cell progenitor) proliferation. FIG. 4A illustrates SR-1277 and SR-653234 inhibit GCP proliferation. $^3$H-thymidine incorporation of GCPs treated with DMSO, SR-653234, or SR-1277 was measured after 24 hours. FIG. 4B illustrates independent confirmation that CK1 inhibition limits GCP proliferation. GCPs were incubated with DMSO, 5 µM D4476 (known CK1δ and CK1ε inhibitor), or 50 µM D4476 and processed for $^3$H-thymidine incorporation after 24 hours. A representative experiment performed in triplicate is shown.

FIG. 5 illustrates cell viability is not affected by specific compounds of the present invention (SR-653234 and SR-1277). Untransfected HeLa cells were incubated for 24 hours with increasing concentrations of SR-653234 and SR-1277 and their viability assessed via an ATP-content measurement method (Cell-Titer Glo, Promega). Variations from DMSO controls (i.e. 100% viability) were not significant as determined by a paired t test. Error bars represent the standard deviation of three separate experiments.

FIG. 6 illustrates compounds of the present invention (SR-653234 and SR-1277) can be more potent CK1δ and CK1ε inhibitors than staurosporine. IC50s (nM) for SR-653234 and SR-1277 relative to staurosporine in FLT3, CK1δ and CK1ε activity measurements. Only LKB1, FLT3, CK1δ and CK1ε activity was affected by SR-653234. SR-1277 was inactive towards LKB1 and less active against FLT3. Compounds were tested in 10-dose IC50 mode with 3-fold serial dilution starting at 50 µM. Control compound Staurosporine (or D4476) was tested in 10-dose IC50 model with 3-fold serial dilution starting at 20 mM. Reactions were carried out at 10 µM ATP. Average and standard deviations of reactions carried out in triplicate are shown.

Figure 7A:
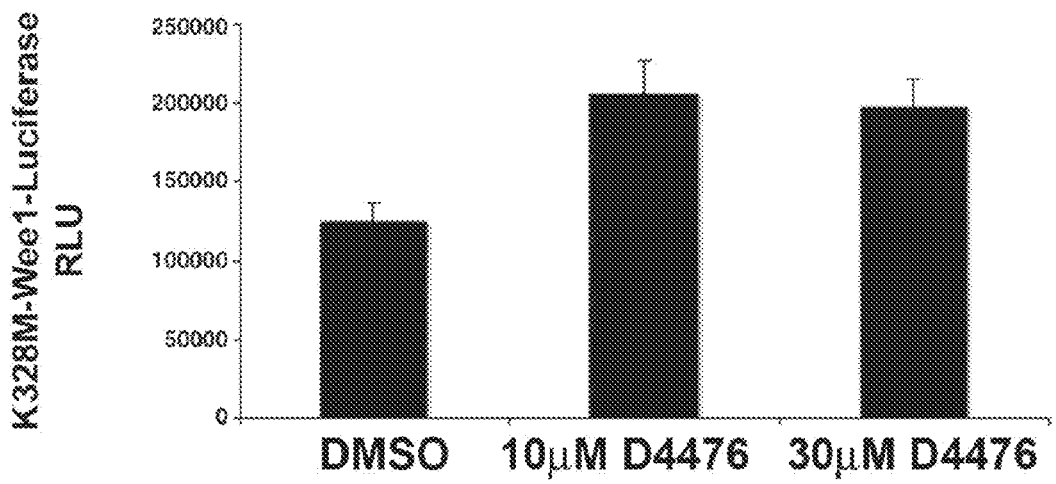
FIG. 7A is a bar chart of K328M-Wee1-Luciferase RLU of DMSO, 10 μM D4476, and 30 μM D4476.
Figure 7B:
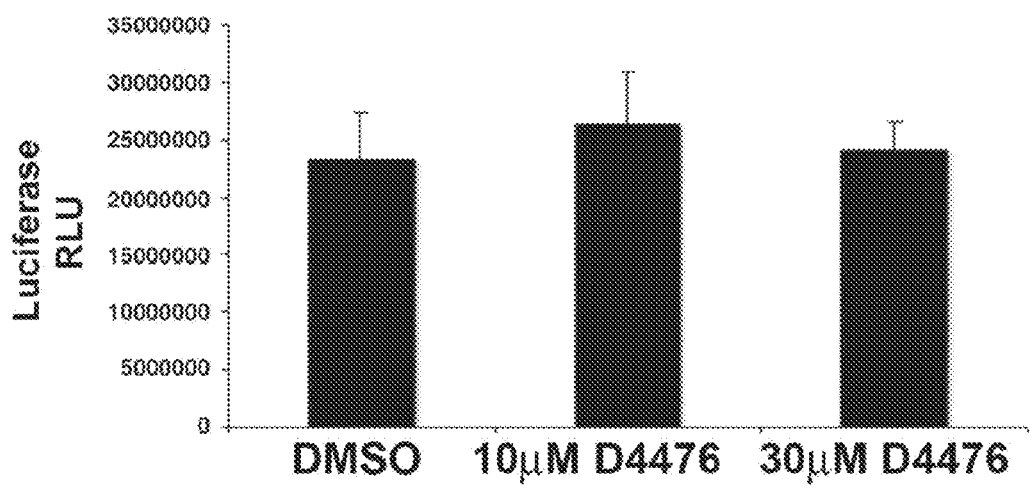
FIG. 7B is a bar chart of Luciferase Vector RLU of DMSO, 10 μM D4476, and 30 μM D4476.
Figure 8:
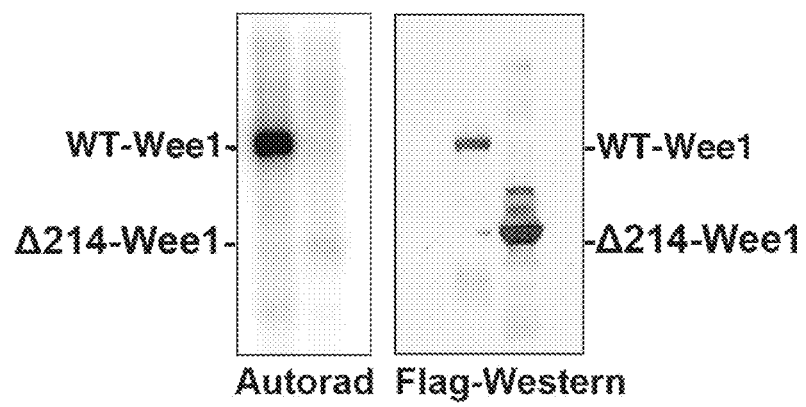
FIG. 8, is an SDS-PAGE with coomassie and autoradiograph of Flag-K328M-Wee1 or Flag Δ214-K328M-Wee1 from transfected 293T cells incubated with CK1δ along with $^{32}$P-ATP.

FIG. 7 (FIG. 7A-D) generally illustrates compounds of the present invention (SR-653234 and SR-1277) can target CK1δ and CK1ε involved in Wee1 degradation. FIG. 7, A, illustrates the known CK1δ and CK1ε inhibitor D4476 stabilizes K328M-Wee1-luciferase. FIG. 7, B, illustrates D4476 does not affect Luciferase levels. FIGS. 7C and 7D, illustrate a known FLT3 inhibitor Sutent does not stabilize K328M-Wee1-luciferase. 5 µM of indicated compounds were incubated with K328M-Wee1-Luciferase or Luciferase expressing HeLa cells and the extent of stabilization measured after adding Brite-lite. MG132 was used as a positive control.

FIG. 8 illustrates CK1 phosphorylates Wee1. Flag-K328M-Wee1 or Flag-Δ214-K328M-Wee1 purified from transfected 293T cells was incubated with CK1δ along with $^{32}$P-ATP and the extent of phosphorylation determined by SDS-PAGE and autoradiography. Flag-K328M-Wee1 migrates below 100 kDa as judged by LC-MSMS FIG. 9 generally illustrates CK1δ and CK1ε and Wee1 are expressed in Cerebellar granule cell progenitors. Levels of CK1δ, CK1ε, and Wee1, or genes previously implicated in Wee1 degradation in GCPs isolated from P7 mice treated with either PBS or Shh, a known GCP mitogen. Affymetrix chip analysis was performed on cells isolated from P7 mice. AU=Arbitrary units.

Figure 10A:
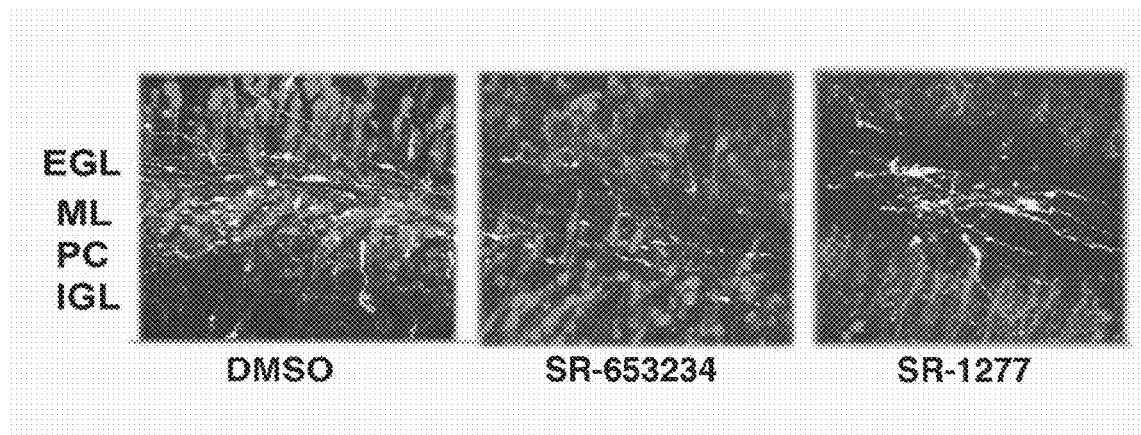
FIG. 10, A, shows images of GCPs in organotypic cerebellar slices treated with DMSO, SR-653234, or SR-1277. EGL refers to external granule layer, ML refers to Molecular Layer, PC refers to Purkinje Cell Layer, and IGL refers to inner granule layer.
Figure 10B:
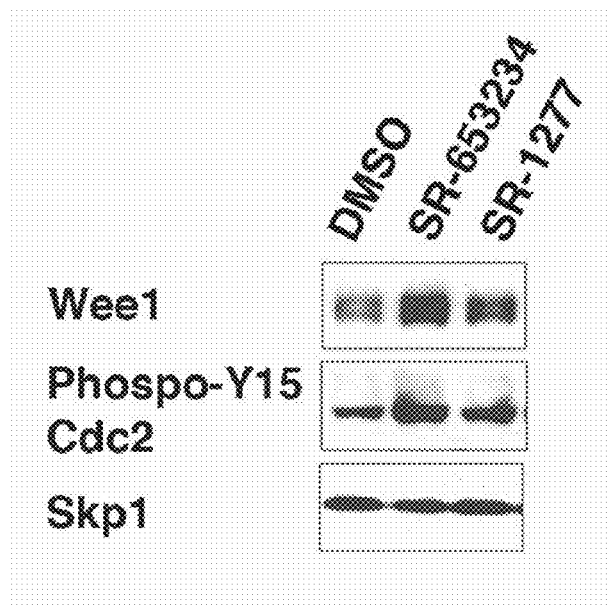
Figure 11:
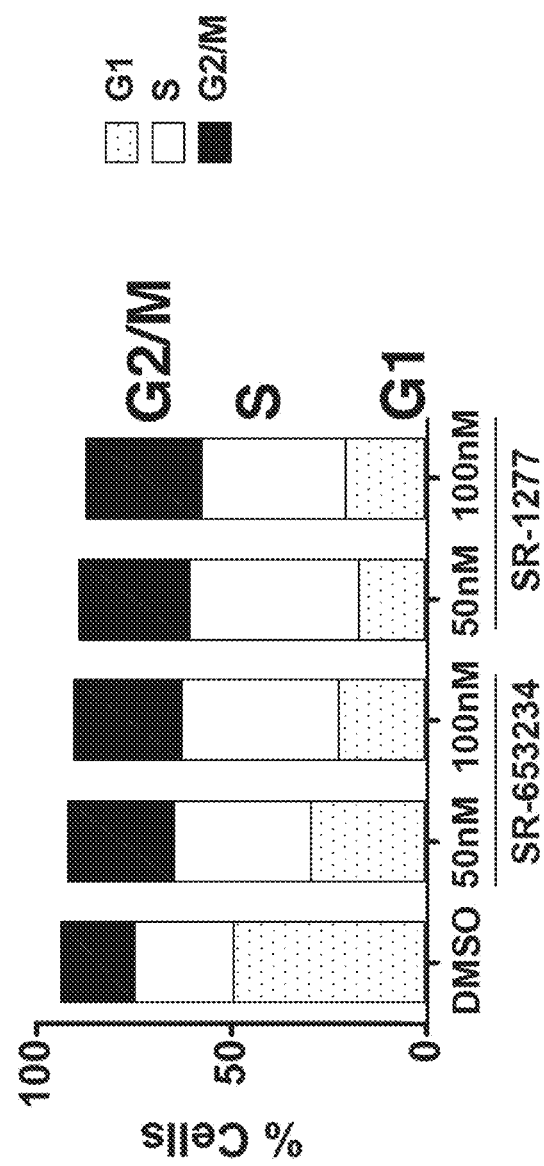
FIG. 11 is PI-FACS analysis of HeLa cells treated with increasing concentrations of SR-653234 or SR-1277.

FIG. 10 (FIGS. 10A and 10B) generally illustrates treatment of organotypic slices with compounds of the present invention (SR-653234 and SR-1277) can inhibit GCP migration. Organotypic cerebellar slices containing Venus expressing GCPs were incubated with DMSO, 500 µM of SR-653234, or SR-1277 for 48 hours and the extent of GCP migration determined relative to the Purkinje cell layer (PCL; labeled in red) with calbindin. FIG. 10A illustrates representative image of GCPs in organotypic cerebellar slices treated with DMSO, SR-653234, or SR-1277. Cerebella from P7 mice were isolated and sliced using a vibratome. Subsequently, slices were electroporated with venus-GFP to visualize GCPs. Slices were then cultured for 48 hours either in the presence of DMSO, SR-653234 (500 nM), or SR-1277 (500 nM), fixed in paraformaldehyde and processed for anti-GFP or calbindin staining to detect either the granule cells or Purkinje Cells. Many GCPs migrate to the Purkinje cell layer in DMSO treated cells, but fewer do so in SR-653234 or SR-1277 treated slices. FIG. 10B illustrates a Wee1 Western blot of purified GCPs treated with DMSO, 10 nM SR-653234, or 10 nM SR-1277 for 24 hours. Phospho-Y15 Cdc2 is a measure of Wee1 activity. Skp-1 is used as a loading control.

FIG. 11 illustrates inhibition of CK1δ and CK1ε can induce an S/G2/M phase arrest. FACS analysis of HeLa cells treated with increasing concentrations of SR-653234 or SR-1277. HeLa cells were treated with indicated concentrations of SR-653234 or SR-1277 for 24 hours and processed for FACS analysis as previously described [26].

Figure 12:
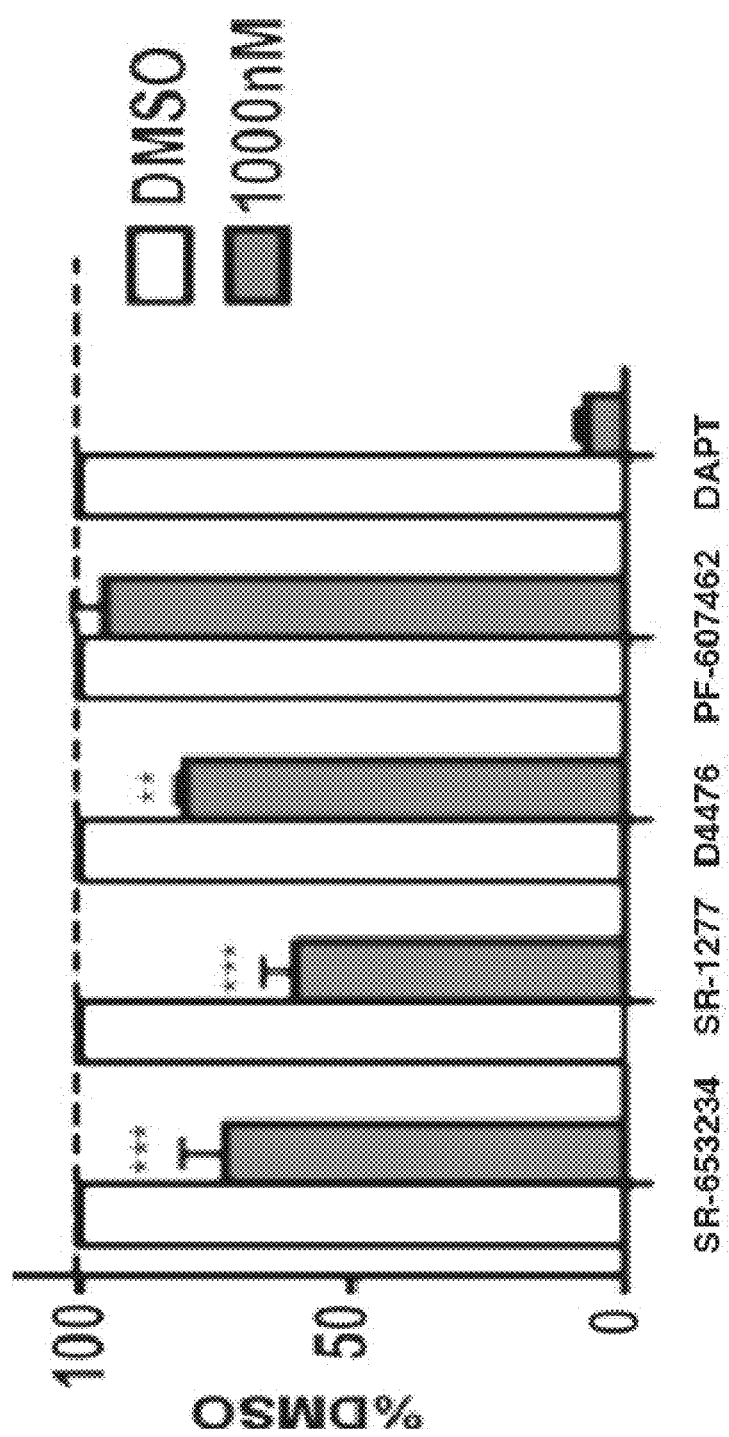
FIG. 12 is a bar chart of concentration of Amyloid β 1-42 from HEK-SW cells treated with DMSO 0.1% or 1 μM of SR-653234, SR-1277, D4476, PF-607462, or DAPT.

FIG. 12 generally illustrates SR-653234 and SR-1277 inhibit Aβ1-42 production. HEK-SW cells, which artificially overexpress mutated APP (K670N/M671L), the so-called Swedish mutation, were cultured on D-MEM supplemented with 10% FBS. HEK-SW cells were kindly provided by laboratory of Dr. Dennis Selkoe. HEK-SW cells were plated in 96 well plates (10,000 cells/well) and at 24 hours post plating replaced media and started treatments. Individual wells (n=3) were treated with DMSO 0.1% or 1 µM of SR-653234, SR-1277, D4476, PF-607462, or DAPT. DAPT, N [(3,5-Difluorophenyl)acetyl]-L-alanyl-2-phenyl]glycine-1,1-dimethylethyl ester, is a known inhibitor of γ-secretase purchased from TOCRIS Bioscience (Ellisville, Mo., USA). Supernatant of cells were collected at 48 hours post plating and concentration of Amyloid β 1-42 (Aβ 1-42) measured by AlphaLISA method (PerkinElmer, Waltham, Mass., USA) following instructions from the company.

Methods:

In vitro kinase assay to detect CK1 or FLT3 activity: CK1 and FLT3 assays as well as complete kinase profile of 296 kinases was performed by Reaction Biology Corporation. For FLT3 20 µM final Abltide was used, sequence: [EAIYAAPFAKKK]. For CK1 (all isoforms) 20 µM CK1 tide was used, sequence: [KRRRAL[pS]VASLPGL] in a standard kinase assay with $^{32}$P-ATP and purified kinase. Incorporation of $^{32}$P-ATP into the peptide was measured after a filter-binding assay. In-house CK1d inhibition assays were performed using a standard homogenous time-resolved fluorescence resonance energy transfer (TR-FRET) format in 50 mM Hepes, pH 7.0, 2.5 mM $MgCl_2$, 0.1 mg/ml bovine serum albumin, 1 mM DL-dithiothreitol, 0.01% Triton X-100 (all from Sigma-Aldrich). Briefly, the CK1δ substrate (DEK<u>T</u>DDE, containing CK1 consensus sequence; 4 µL of a 500 nM stock solution) is labeled with a small Ulight acceptor dye (PerkinElmer). In the presence of 10 µL of 10 nM CK1δ, the Ulight peptide is phosphorylated at a single amino acid that is specifically recognized by a europium chelate (Eu)-labeled phosphospecific antibody. Assays were performed in the presence of 2 µL of compound at different (measured) concentrations, and reactions were stopped by adding 10 µL of 4 nM Eu-anti-p-Topo-IIa (PerkinElmer) in Lance Detection Buffer (Perkin Elmer). Upon excitation of the Eu-labeled antibody, energy is transferred to the acceptor dye resulting in the emission of detected light at 665 nm. Assays are performed under initial velocity conditions where <10% of product is converted to substrate using ATP concentrations twice the Km. Inhibition data obtained in-house was generally in good agreement with data obtained from Reaction Biology Corporation (generally within 2-3 fold). SR-1277 was generally used as a reference control in the biochemical assays.

Wee1-luciferase assay: HeLa cells expressing K328M-Wee1-luciferase or luciferase alone were treated with SR-653234 or SR-1277 for 24-hours after which Brite-lite was added to detect luciferase or K328M-Wee1-luciferase levels. Similar assays have previously been described[4]; PubChem AID 1807.

CK1δ siRNA depletion: HeLa cells were transfected with siRNAs shown to target CK1δ[27] and processed for Wee1 pulse-chase analysis as previously described[28]. Wee1 Western blots were processed as previously described[28].

In vitro proliferation of cerebellar granule cell progenitors (GCPs): Well-established methods for purifying GCPs were developed by the Hatten laboratory[29]. $^3$H-thymidine uptake of purified cells was performed in the presence of DMSO, SR-653234, SR-1277, or D4476 for 24 hours.

NCI-60 Cancer Cell Line Screening was performed by the National Cancer Institute, using the procedures described on their website (http://dtp.nci.nih.gov/branches/btb/ivelsp.html)

REFERENCES

1 Conlon, I. & Raff, M. Size control in animal development. *Cell* 96, 235-244, doi:50092-8674(00)80563-2 [pii] (1999).
2 Husseman, J. W., Nochlin, D. & Vincent, I. Mitotic activation: a convergent mechanism for a cohort of neurodegenerative diseases. *Neurobiol Aging* 21, 815-828, doi:S0197458000002219 [pii] (2000).
3 Muller, M., Lutter, D. & Puschel, A. W. Persistence of the cell-cycle checkpoint kinase Wee1 in SadA- and SadB-deficient neurons disrupts neuronal polarity. *J Cell Sci* 123, 286-294, doi:jcs.058230 [pii]10.1242/jcs.058230 (2010).
4 Owens, L. et al. Activation domain-dependent degradation of somatic Wee1 kinase. *J Biol Chem* 285, 6761-6769, doi:M109.093237 [pii]10.1074/jbc.M109.093237 (2010).
5 Oumata, N. et al. Roscovitine-derived, dual-specificity inhibitors of cyclin-dependent kinases and casein kinases 1. *J Med Chem* 51, 5229-5242, doi:10.1021/jm800109e (2008).
6 Knippschild, U. et al. The casein kinase 1 family: participation in multiple cellular processes in eukaryotes. *Cell Signal* 17, 675-689, doi:S0898-6568(04)00297-9 [pii] 10.1016/j.cellsig.2004.12.011 (2005).
7 Flajolet, M. et al. Regulation of Alzheimer's disease amyloid-beta formation by casein kinase I. *Proc Natl Acad Sci USA* 104, 4159-4164 (2007).

8 Kellogg, D. R. Wee1-dependent mechanisms required for coordination of cell growth and cell division. *J Cell Sci* 116, 4883-4890, doi:10.1242/jcs.00908116244883 [pii] (2003).
9 Watanabe, N., Broome, M. & Hunter, T. Regulation of the human WEE1Hu CDK tyrosine 15-kinase during the cell cycle. *Embo J* 14, 1878-1891 (1995).
10 Michael, W. M. & Newport, J. Coupling of mitosis to the completion of S phase through Cdc34-mediated degradation of Wee1. *Science* 282, 1886-1889 (1998).
11 Gautier, J., Solomon, M. J., Booher, R. N., Bazan, J. F. & Kirschner, M. W. cdc25 is a specific tyrosine phosphatase that directly activates p34cdc2. *Cell* 67, 197-211 (1991).
12 Lu, Z. & Hunter, T. Degradation of activated protein kinases by ubiquitination. *Anna Rev Biochem* 78, 435-475, doi:10.1146/annurev.biochem.013008.092711 (2009).
13 Ayad, N. G. et al. Tome-1, a trigger of mitotic entry, is degraded during G1 via the APC. *Cell* 113, 101-113 (2003).
14 Watanabe, N. et al. M-phase kinases induce phospho-dependent ubiquitination of somatic Wee1 by SCFbeta-TrCP. *Proc Natl Acad Sci USA* 101, 4419-4424 (2004).
15 Watanabe, N. et al. Cyclin-dependent kinase (CDK) phosphorylation destabilizes somatic Wee1 via multiple pathways. *Proc Natl Acad Sci USA* 102, 11663-11668 (2005).
16 Verma, R. et al. Ubistatins inhibit proteasome-dependent degradation by binding the ubiquitin chain. *Science* 306, 117-120 (2004).
17 Haesslein, J. L. & Jullian, N. Recent advances in cyclin-dependent kinase inhibition. Purine-based derivatives as anti-cancer agents. Roles and perspectives for the future. *Curr Top Med Chem* 2, 1037-1050 (2002).
18 Rena, G., Bain, J., Elliott, M. & Cohen, P. D4476, a cell-permeant inhibitor of CK1, suppresses the site-specific phosphorylation and nuclear exclusion of FOXO1a. *EMBO Rep* 5, 60-65, doi:10.1038/sj.embor.7400048[pii] (2004).
19 Arora, A. & Scholar, E. M. Role of tyrosine kinase inhibitors in cancer therapy. *J Pharmacol Exp Ther* 315, 971-979, doi:jpet.105.084145 [pii]10.1124/jpet.105.084145 (2005).
20 Hatten, M. E. & Heintz, N. Mechanisms of neural patterning and specification in the developing cerebellum. *Annu Rev Neurosci* 18, 385-408, doi:10.1146/annurev.ne.18.030195.002125 (1995).
21 Lee, Y. et al. A molecular fingerprint for medulloblastoma. *Cancer Res* 63, 5428-5437 (2003).
22 Yoshida, T., Tanaka, S., Mogi, A., Shitara, Y. & Kuwano, H. The clinical significance of Cyclin B1 and Wee1 expression in non-small-cell lung cancer. *Ann Oncol* 15, 252-256 (2004).
23 Kiviharju-af Hallstrom, T. M. et al. Human prostate epithelium lacks Wee1A-mediated DNA damage-induced checkpoint enforcement. *Proc Natl Acad Sci USA* 104, 7211-7216 (2007).
24 Gao, D. et al. Phosphorylation by Aka promotes cytoplasmic localization of Skp2 and impairs APCCdh1-mediated Skp2 destruction. *Nat Cell Biol* 11, 397-408, doi:ncb1847 [pii]10.1038/ncb1847 (2009).
25 Li, G., Yin, H. & Kuret, J. Casein kinase 1 delta phosphorylates tau and disrupts its binding to microtubules. *J Biol Chem* 279, 15938-15945 (2004).
26 Tomashevski, A., Husseman, J., Jin, L. W., Nochlin, D. & Vincent, I. Constitutive Wee1 activity in adult brain neurons with M phase-type alterations in Alzheimer neurodegeneration. *J Alzheimers Dis* 3, 195-207 (2001).
27 Bryja, V., Schulte, G. & Arenas, E. Wnt-3a utilizes a novel low dose and rapid pathway that does not require casein kinase 1-mediated phosphorylation of Dvl to activate beta-catenin. *Cell Signal* 19, 610-616, doi:S0898-6568(06)00205-1 [pii]10.1016/j.cellsig.2006.08.011 (2007).
28 Smith, A., Simanski, S., Fallahi, M. & Ayad, N. G. Redundant ubiquitin ligase activities regulate wee1 degradation and mitotic entry. *Cell Cycle* 6, 2795-2799 (2007).
29 Hatten, M. E. Neuronal regulation of astroglial morphology and proliferation in vitro. *J Cell Biol* 100, 384-396 (1985).
30 Thompson, M. C. et g. Genomics identifies medulloblastoma subgroups that are enriched for specific genetic alterations. *J Clin Oncol* 24, 1924-1931 (2006).

EXAMPLES

Synthesis of SR-653234

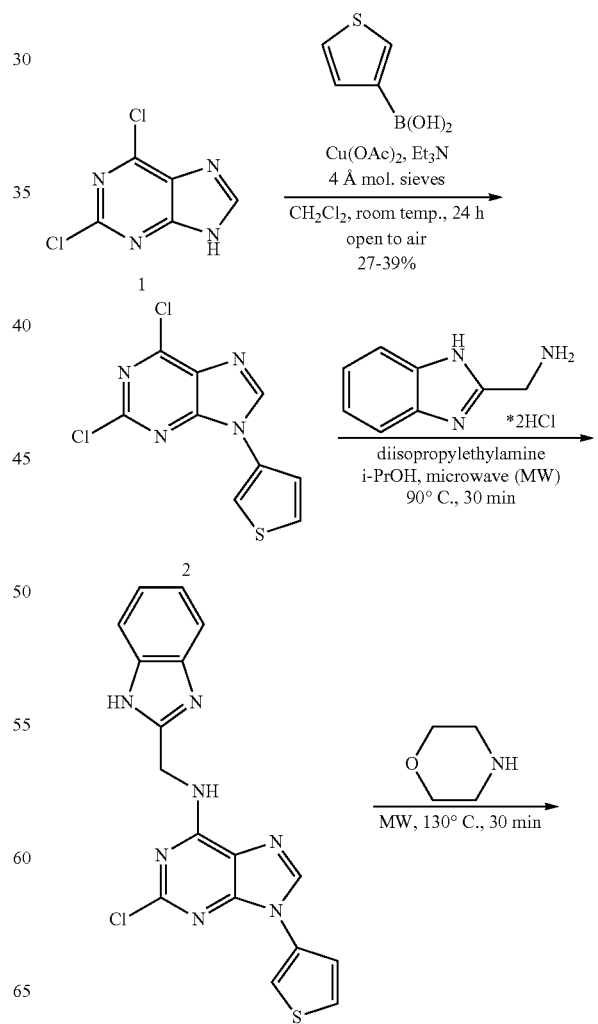

75
-continued
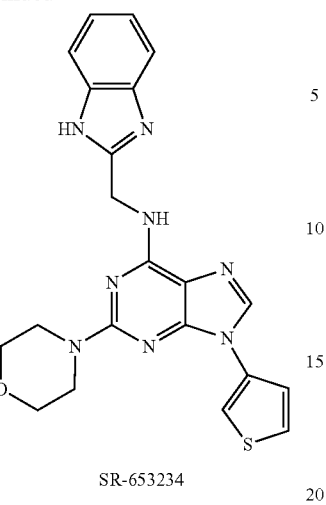
SR-653234
76
-continued
Synthesis of SR-1277:
Synthesis of SR-2890:
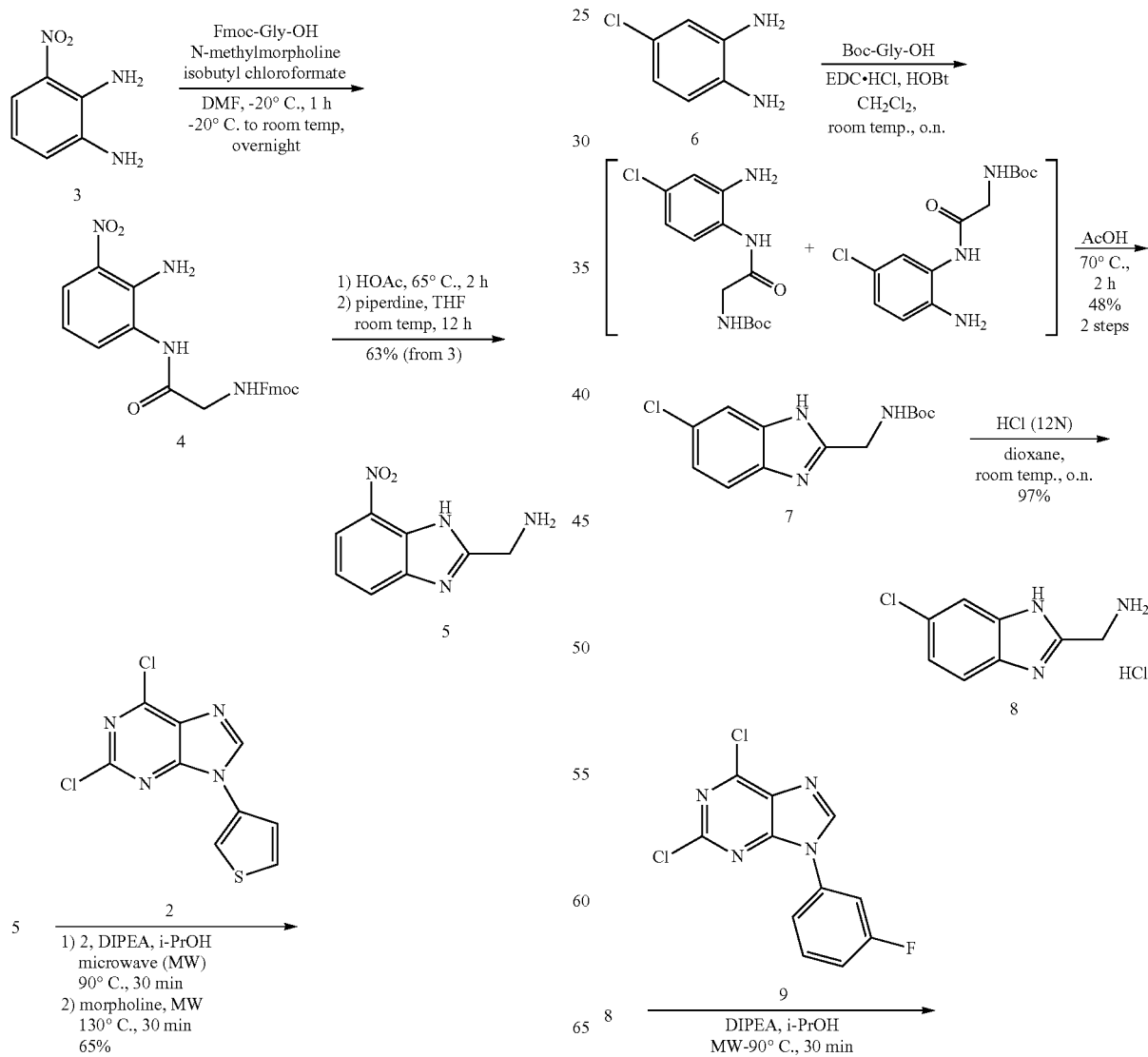

77
-continued
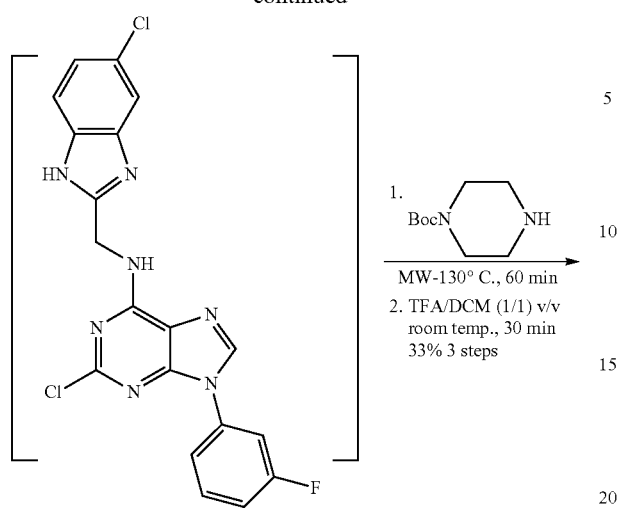
1. BocN piperazine NH
MW-130° C., 60 min
2. TFA/DCM (1/1) v/v
room temp., 30 min
33% 3 steps
SR-2890
Synthesis of SR-3029:
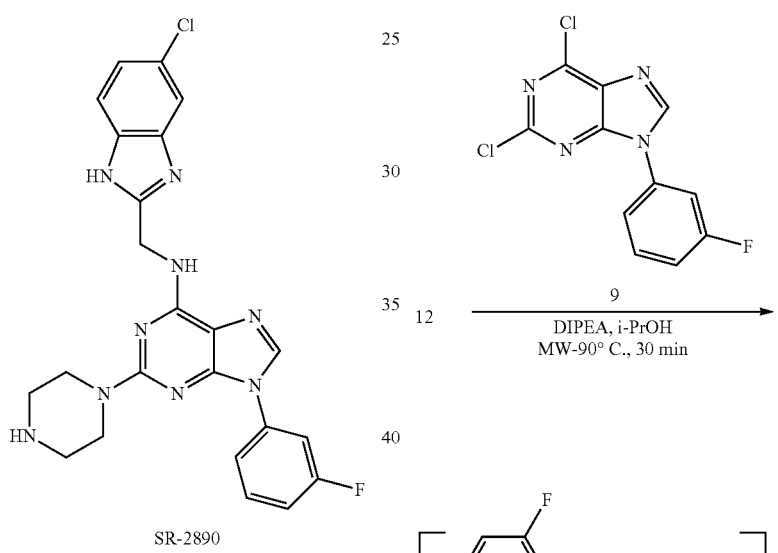
78
-continued
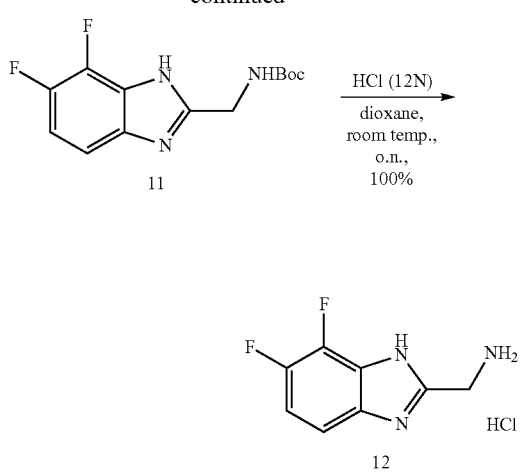
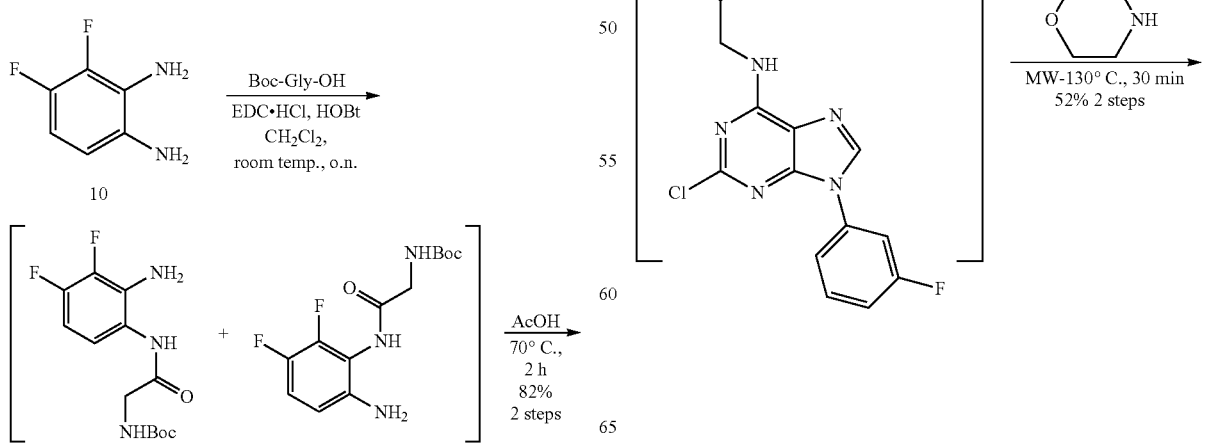

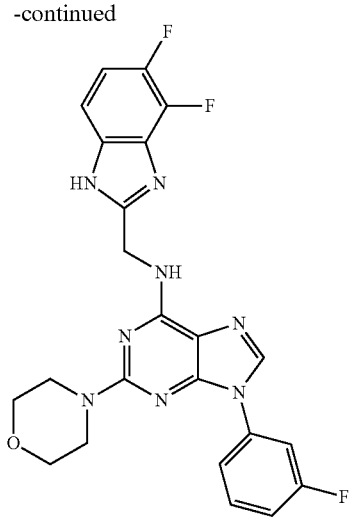

Methods:

All reactions were magnetically stirred, and monitored by thin-layer chromatography using 0.25-mm precoated silica gel Kieselgel 60 $F_{254}$ plates, unless otherwise noted. Visualization of all TLC plates was performed by UV. Product purifications were performed by silica gel flash chromatography (Kieselgel 60; 230-400 mesh) packed in glass columns and eluted with $CH_2Cl_2$/MeOH, or with EtOAcMeOH buffered with 1% $NH_4OH$. Final compound purifications were performed either by silica gel flash chromatography (Kieselgel 60; 230-400 mesh) packed in glass columns and eluted with $CH_2Cl_2$/MeOH, or with EtOAc/MeOH buffered with 1% $NH_4OH$ or by preparative HPLC using SunFire $C_{18}$ OBD 10 μm (30×250 mm) column eluted with $CH_3CN$+ MeOH (1/1, v/v)/$H_2O$+0.1% TFAMaterials: Commercial grade reagents and solvents were used without further purification unless otherwise specified. DMF was dried by passing through a column of activated molecular sieves. N,N-Diisopropylethylamine was distilled under argon from calcium hydride.

Instrumentation:

$^1H$ and $^{13}C$ NMR spectra were recorded on a commercial NMR spectrometer (400 MHz for $^1H$, respectively, and 100 MHz for $^{13}C$, respectively), with chemical shifts reported relative to the residue peaks of solvent DMSO (δ 2.50 for $^1H$ and 39.5 for $^{13}C$). IR spectra were obtained on a FT-IR spectrophotometer and are given in $cm^{-1}$. Low resolution mass spectra (LRMS) and high resolution mass spectra were obtained on commercial instruments.

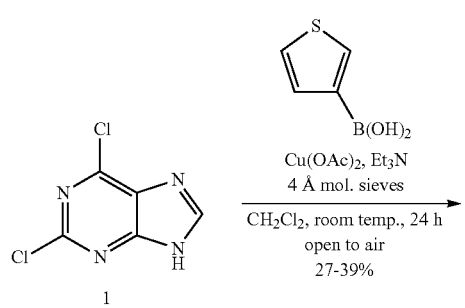

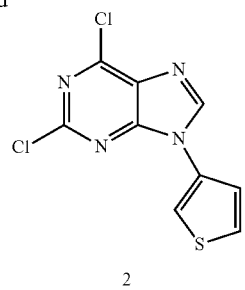

2

Synthesis of 2,6-Dichloro-9-(3-thiophene)-purine (2)

(See, Ding, S.; Gray, N. S.; Ding, Q.; Schultz, P. G. Tetrahedron Lett. 2001, 42, 8751-8755) A 250 mL round bottom flask was sequentially charged with 2,6-dichloropurine (18.9 g, 100 mmol), thiophene-3-boronic acid (25.6 g, 200 mmol), anhydrous cupric acetate (36.3 g, 200 mmol), activated 4 Å molecular sieves (50 g), freshly distilled triethylamine (300 mmol, 41.8 mL), and dry dichloromethane (500 mL). The reaction was stirred open to the air at room temperature for 24 h. The reaction mixture was then filtered through a plug of Celite that was subsequently rinsed with methanol. The filtrate was concentrated to a thick oil, and the crude material was purified by flash chromatography (99/1: $CH_2Cl_2$/MeOH) to give 7.31 g (27%) of 2,6-dichloro-9-(3-thiophene)-purine (2) as a light tan fluffy solid; $^1H$ NMR (400 MHz, $d_6$-DMSO) δ 9.15 (s, 1H), 8.11 (dd, J=1.51 & 3.28 Hz, 1H), 7.83 (dd, J=3.15 & 5.17 Hz, 1H), 7.70 (dd, J=1.39 & 5.17 Hz, 1H); $^{13}C$ NMR (100 MHz, $d_6$-DMSO) δ 152.1, 151.6, 150.1, 146.7, 131.2, 130.7, 127.7, 121.9. 116.9; IR (neat) 1712, 1587, 1557, 1357, 1210, 1161, 1035, 960, 859, 785 $cm^{-1}$.

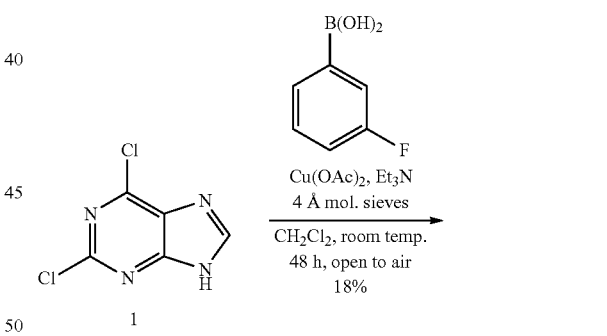

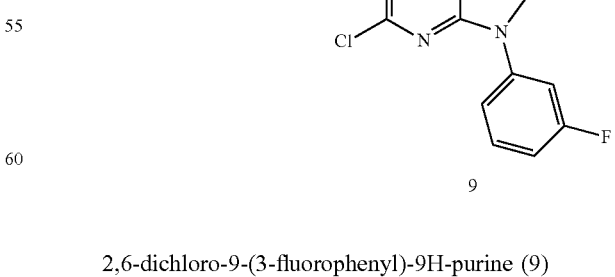

9

2,6-dichloro-9-(3-fluorophenyl)-9H-purine (9)

A 250 mL round bottom flask was sequentially charged with 2,6-dichloropurine (5.1 g, 27 mmol), 3-fluorophenylboronic acid (7.56 g, 54 mmol), anhydrous cupric acetate (9.77 g, 54 mmol), activated 4 Å molecular sieves (54 g), triethylamine (81 mmol, 11.2 mL), and dichloromethane (90 mL). The reaction was stirred open to the air at room temperature for 48 h. The reaction mixture was then filtered through a plug of Celite that was subsequently rinsed with methanol. The filtrate was concentrated to a thick oil, and the crude material was purified by flash chromatography (99/1: $CH_2Cl_2$/MeOH) to give 1.38 g (18%) of 2,6-dichloro-9-(3-fluorophenyl)-purine (9) as a white powder; $^1$H NMR (400 MHz, do-DMSO) δ 9.16 (s, 1H), 7.81 (td, J=2.12, 9.92 Hz, 1H), 7.67-7.78 (m, 2H), 7.39-7.46 (m, 1H). $^{13}$C NMR (101 MHz, DMSO-$d_6$) δ 162.1 (d, J=245.17 Hz), 152.8, 151.6, 147.1, 134.9, 131.6 (d, J=8.78 Hz), 131.2, 119.7 (d, J=2.93 Hz), 115.6 (d, J=21.22 Hz), 111.2 (d, J=25.61 Hz).

placed in a pre-heated oil bath at 65° C. for 2 h. The reaction mixture was cooled to room temperature then concentrated in vacuo, and pumped on a vacuum line overnight. The crude material was dissolved in THF (190 mL) to which piperidine (37.5 mL, 380 mmol) was added. The resulting mixture was stirred for 1 h. The reaction mixture was concentrated in vacuo and the crude product was purified by flash chromatography (80/20: EtOACMeOH buffered with 1% $NH_4OH$) to give 4.6 g (63%) of 4-nitro-2-(aminomethyl)-benzimidazole as a light orange solid; $^1$H NMR (400 MHz, $d_6$-DMSO) δ 8.07 (dd, J=1.01 & 8.08 Hz, 1H), 8.02 (dd, J=1.01 & 7.83 Hz, 1H), 7.35 (t, J=8.08 Hz, 1H), 6.0-5.0 (bs, 2H), 3.96 (bs, 2H); $^{13}$C NMR (100 MHz, do-DMSO) δ 160.5, 145.1, 133.0, 129.3, 125.4, 120.7, 117.9, 39.7; IR (neat) 3096, 1503, 1480, 1345, 1334, 1268, 1221, 1016, 921, 820, 808, 734 cm$^{-1}$.

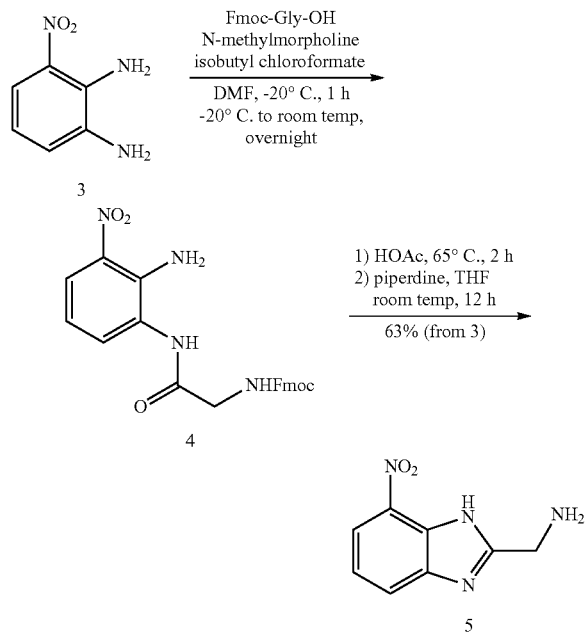

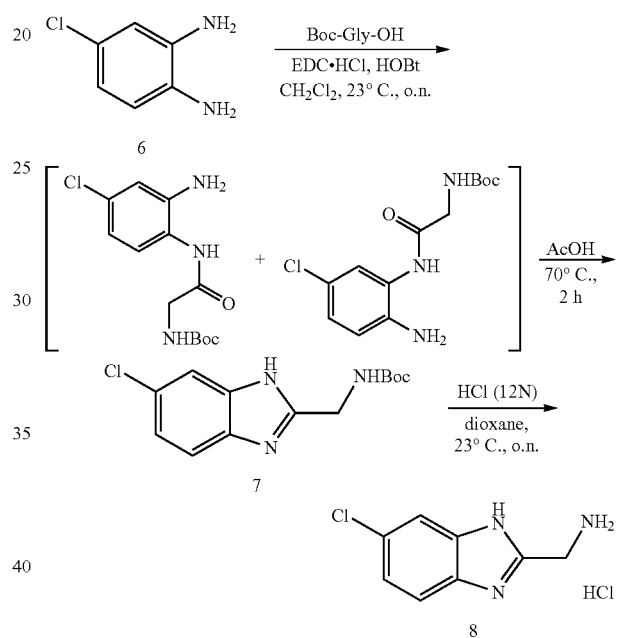

Synthesis of 4-nitro-2-(aminomethyl)-benzimidazole (5)

A dry 200 mL round bottom flask was charged with Fmoc-Gly-OH (11.3 g, 38 mmol) and placed under an atmosphere of argon. Dry DMF (38 mL) and N-methylmorpholine (4.2 mL, 38 mmol) were sequentially injected. The round bottom flask was then placed in an ice-salt bath. After the reaction mixture had equilibrated, isobutyl chloroformate (1 equiv., 38 mmol, 5.0 mL) was injected dropwise, and the reaction was stirred for 1 h. 3-Nitro-2-aminoaniline (5.8 g, 38 mmol) was quickly added to the reaction flask, which was then flushed under a positive pressure of argon for 1 min. The round bottom flask was then removed from the ice-salt bath and the reaction was allowed to gradually warm to room temperature overnight. The reaction flask was placed on a rotary evaporator to remove volatile byproducts. The crude reaction mixture was transferred to a separatory funnel containing ethyl acetate and water. The organic layer was washed with 5% $NaHCO_3$ and then brine. The organic layer was dried over $Na_2SO_4$, filtered, and concentrated in vacuo to give crude 4. Acetic acid (80 mL) was then added to the round bottom containing crude 4. The flask was then (5-chloro-1H-benzo[d]imidazol-2-yl)methanamine hydrochloride (8)

A 250 ml round bottom flask was charged with N-Boc-glycine (15 mmol, 2.62 g), EDC.HCl (18 mmol, 3.44 g), HOBt.$H_2O$ (21 mmol, 3.21 g) and methylene chloride (150 ml). The mixture was stirred at room temperature for 10 min. 4-chloro-1,2-phenylenediamine (15 mmol, 2.13 g) and DMF (2 ml) were added. The mixture was stirred overnight at room temperature. DCM was evaporated and ethyl acetate was added (50 ml). The organic phase was washed 2 times with brine, 2 times with $NH_4Cl$ (saturated in water), 2 times with $NaHCO_3$ (saturated in water) and finally once with brine. The organic layer was dried over $Na_2SO_4$ and the solvent was evaporated under vacuum. 10 ml of acetic acid were added and this mixture was heated for 2 hrs at 70° C. After evaporation the obtained mixture was precipitated in methylene chloride and filtered afford 2.02 g of compound 7 as a pink solid (yield 48%). $^1$H NMR (400 MHz, DMSO-$d_6$) δ 12.37 (br. s., 1H), 7.37-7.64 (m, 3H), 7.16 (dd, J=2.02, 8.59 Hz, 1H). 4.35 (d, J=5.81 Hz, 2H), 1.41 (s, 9H). LRMS-ESI (M+H)$^+$ m/z: 282.1, 284.1. Compound 7 (7.12 mmol, 2.0 g) was added in a 100 ml flask with 10 ml of conc. HCl (12 N in water) and 10 ml of dioxane. The mixture was stirred overnight at room temperature. The solvent was evaporated under vacuum. The obtained powder was triturated with ether and filtered to give 1.25 g (97%) of 8 as a white powder. ¹H NMR (400 MHz, DMSO-d₆) δ 8.88 (br. s., 3H), 7.77 (d, J=1.52 Hz, 1H), 7.68 (d, J=8.59 Hz, 1H), 7.33 (dd, J=2.02, 8.59 Hz, 1H), 4.38 (br. s., 2H). LRMS-ESI (M+H)⁺ mz: 182.1, 184.1.

10 ml of dioxane. The mixture was stirred overnight at room temperature. The solvent was evaporated under vacuum. The obtained powder was triturated with ether and filtered to give 1.24 g (quantitative yield) of 12 as a grey powder. ¹H NMR (400 MHz, DMSO-d₆) δ 8.76 (br. s., 3H), 7.40 (ddd, J=1.14, 3.85, 8.91 Hz, 1H), 7.29 (ddd, J=7.33, 8.84, 11.62 Hz, 1H), 4.33 (q, J=5.73 Hz, 3H). LRMS-ESI (M+H)⁺ mz: 184.1.

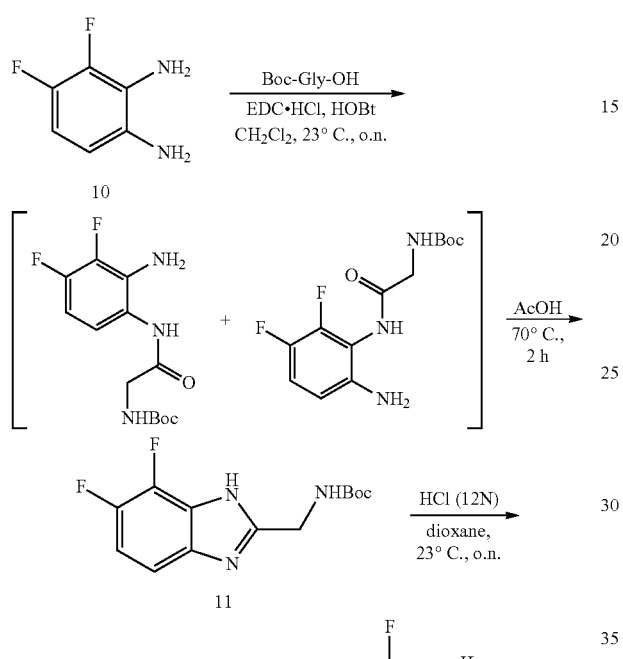

Synthesis of (4,5-difluoro-1H-benzo[d]imidazol-2-yl)methanamine hydrochloride (12)

A 250 ml round bottom flask was charged with N-Boc-glycine (6.94 mmol, 1.21 g), EDC.HCl (8.33 mmol, 1.59 g), HOBt.H₂O (9.72 mmol, 1.49 g) and methylene chloride (70 ml). The mixture was stirred at room temperature for 10 min. 3,4-difluoro-1,2-phenylenediamine (6.94 mmol, 1 g) and DMF (2 ml) were added. The mixture was stirred overnight at room temperature. DCM was evaporated and ethyl acetate was added (50 ml). The organic phase was washed 2 times with brine, 2 times with NH₄Cl (saturated in water), 2 times with NaHCO₃ (saturated in water) and finally once with brine. The organic layer was dried over Na₂SO₄ and the solvent was evaporated under vacuum. 10 ml of acetic acid were added and this mixture was heated for 2 hrs at 70° C. After evaporation the obtained mixture was precipitated in ethyl ether and filtered affording 1.609 g of compound 11 as beige powder (yield 82%). ¹H NMR (400 MHz, DMSO-d₆) δ 12.61 (br. s., 1H), 7.49 (br. s., 1H), 7.10-7.37 (m, 2H), 4.35 (d, J=5.81 Hz, 2H), 1.41 (s, 9H). LRMS-ESI (M+H)⁺ m/z: 284.1. Compound 11 (5.68 mmol, 1.61 g) was added in a 100 ml flask with 10 ml of conc. HCl (12 N in water) and

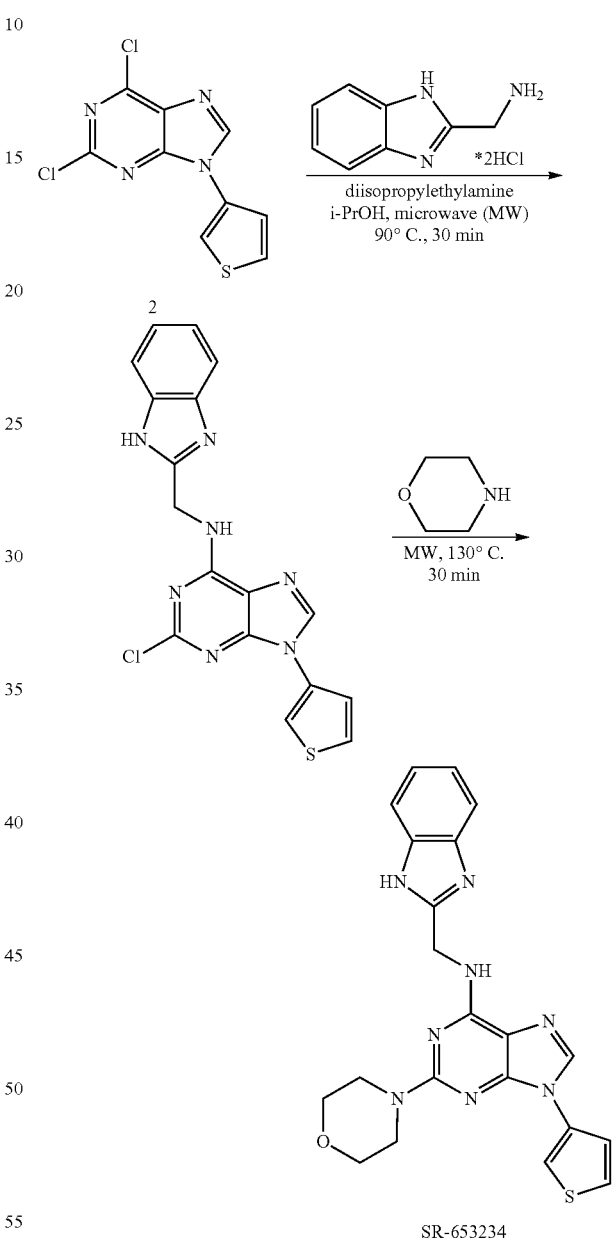

Synthesis of SR-653234

A 2-5 mL Biotage microwave vial was charged with 2,6-dichloropurine-9-(3-thiophene)-purine (2) (0.136 g, 0.5 mmol), 2-(aminomethyl)-benzimidazole dihydrochloride (0.121 g, 0.55 mmol), freshly distilled N,N-diisopropylethylamine (0.435 mL, 2.5 mmol), and isopropanol (2 mL). The vial was sealed with a microwave cap, and then the reaction mixture was heated to 90° C. for 30 minutes in a Biotage microwave reactor. The cooled vial was then placed on a rotary evaporator and the reaction mixture was concentrated.

Morpholine (2.5 mL) was added to the vial containing the concentrated crude mixture. The vial was resealed and the reaction was heated to 130° C. for 30 minutes in the microwave unit. The cooled reaction mixture was concentrated on a rotary evaporator, then the crude product was purified by flash chromatography (98/2 (500 mL) then 955 (500 mL) [CH$_2$Cl$_2$/MeOH]) to give 0.151 g (70%) of SR-653234 as a white powder; $^1$H NMR (400 MHz, d$_6$-DMSO) δ 12.13 (s, 1H), 8.39 (s, 1H), 8.15 (bs, 1H), 8.10 (dd, J=1.51 & 3.28 Hz, 1H), 7.80 (dd, J=1.51 & 5.30 Hz, 1H), 7.73 (dd, J=3.28 & 5.30 Hz, 1H), 7.50 (bs, 1H), 7.41 (bs, 1H), 7.11 (dd, J=3.03 & 6.31 Hz, 1H), 4.84 (bs, 2H), 3.57 (bs, 4H), 3.51 (bs, 4H); $^{13}$C NMR (100 MHz, d$_6$-DMSO) δ 158.7, 154.2, 153.1, 150.1, 143.0, 136.2, 134.2, 133.7, 126.8, 121.4, 121.0, 120.8, 118.0, 113.7, 112.8, 111.9, 65.8, 44.5, 38.5; IR (neat) 1615, 1438, 1430, 1335, 1310, 1272, 1116, 865, 783, 730 cm$^{-1}$. LRMS-ESI (M+) m/z: 432.51.

Synthesis of SR-1277:

A 2-5 mL Biotage microwave vial was charged with 2,6-dichloropurine-9-(3-thiophene)-purine (2) (0.136 g, 0.5 mmol), 4-nitro-2-(aminomethyl)-benzimidazole (5) (0.105 g, 0.55 mmol), freshly distilled N,N-diisopropylethylamine (0.435 mL, 2.5 mmol), and isopropanol (2 mL). The vial was sealed with a microwave cap, and the reaction mixture was heated to 90° C. for 30 minutes in a Biotage microwave unit. The cooled vial was then placed on a rotary evaporator and the reaction mixture was concentrated. Morpholine (2.5 mL) was added to the vial containing the concentrated crude mixture. The vial was resealed and the reaction was heated to 130° C. for 30 minutes in the microwave reactor. The cooled reaction mixture was concentrated in vacuo, and the crude product was subjected to flash chromatographic purification (982 (500 mL) then 955 (500 mL) [CH$_2$Cl$_2$MeOH]) to give 0.156 g (65%) of SR-1277 as a tan-orange powder; m.p.=decomposed at 290° C.; $^1$H NMR (400 MHz, d$_6$-DMSO) δ 13.1 (s, 1H), 8.39 (s, 1H), 8.15 (bs, 1H), 8.09 (d, J=8.05 Hz, 1H), 8.07 (dd, J=1.51 & 3.03 Hz, 1H), 8.03 (d, J=7.32 Hz, 1H), 7.78 (dd, J=1.51 & 5.30 Hz, 1H), 7.73 (dd, J=3.28 & 5.30 Hz, 1H), 7.36 (t, J=8.08 Hz, 1H), 4.95 (bs, 2H), 3.60 (bs, 4H), 3.53 (bs, 4H); $^{13}$C NMR (100 MHz, d$_6$-DMSO) δ 158.6, 156.8, 154.0, 153.9, 150.0, 136.4, 133.6, 126.7, 121.0, 120.8, 118.1, 113.6, 112.8, 65.8, 48.5, 44.4; IR (neat) 1605, 1484, 1411, 1325, 1268, 1238, 1115, 1014, 901, 864, 783, 733 cm$^{-1}$; LRMS-ESI (M+1) m/z: 478, 398, 279, 201, 171, 139.

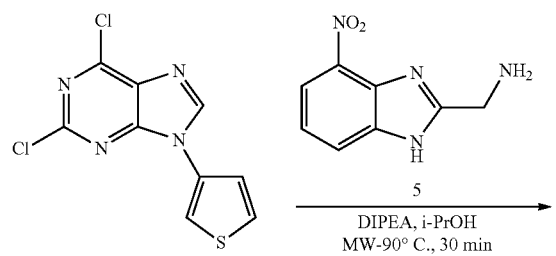

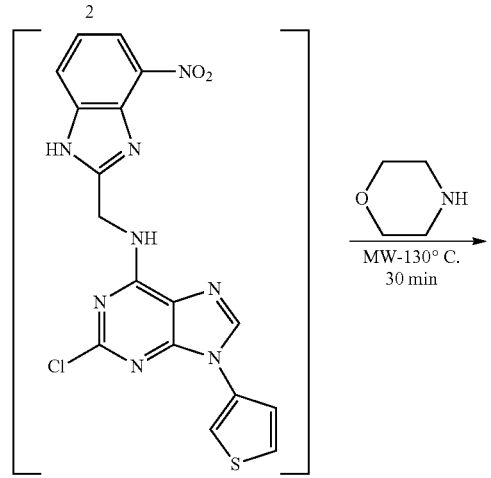

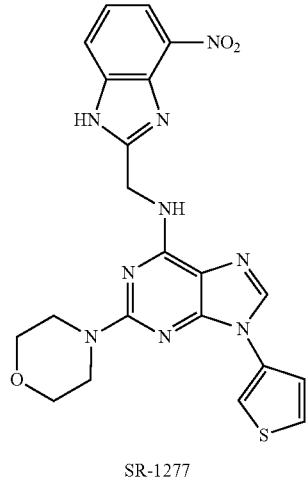

SR-1277

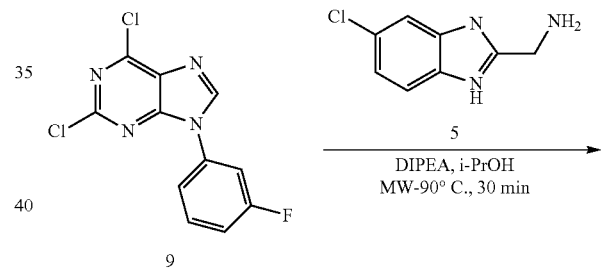

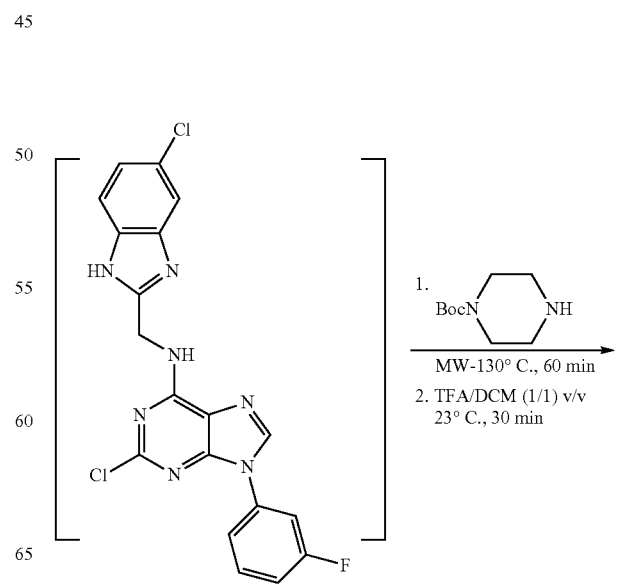

-continued

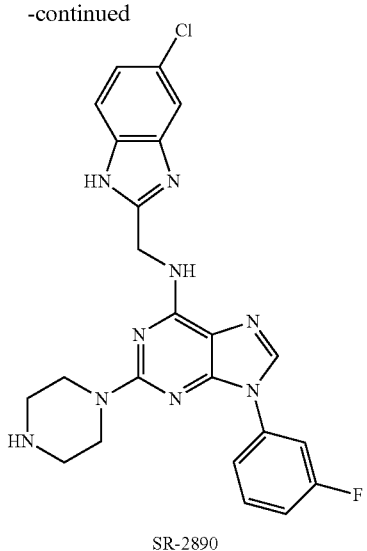

SR-2890

Synthesis of SR-2890:

A 0.5-2 mL Biotage microwave vial was charged with 2,6-dichloropurine-9-(3-fluorophenyl)-purine (0.2 mmol, 0.056 g), 2-(methylamino)-5-chloro-benzimidazole hydrochloride (0.2 mmol, 0.86 g), N,N-diisopropylethylamine (1 mmol, 0.174 mL), and isopropanol (0.5 mL). The vial was sealed with a microwave cap, and then the reaction mixture was heated to 90° C. for 30 minutes in a Biotage microwave reactor. The cooled vial was then placed on a rotary evaporator and the reaction mixture was concentrated. N-Boc-piperazine (2 mmol, 0.372 g) was added to the vial containing the concentrated crude mixture. The vial was resealed and the reaction was heated to 130° C. for 60 minutes in the microwave unit. The cooled reaction mixture was concentrated on a rotary evaporator. 4 ml of a 50/50 TFA/DCM solution was added to the residue and stirred for 30 minutes at room temperature. The mixture was evaporated and then 3 ml of DMF was added and the crude product was purified by preparative HPLC to yield 11 as a white powder (42 mg, 0.66 mmol, 33%); $^1$H NMR (400 MHz, DMSO-d$_6$): δ (ppm) 8.89 (br. s., 2H), 8.59-8.73 (m, 1H), 8.48 (s, 1H), 7.76-7.90 (m, 3H), 7.71 (d, J=8.59 Hz, 1H), 7.60 (dt, J=6.57, 8.21 Hz, 1H), 7.46 (dd, J=1.89, 8.72 Hz, 1H), 7.18-7.31 (m, 1H), 4.91-5.13 (m, 2H), 3.69 (br. s., 4H), 2.95 (br. s., 4H) $^{13}$C NMR (101 MHz, DMSO-d$_6$) δ (ppm) 162.2 (d, J=243 Hz), 158.7 (q, J=34.40 Hz), 157.8, 155.0, 154.1, 137.6, 136.8 (d, J=10.98 Hz), 131.3 (d, J=8.78 Hz), 128.9, 124.8, 117.8 (d, J=3 Hz), 117.7, 115.5, 114.7, 114.38, 114.0, 113.6 (d, J=20.49 Hz), 109.3 (d, J=26.35 Hz)), 42.2, 40.9, 37.6. $^{19}$F NMR (376 MHz, DMSO-d$_6$): δ (ppm) −78.5 (s, 7F), 114.9 (m, 1F). HRMS (ESI) m/z calcd for $C_{23}H_{21}ClFN_9$ (M+H)$^+$ 478.1671, found 478.1678.

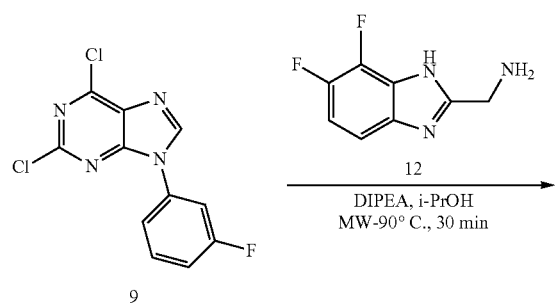

-continued

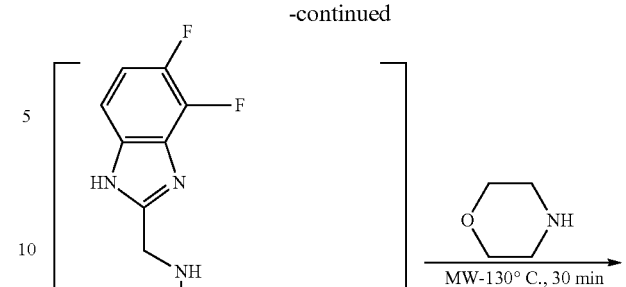

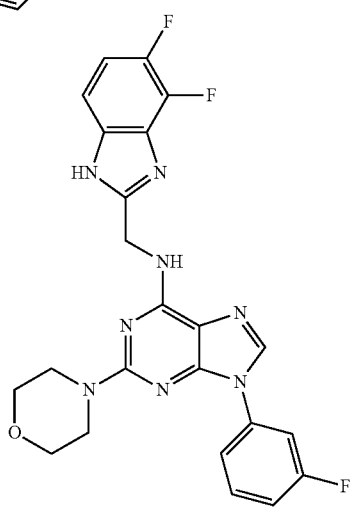

SR-3029

Synthesis of SR-3029:

A 2-5 mL Biotage microwave vial was charged with 2,6-dichloropurine-9-(3-fluorophenyl)-purine (1 mmol, 0.281 g), 2-(methylamino)-4,5-difluoro-benzimidazole hydrochloride (1.1 mmol, 0.254 g), N,N-diisopropylethylamine (5 mmol, 0.871 mL), and isopropanol (2.5 mL). The vial was sealed with a microwave cap, and then the reaction mixture was heated to 90° C. for 30 minutes in a Biotage microwave reactor. The cooled vial was then placed on a rotary evaporator and the reaction mixture was concentrated. Morpholine (2.5 mL) was added to the vial containing the concentrated crude mixture. The vial was resealed and the reaction was heated to 100° C. for 60 minutes in the oil bath. The cooled reaction mixture was concentrated on a rotary evaporator and then the crude product was purified by preparative HPLC to give 12 as a white solid (0.310 g, 0.522 mmol, 52%). $^1$H NMR (400 MHz, DMSO-d$_6$) δ (ppm) 8.43 (s, 1H), 8.37 (br. s., 1H), 7.88 (td, J=2.15, 10.61 Hz, 1H), 7.81-7.86 (m, J=1.26 Hz, 1H), 7.59 (dt, J=6.69, 8.27 Hz, 1H), 7.19-7.33 (m, 3H), 4.90 (br. s., 2H), 3.48 (br. s., 8H) 13C NMR (101 MHz, DMSO-d6) δ 162.2 (d, J=243.70 Hz), 158.6, 158.2, 155.9, 154.1, 150.6, 145.4 (dd, J=9.52, 235.65 Hz), 137.1 (d, J=10.98 Hz), 136.8, 133.2, 131.2 (d, J=9.52 Hz), 117.6 (d, J=2.93 Hz), 117.0, 114.0 (d, J=10.98 Hz), 113.4 (d, J=20.49 Hz), 111.8 (d, J=20.49 Hz), 109.0 (d, J=25.61 Hz), 108.6 (m), 65.8, 44.5, 38.3 19F NMR (376 MHz, DMSO-d6): δ (ppm) −78.5 (s, 4F), 114.9 (m, 1F), 151.8 (s, 1F), 158.6 (dd, J=5.73, 21.8 Hz, 1F). HRMS (ESI) m/z calcd for $C_{23}H_{19}F_3N_8O$ (M+H)$^+$ 481.1712, found 481.1714.

While the invention has been described and exemplified in sufficient detail for those skilled in this art to make and use it, various alternatives, modifications, and improvements will be apparent to those skilled in the art without departing from the spirit and scope of the claims.

All patents and publications referred to herein are incorporated by reference herein to the same extent as if each individual publication was specifically and individually indicated to be incorporated by reference in its entirety.

Each substituent described in each Markush group can be stated separately as a stand-alone substituent and can be combined in any fashion with any one or more of the other substituents recited in each Markush group.

The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

Additional Embodiments

The present invention provides for the following exemplary embodiments:

Embodiment 1. A compound of formula (I),

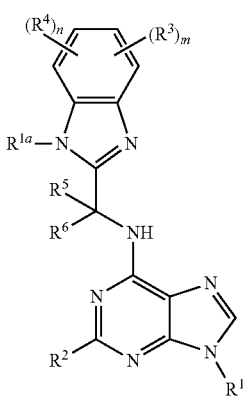

(I)

wherein $R^1$ and $R^{1a}$ are each independently selected from the group comprising hydrogen, deuterium, $(CH_2)_{0-4}N(R)_2$, $(CH_2)_{0-4}SO_3R$, $(CH_2)_{0-4}C(O)R$, $(CH_2)_{0-4}C(O)C(O)R$, $(CH_2)_{0-4}C(O)CH_2C(O)R$, $(CH_2)_{0-4}C(S)R$, $(CH_2)_{0-4}C(O)OR$, $(CH_2)_{0-4}OC(O)R$, $(CH_2)_{0-4}OC(O)OR$, $(CH_2)_{0-4}C(O)N(R)_2$, $OC(O)N(R)_2$, $(CH_2)_{0-4}C(S)N(R)_2$, $(CH_2)_{0-4}NHC(O)R$, $(CH_2)_{0-4}N(R)SO_2R$, $(CH_2)_{0-4}N(R)SO_2N(R)_2$, $(CH_2)_{0-4}N(R)C(O)OR$, $(CH_2)_{0-4}N(R)C(O)R$, $(CH_2)_{0-4}N(R)C(S)R$, $(CH_2)_{0-4}N(R)C(O)N(R)_2$, $(CH_2)_{0-4}N(R)C(S)N(R)_2$, $(CH_2)_{0-4}N(COR)COR$, $(CH_2)_{0-4}N(OR)R$, $(CH_2)_{0-4}C(=NH)N(R_2)$, $(CH_2)_{0-4}C(O)N(OR)R$, $(CH_2)_{0-4}C(=NOR)R$, $(C_{1-4})$alkyl, $(C_{1-4})$alkoxy, $(C_{1-4})$acyloxy, cycloalkyl, heterocyclyl, aryl, and heteroaryl; wherein any alkyl, alkoxy, acyloxy, cycloalkyl, heterocyclyl, aryl, heteroaryl can be mono- or independently multi-substituted with J, $(C_{1-6})$alkyl, $(C_{2-6})$alkenyl, $(C_{2-6})$alkynyl, $(C_{1-6})$haloalkyl, $(C_{1-6})$alkoxy, $(C_{1-6})$haloalkoxy, cycloalkyl($C_{0-6}$)alkyl, heterocyclyl($C_{1-6}$)alkyl, aryl($C_{0-6}$)alkyl, or heteroaryl($C_{0-6}$)alkyl, of which any alkyl, alkenyl, alkynyl, haloalkyl, alkoxy, haloalkoxy, cycloalkyl, aryl, heterocyclyl, or heteroaryl can be further substituted with J;

$R^2$, $R^3$, $R^4$, $R^5$, and $R^6$ each are independently selected from the group comprising F, Cl, Br, I, OR, CN, $CF_3$, $OCF_3$, $NO_2$, R, $(CH_2)_{0-4}N(R)_2$, $(CH_2)_{0-4}SR$, $(CH_2)_{0-4}SOR$, $(CH_2)_{0-4}SO_2R$, $(CH_2)_{0-4}SO_2N(R)_2$, $(CH_2)_{0-4}SO_3R$, $(CH_2)_{0-4}C(O)R$, $(CH_2)_{0-4}C(O)C(O)R$, $(CH_2)_{0-4}C(O)CH_2C(O)R$, $(CH_2)_{0-4}C(S)R$, $(CH_2)_{0-4}C(O)OR$, $(CH_2)_{0-4}OC(O)R$, $(CH_2)_{0-4}OC(O)OR$, $(CH_2)_{0-4}C(O)N(R)_2$, $(CH_2)_{0-4}OC(O)N(R)_2$, $(CH_2)_{0-4}C(S)N(R)_2$, $(CH_2)_{0-4}NHC(O)R$, $(CH_2)_{0-4}N(R)N(R)C(O)R$, $(CH_2)_{0-4}N(R)N(R)C(O)OR$, $(CH_2)_{0-4}N(R)N(R)CON(R_2)$, $(CH_2)_{0-4}N(R)SO_2R$, $(CH_2)_{0-4}N(R)SO_2N(R)_2$, $(CH_2)_{0-4}N(R)C(O)OR$, $(CH_2)_{0-4}N(R)C(O)R$, $(CH_2)_{0-4}N(R)C(S)R$, $(CH_2)_{0-4}N(R)C(O)N(R)_2$, $(CH_2)_{0-4}N(R)C(S)N(R)_2$, $(CH_2)_{0-4}N(R)C(S)N(R)_2$, $(CH_2)_{0-4}N(COR)COR$, $(CH_2)_{0-4}N(OR)R$, $(CH_2)_{0-4}C(=NH)N(R)_2$, $(CH_2)_{0-4}C(O)N(OR)R$, $(CH_2)_{0-4}C(=NOR)R$, $(C_{1-4})$alkyl, $(C_{1-4})$alkoxy, $(C_{1-4})$acyloxy, cycloalkyl, heterocyclyl, aryl, and heteroaryl; wherein any alkyl, alkoxy, acyloxy, cycloalkyl, heterocyclyl, aryl, heteroaryl can be mono- or independently multi-substituted with J, $(C_{1-6})$alkyl, $(C_{2-6})$alkenyl, $(C_{2-6})$alkynyl, $(C_{1-6})$haloalkyl, $(C_{1-6})$alkoxy, $(C_{1-6})$haloalkoxy, cycloalkyl($C_{0-6}$)alkyl, heterocyclyl($C_{0-6}$)alkyl, aryl($C_{0-6}$)alkyl, or heteroaryl($C_{0-6}$)alkyl; wherein any alkyl, alkenyl, alkynyl, haloalkyl, alkoxy, haloalkoxy, cycloalkyl, aryl, heterocyclyl, or heteroaryl can be further substituted with J;

wherein m and n are each independently 0, 1, 2, or 3, provided m plus n is less than or equal to 4;

wherein J independently at each occurrence is selected from the group comprising F, Cl, Br, I, OR, CN, $CF_3$, $OCF_3$, $NO_2$, R, O, S, C(O), C(S), S(O), methylenedioxy, ethylenedioxy, $N(R)_2$, SR, SOR, $SO_2R$, $SO_2N(R)_2$, $SO_3R$, C(O)R, C(O)C(O)R, $C(O)CH_2C(O)R$, C(S)R, C(O)OR, OC(O)R, OC(O)OR, $C(O)N(R)_2$, $OC(O)N(R)_2$, $C(S)N(R)_2$, $(CH_2)_{0-4}NHC(O)R$, N(R)N(R)C(O)R, N(R)N(R)C(O)OR, $N(R)N(R)CON(R_2)$, $N(R)SO_2R$, $N(R)SO_2N(R)_2$, N(R)C(O)OR, N(R)C(O)R, N(R)C(S)R, $N(R)C(O)N(R)_2$, N(R)C(S)N(R)_2, N(COR)COR, N(OR)R, $C(=NH)N(R_2)$, C(O)N(OR)R, C(=NOR)R, $(C_{1-4})$alkyl, $(C_{1-4})$alkoxy, $(C_{1-4})$acyloxy, cycloalkyl, heterocyclyl, aryl, and heteroaryl; wherein any alkyl, alkoxy, acyloxy, cycloalkyl, heterocyclyl, aryl, hetero aryl can be mono- or independently multi-substituted with R, $(C_{1-6})$alkyl, $(C_{2-6})$alkenyl, $(C_{2-6})$alkynyl, $(C_{1-6})$haloalkyl, $(C_{1-6})$alkoxy, $(C_{1-6})$haloalkoxy, cycloalkyl($C_{0-6}$)alkyl, heterocyclyl($C_{0-6}$)alkyl, aryl($C_{0-6}$)alkyl, or heteroaryl($C_{0-6}$)alkyl; wherein any alkyl, alkenyl, alkynyl, haloalkyl, alkoxy, haloalkoxy, cycloalkyl, aryl, heterocyclyl, or heteroaryl can be further mono- or independently multi-substituted with R; or wherein two R groups together with a nitrogen atom or with two adjacent nitrogen atoms to which they are bonded can together form a $(C_{3-8})$heterocyclyl mono- or multi-substituted with R; optionally further comprising 1-3 additional heteroatoms selected from the group comprising O, N, S, S(O) and $S(O)_2$;

wherein R is independently at each occurrence is selected from the group consisting of hydrogen, deuterium, F, Cl, Br, I, OH, CN, $CF_3$, $OCF_3$, $NO_2$, alkyl, cycloalkyl, cycloalkylalkyl, aryl, aralkyl, heterocyclyl, heterocyclylalkyl, heteroaryl, and heteroarylalkyl; wherein any alkyl, cycloalkyl, cycloalkylalkyl, aryl, aralkyl, heterocyclyl, heterocyclylalkyl, heteroaryl, or heteroarylalkyl is substituted with 0-3 $J^R$; or wherein two R groups together with a nitrogen atom or with two adjacent nitrogen atoms to which they are bonded can together form a $(C_{3-8})$heterocyclyl substituted with 0-3 $J^R$; optionally further comprising 1-3 additional hetero atoms selected from the group consisting of O, N, S, S(O) and $S(O)_2$;

wherein any cycloalkyl, aryl, heterocyclyl, or heteroaryl can be fused, bridged, or in a spiro configuration with one or more additional optionally mono- or independently multi-$J^R$ substituted cycloalkyl, aryl, heterocyclyl, and heteroaryl, monocyclic, bicyclic, bicyclic or polycyclic, saturated, partially unsaturated, or aromatic rings;

wherein $J^R$ is independently at each occurrence is selected from the group consisting of F, Cl, Br, I, OR, CN, $CF_3$, $OCF_3$, $NO_2$, O, S, C(O), C(S), S(O), methylenedioxy, ethylenedioxy, $N(R)_2$, SR, SOR, $SO_2R$, $SO_2N(R)_2$, $SO_3R$, C(O)R, C(O)C(O)R, $C(O)CH_2C(O)R$, C(S)R, C(O)OR, OC(O)R, OC(O)OR, $C(O)N(R)_2$, $OC(O)N(R)_2$, $C(S)N(R)_2$, $(CH_2)_{0-4}NHC(O)R$, N(R)N(R)C(O)R, N(R)N(R)C(O)OR, $N(R)N(R)CON(R_2)$, $N(R)SO_2R$, $N(R)SO_2N(R)_2$, N(R)C(O) OR, N(R)C(O)R, N(R)C(S)R, $N(R)C(O)N(R)_2$, N(R)C(S)N $(R)_2$, N(COR)COR, N(OR)R, $C(=NH)N(R_2)$, C(O)N(OR) R, C(=NOR)R, $(C_{1-4})$alkyl, $(C_{1-4})$alkoxy, $(C_{1-4})$acyloxy, cycloalkyl, heterocyclyl, aryl, and heteroaryl;

provided that the compound of formula (I) is not any of the following:

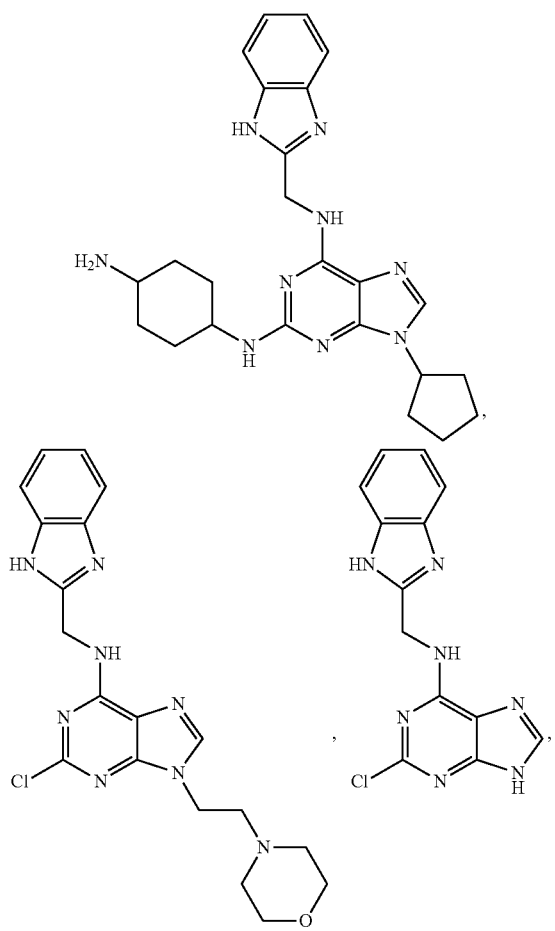

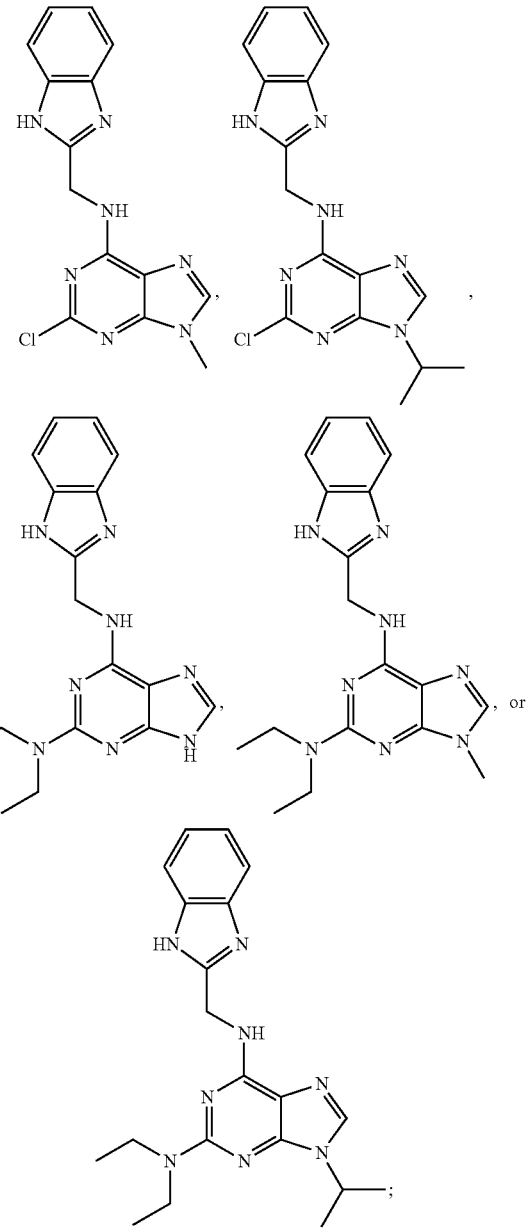

wherein the compound of formula (I) can be any stereoisomer thereof, or any salt, hydrate, solvate, tautomer, prodrug, or metabolite thereof.

Embodiment 2. The compound of embodiment 1 wherein $R^1$ and $R^{1a}$ are independently selected from the group comprising H, 2-thiophenyl, 3-furanyl, 2-furanyl, 3-1H-pyrrolyl, 2-1H-pyrrolyl, 4-1H-imidazolyl, 2-1H-imidazolyl, 5-oxazolyl, 4-thiazolyl, 2-oxooxazolidin-4-yl, 2-pyridinyl, 3-pyridinyl, 4-pyridinyl, 5-pyrimidinyl, and 2-pyrazinyl.

Embodiment 3. The compound of embodiment 1 wherein $R^2$ is selected from the group comprising 1-pyrrolidinyl, 1-piperidinyl, 1-piperazinyl, 4-methylpiperazin-1-yl, thiomorpholino, 4-(2-hydroxyethyl)piperazin-1-yl, (2-morpholinoethyl)amino, indolin-1-yl, diallylamino, and (R)-2-(1-phenylethyl)-amino.

Embodiment 4. The compound of embodiment 1 wherein $R^3$ and $R^4$ are independently selected from the group comprising H, 4-amino, 5-amino, 5-chloro, 4,5-difluoro, 4-nitro, 4-ethoxycarbonyl, 4-carboxylic acid, 4-methylsulfonamido, 4-methylphenylsulfonamido, 4-carbamoyl, 4-hydroxycarbamoyl, 4-methoxycarbamoyl, 4-(N—R-carbamoyl), 4-(S—R-sulfonyl)carbamoyl, 4-(3-hydroxyisoxazol-5-yl), 4-(3-hydroxyisothiazol-5-yl), 4-(5-hydroxyisoxazol-3-yl), 4-(3-hydroxy-1-methyl-1H-pyrazol-5-yl), 4-(1-hydroxy-1H-imadazol-5-yl), 4-(1-hydroxy-1H-imidazol-2-yl), 4-(1H-tetrazol-5-yl), 4-(3,5-difluoro-4-hydroxyphenyl), 4-(3-methyl-1,2,4-thiadiazol-5-yl), 4-(3-methyl-1,2,4-oxadiazol-5-yl), 4-(5-methyl-1,3,4-oxadiazol-2-yl), 4-(4-methoxy-1,2,5-oxadiazol-3-yl), 4-(5-methoxy-2-methyl-2H-1,2,3-triazol-4-yl), and 4-(2-methyl-2H-tetrazol-5-yl); wherein R is as defined in embodiment 1.

Embodiment 5. The compound of embodiment 1 wherein $R^3$ and $R^4$ together with the atoms to which they are bonded form a benzene ring fused at the f-side of the 1H-benzo[d]imidazole to give a 2-substituted-1H-naphtho[2,3-d]imidazole, or wherein $R^3$ and $R^4$ together with the atoms to which they are bonded form a pyridine ring 3,2-fused to the e-side of the 1H-benzo[d]imidazole to give a 2-substituted-3H-imidazo[4,5-f]quinoline.

Embodiment 6. The compound of embodiment 1 wherein $R^1$ and $R^{1a}$ are independently selected from the group comprising 3-thiophenyl, isopropyl, cyclopentyl, tetrahydro-2H-pyran-2-yl, and H.

Embodiment 7. The compound of embodiment 1 wherein $R^3$ and $R^4$ are independently selected from the group comprising H, 5-chloro, 4,5-difluoro, 4-trifluoromethanyl, 5-trifluoromethanyl, 5-fluoro, 5-cyano, 5-nitro, 5-methoxy, 5-chloro, 4-nitro, 4-ethoxycarbonyl, 5-ethoxycarbonyl, 4-$CO_2R$, 5-$CO_2R$, and H; wherein R is as defined in embodiment 1.

Embodiment 8. The compound of embodiment 1 wherein $R^2$ is selected from the group comprising morpholino, 3-pyridinylamino, 2-pyrazinylamino, 4-pyrimidinylamino, 4-(2-pyridinyl)piperazin-1-yl, and 4-(cyclopropylcarbamoyl)phenyl.

Embodiment 9. The compound of embodiment wherein $R^3$ is 4-bromo and $R^4$ is 6-trifluromethyl.

Embodiment 10. The compound of embodiment 1 wherein $R^1$ is 3-thiophenyl.

Embodiment 11. The compound of embodiment 1 wherein $R^1$ is isopropyl.

Embodiment 12. The compound of embodiment 1 wherein $R^2$ is morpholino.

Embodiment 13. The compound of embodiment 1 wherein $R^3$ is 4-$NO_2$.

Embodiment 14. The compound of embodiment 1 wherein $R^3$ is 4-$CO_2Et$.

Embodiment 15. The compound of embodiment 1 wherein $R^4$ is H or D.

Embodiment 16. The compound of embodiment 1 wherein $R^{1a}$, $R^5$, and $R^6$ are each independently H or D.

Embodiment 17. The compound of embodiment 1 wherein the compound is selected from the group comprising

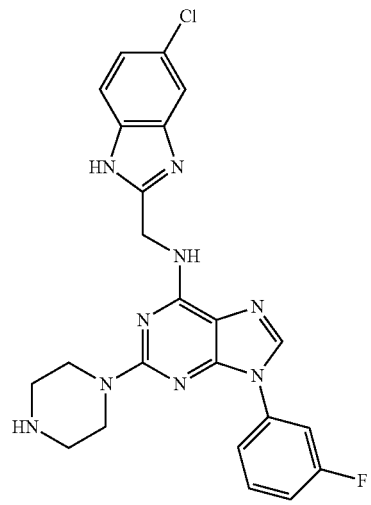

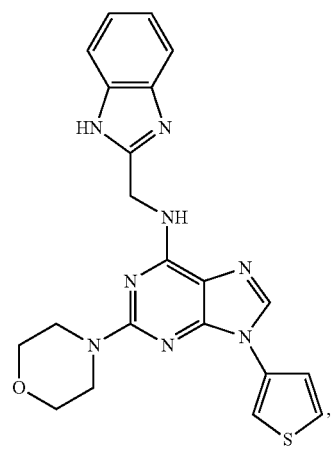

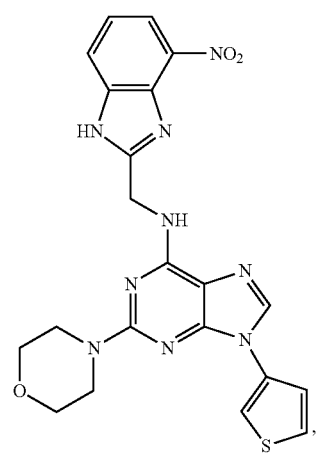

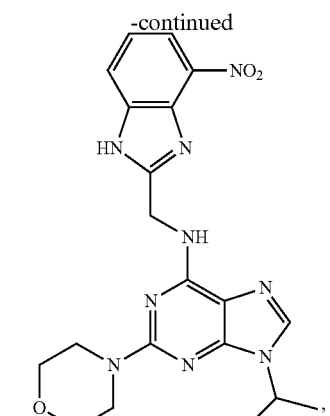
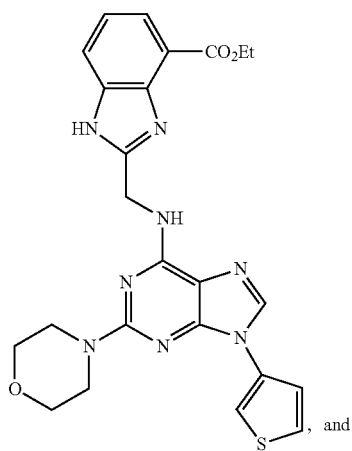
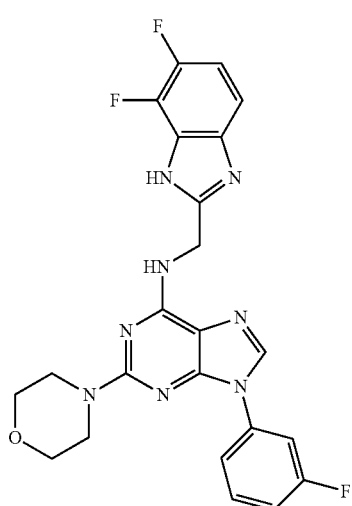
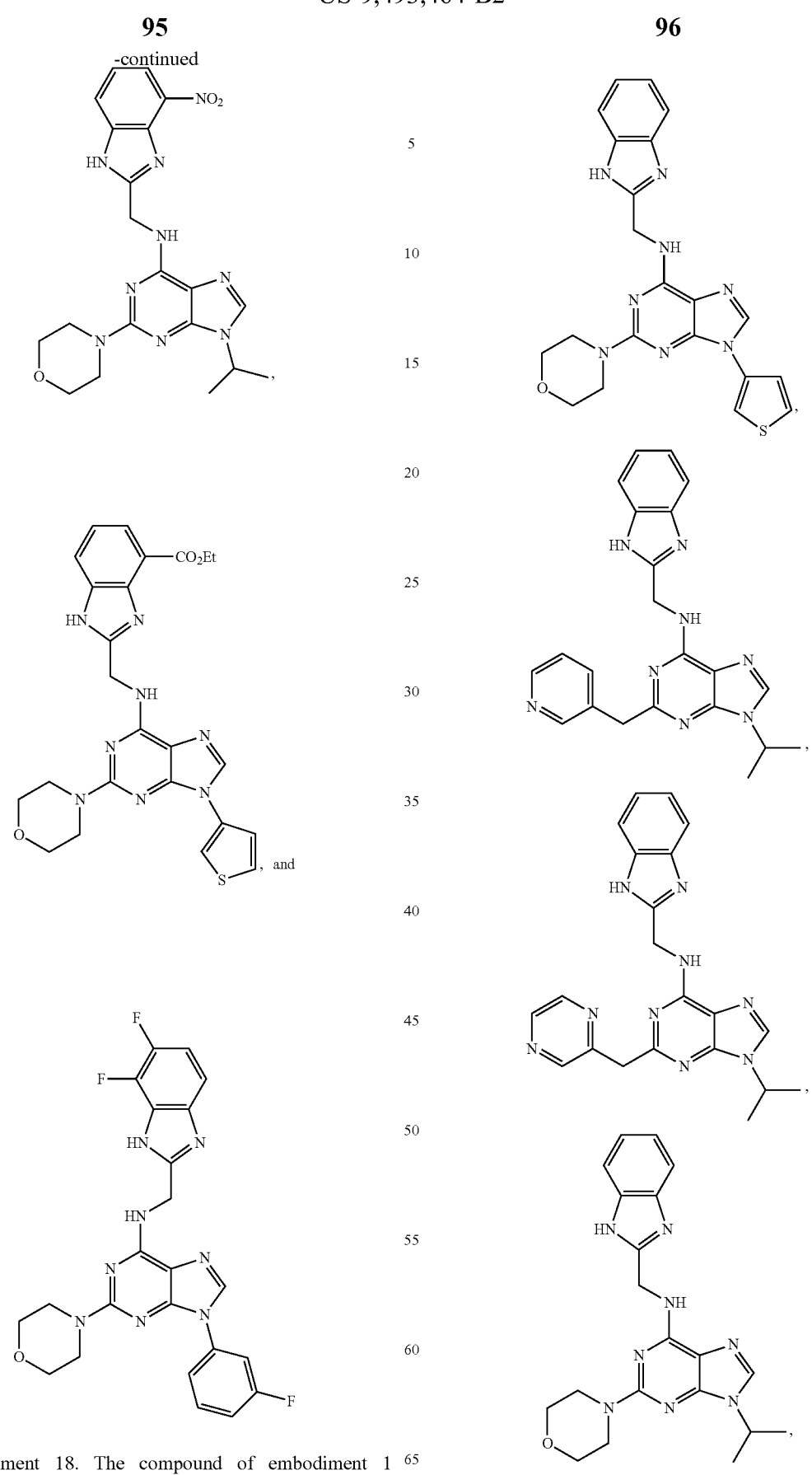
Embodiment 18. The compound of embodiment 1 wherein the compound is selected from the group comprising

| 97 | 98 |
|---|---|
| -continued | -continued |
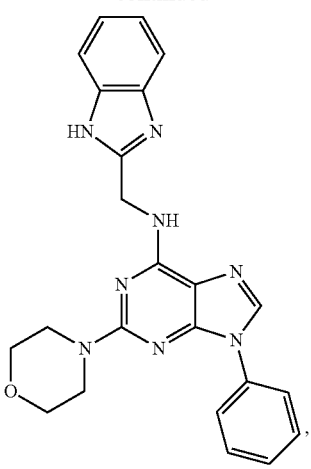
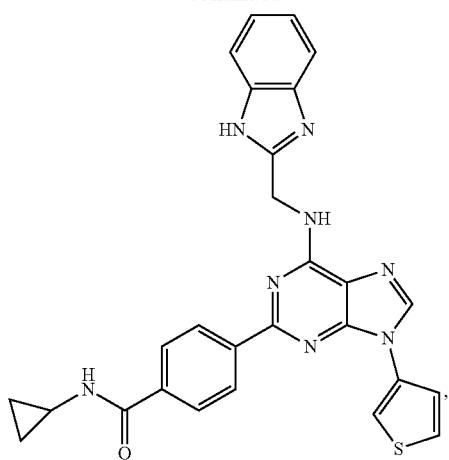
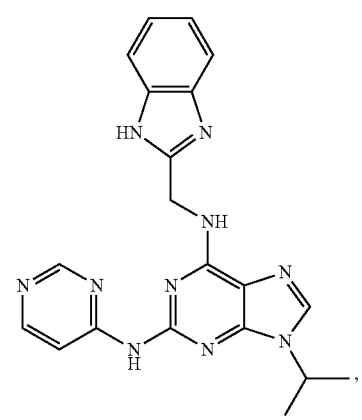
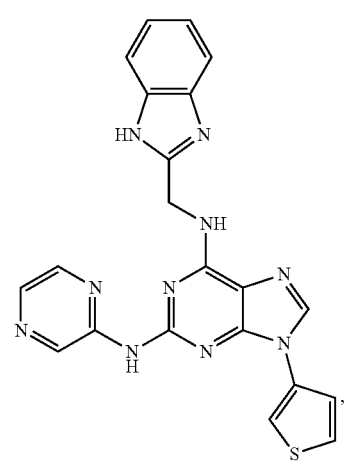
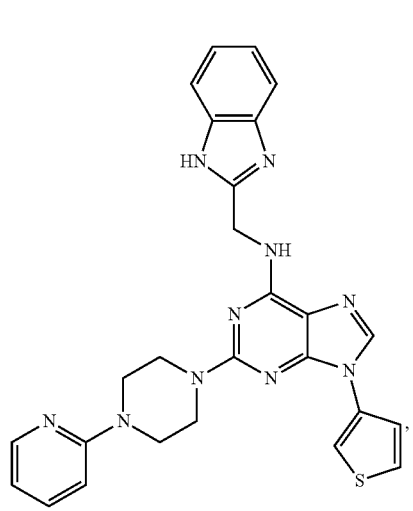
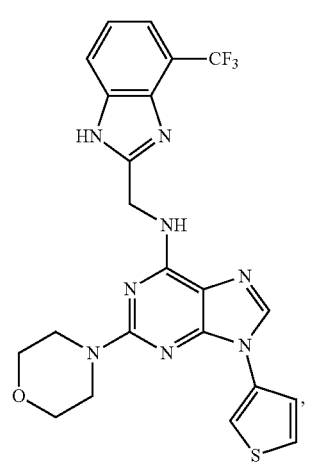

99
-continued
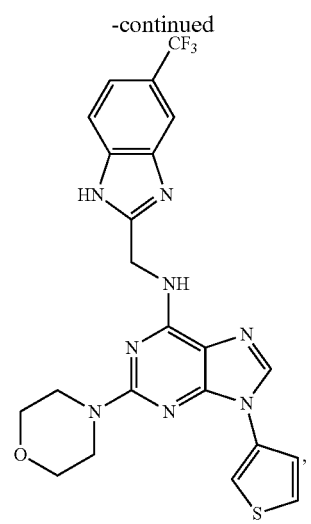
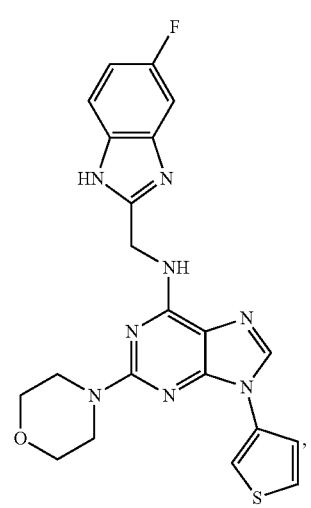
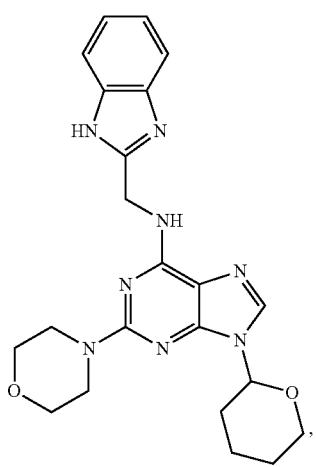
100
-continued
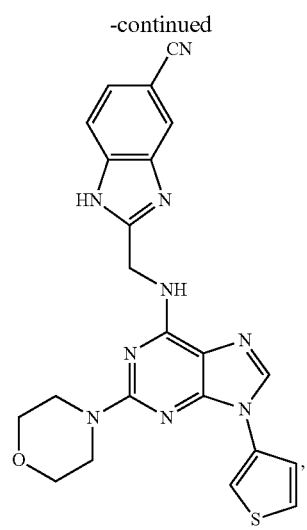
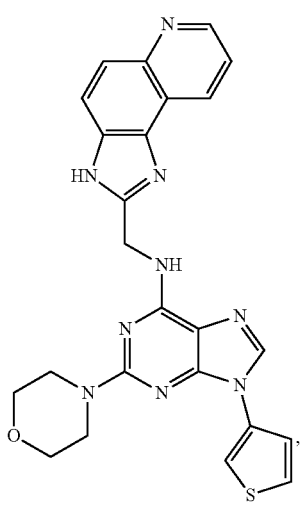
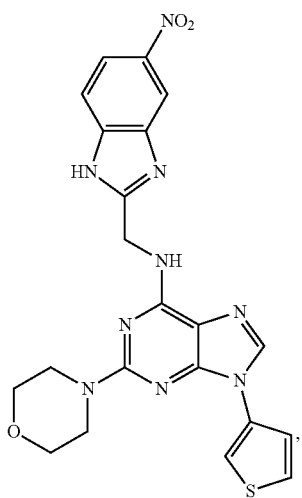

101
-continued
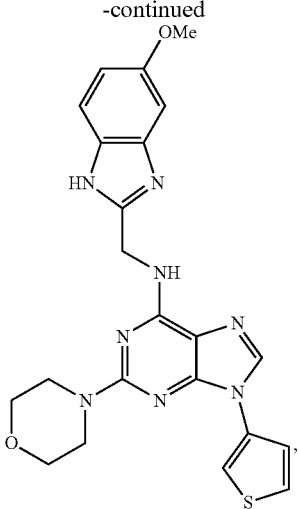
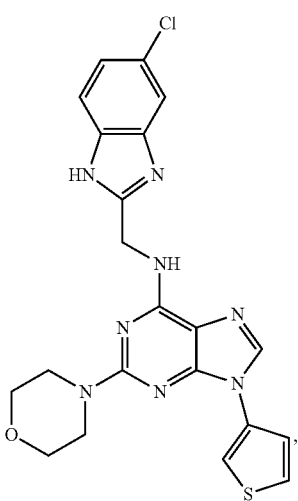
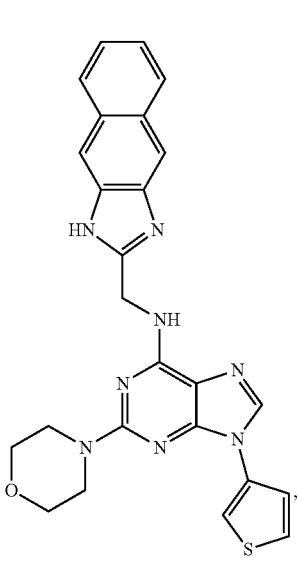
102
-continued
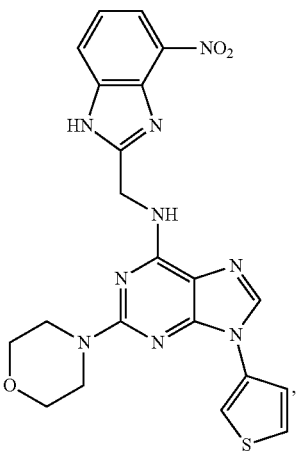
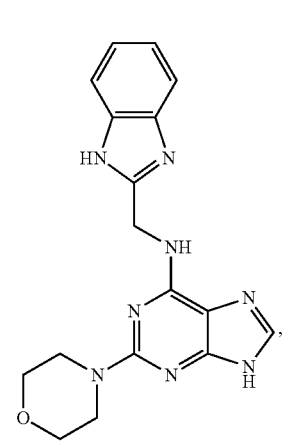
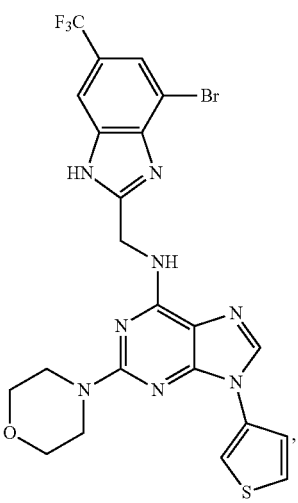

103
-continued
104
-continued
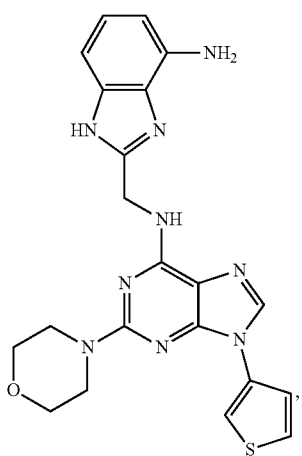
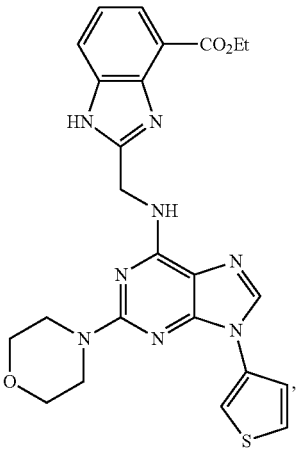

105
-continued
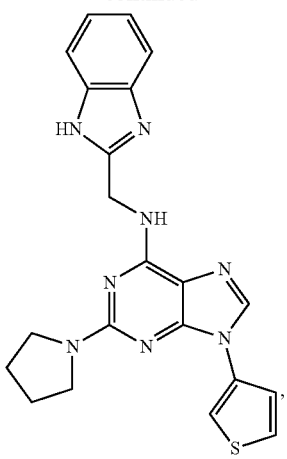
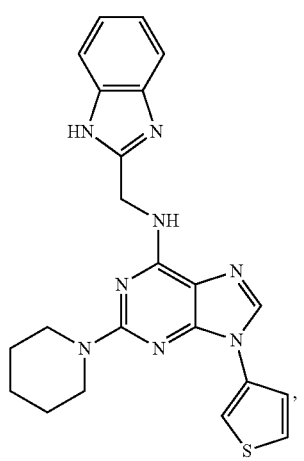
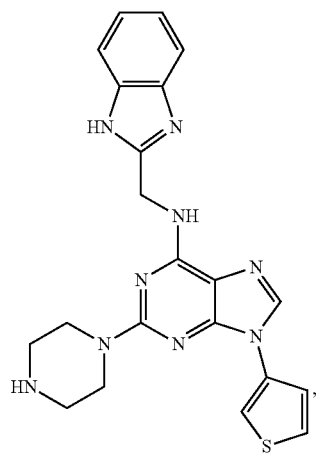
106
-continued
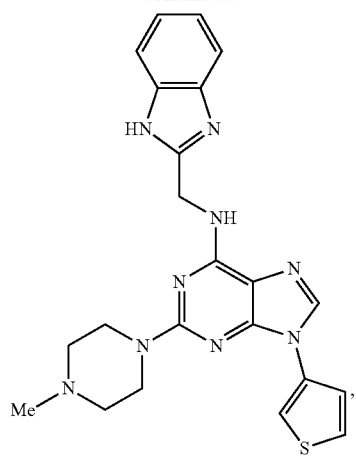
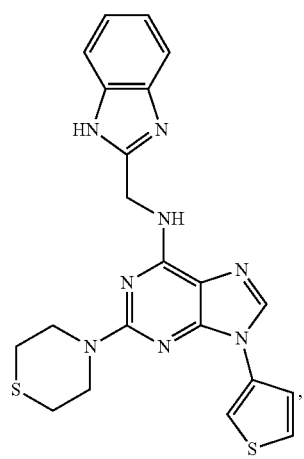
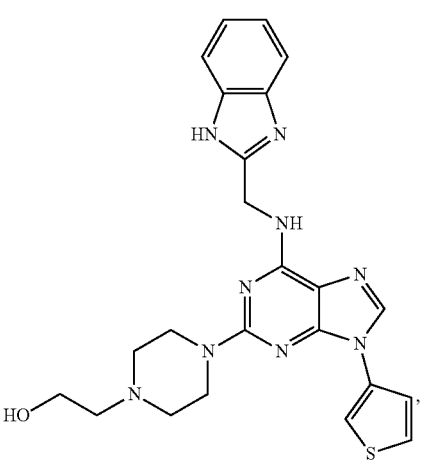

107
-continued
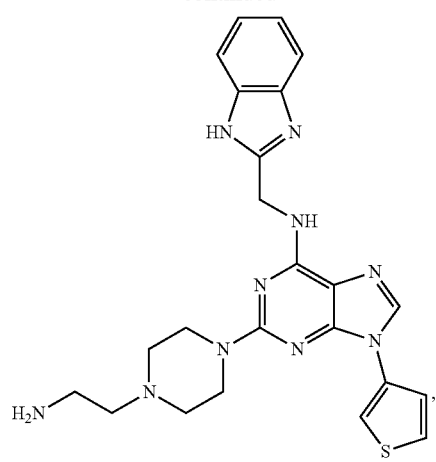
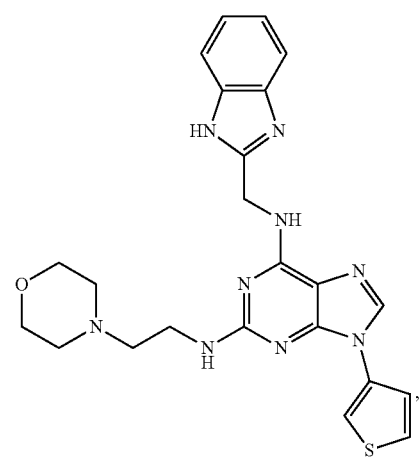
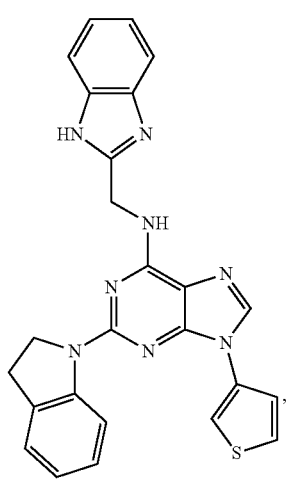
108
-continued
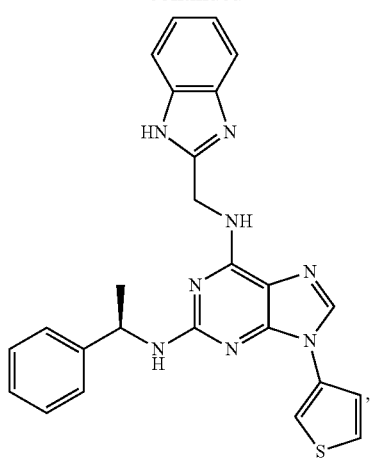
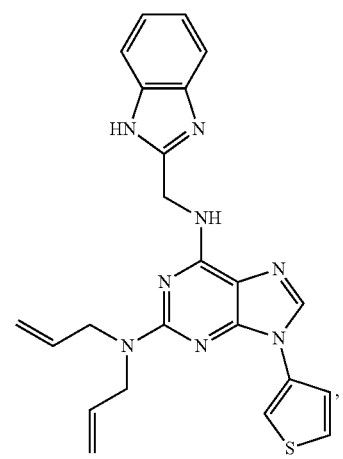
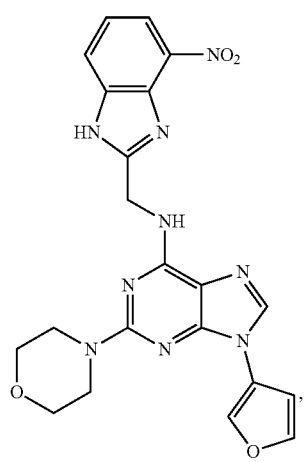

109
-continued
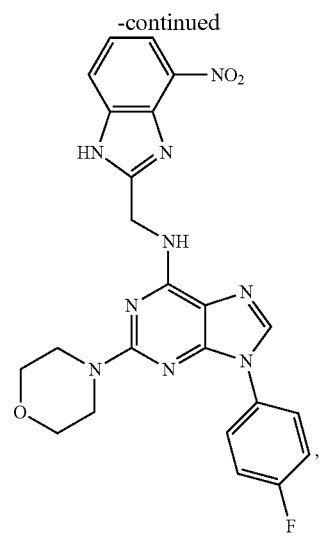
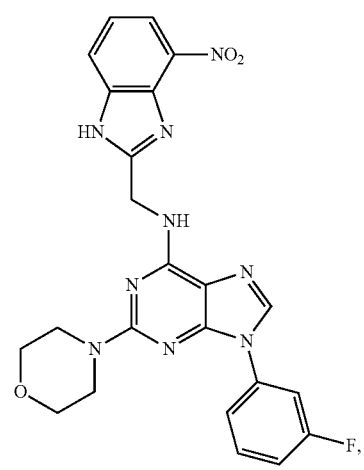
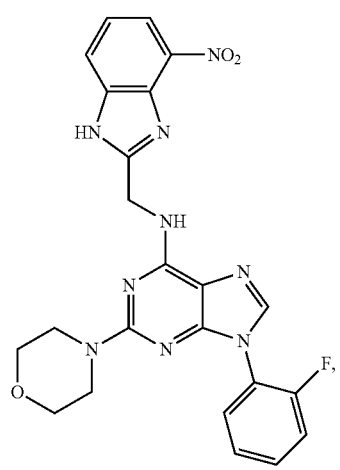
110
-continued
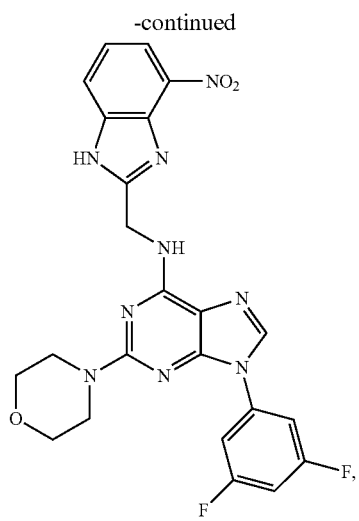
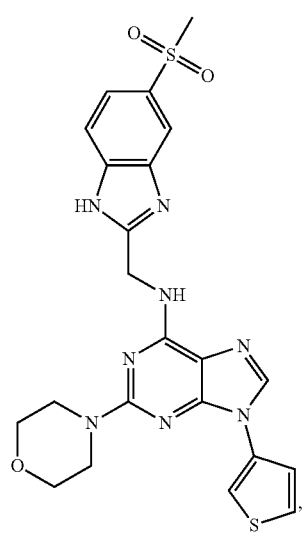
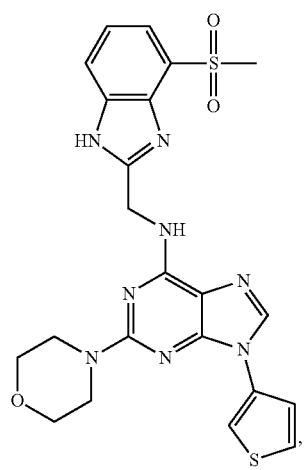

111
-continued
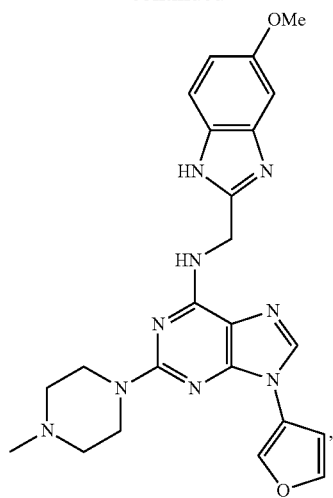
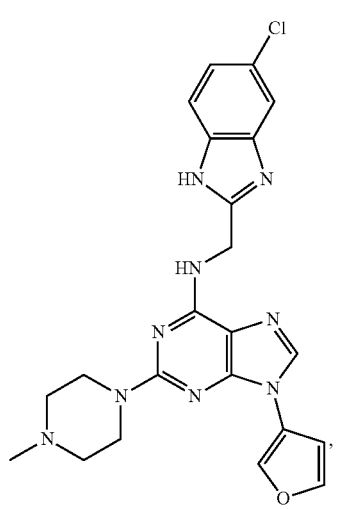
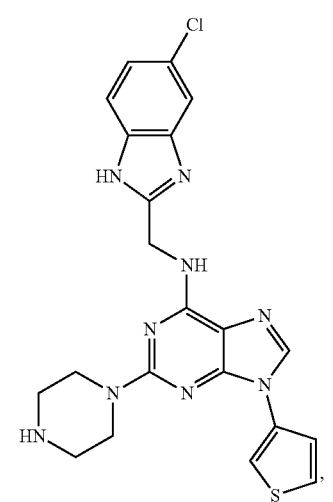
112
-continued
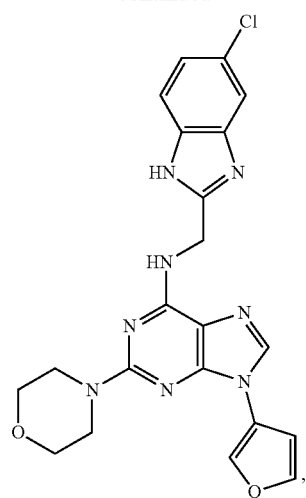
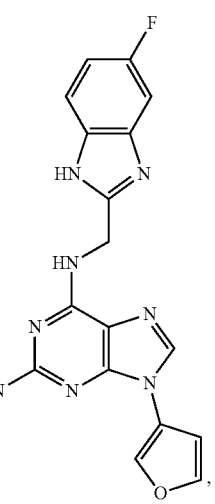
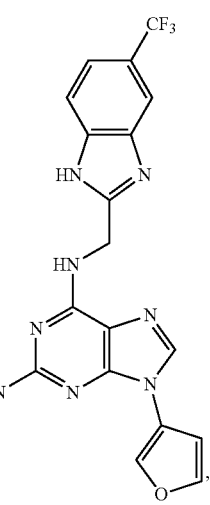

113
-continued
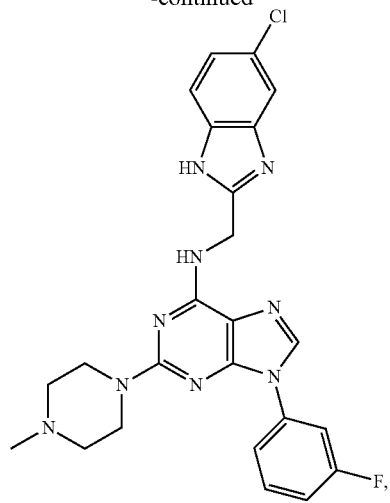
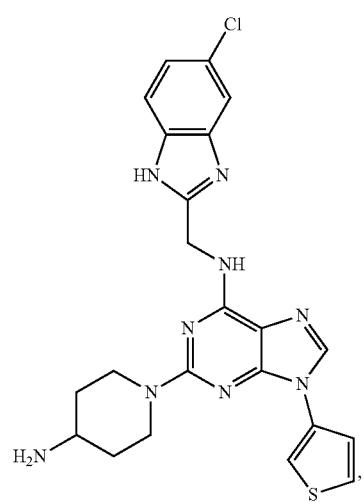
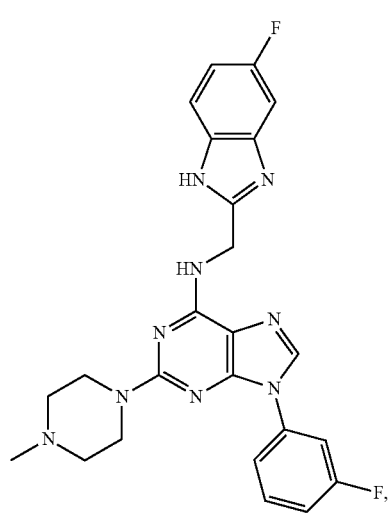
114
-continued
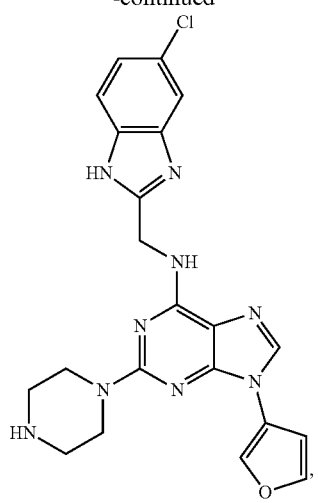
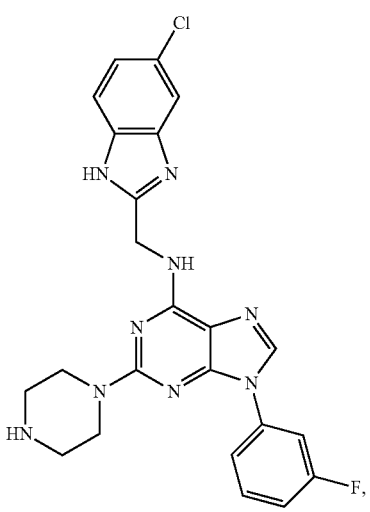
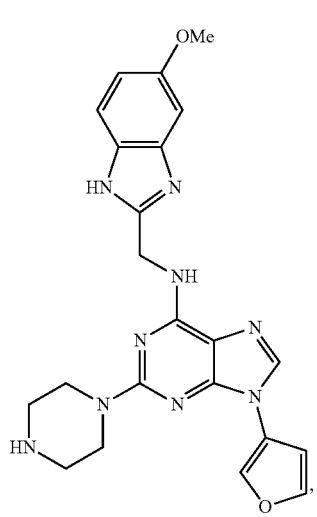

115
-continued
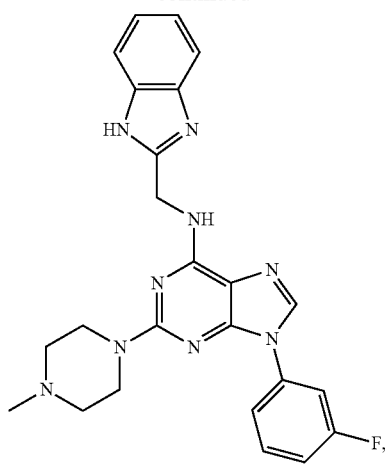
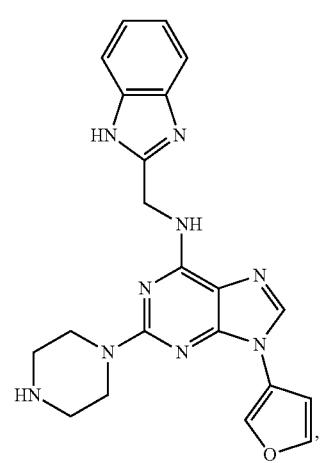
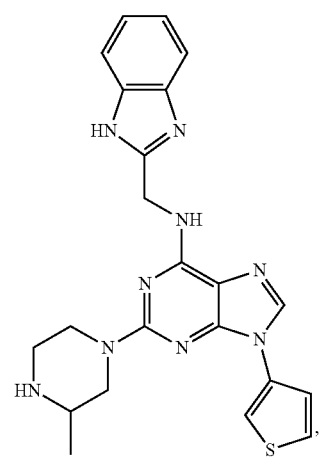
116
-continued
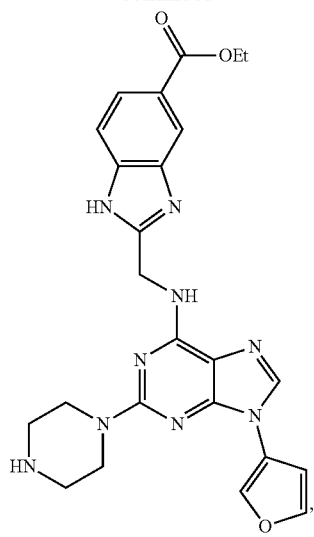
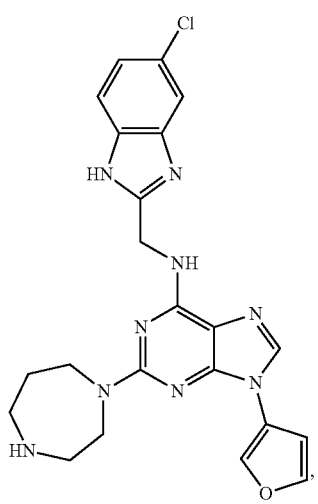

117
-continued
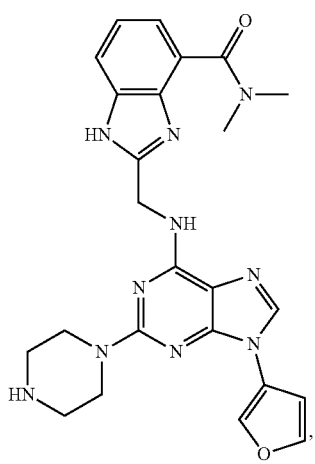
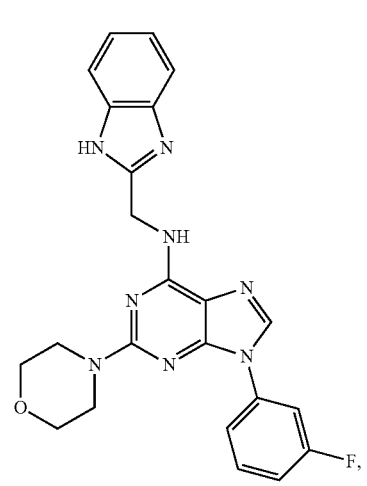
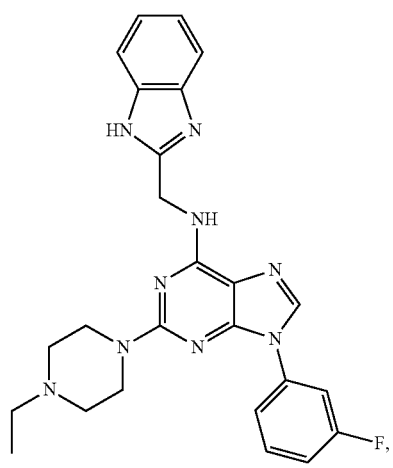
118
-continued
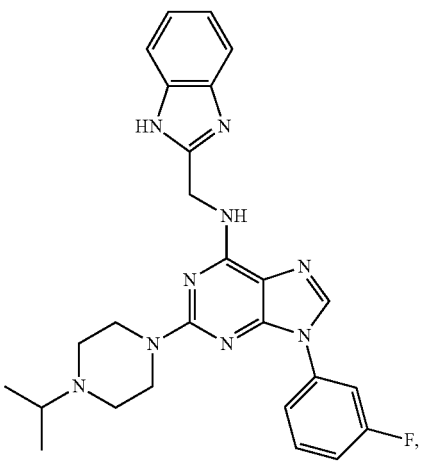
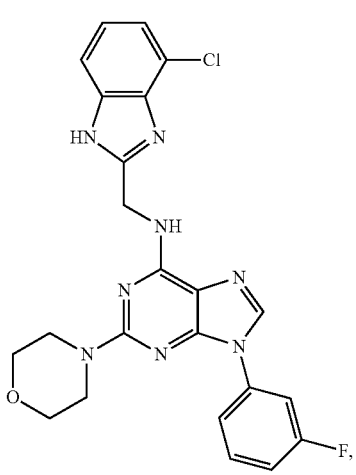
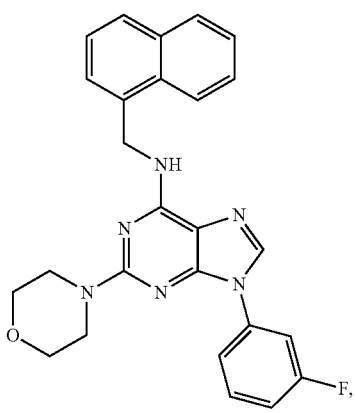

119
-continued
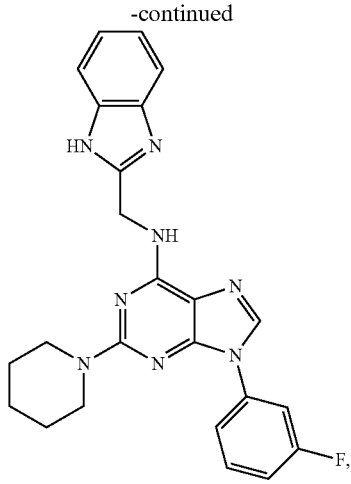
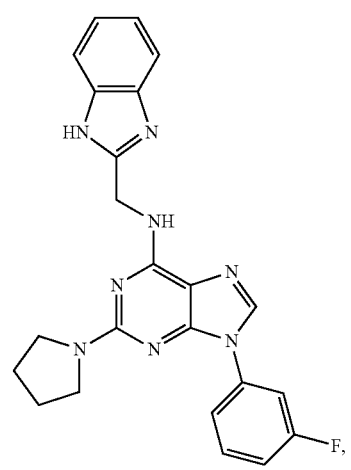
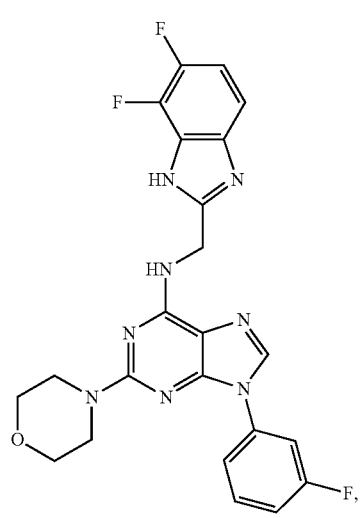
120
-continued
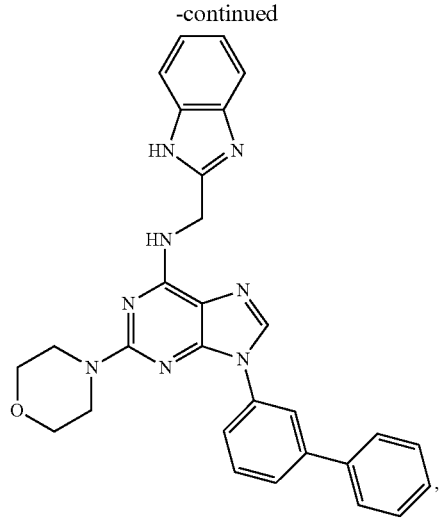
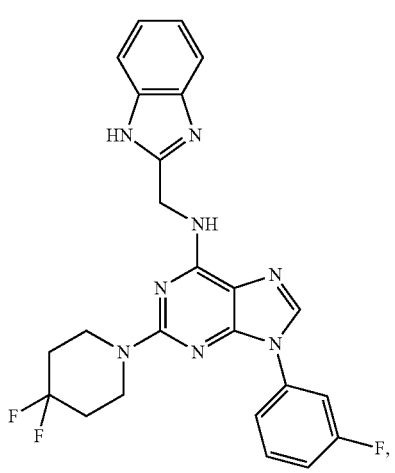
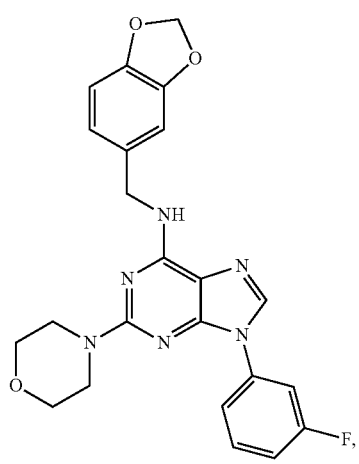

121
-continued
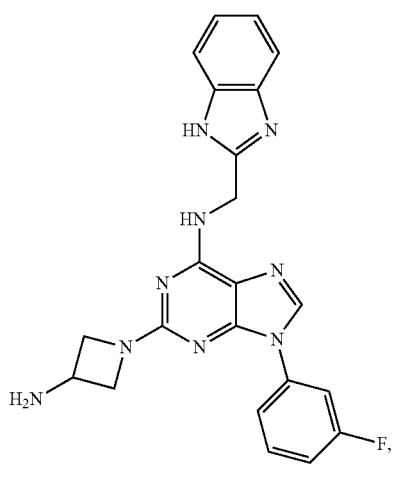
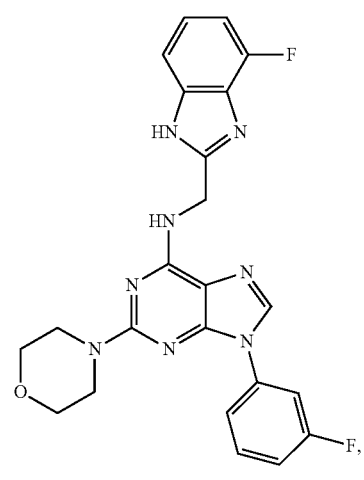
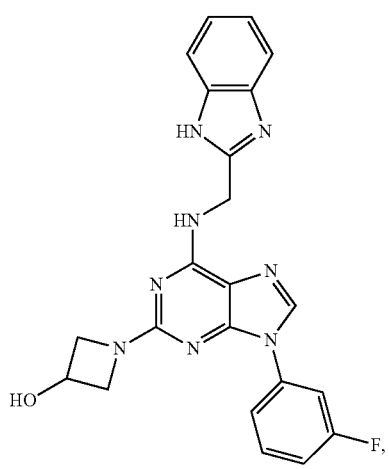
122
-continued
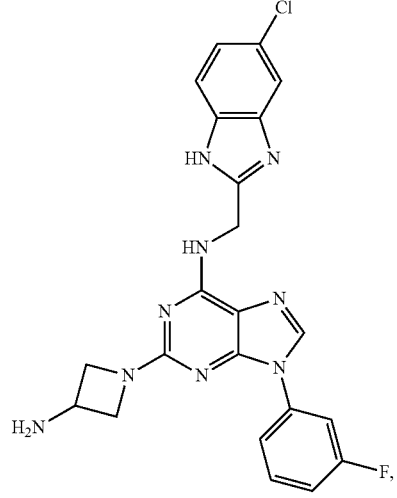
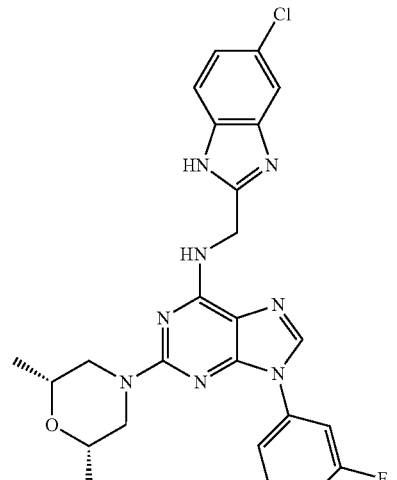
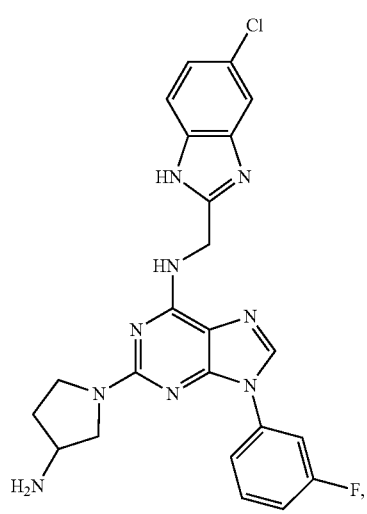

-continued

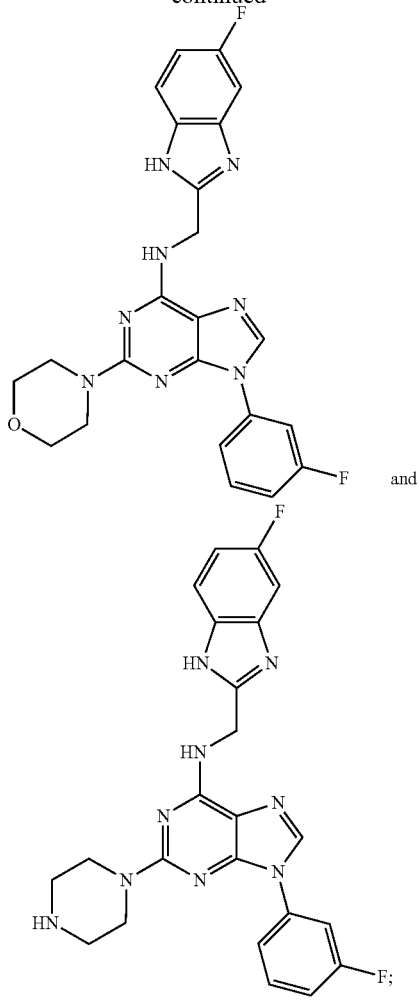

or any salt, hydrate, prodrug, and metabolite thereof.

Embodiment 19. The compound of claim 1 wherein the compound is

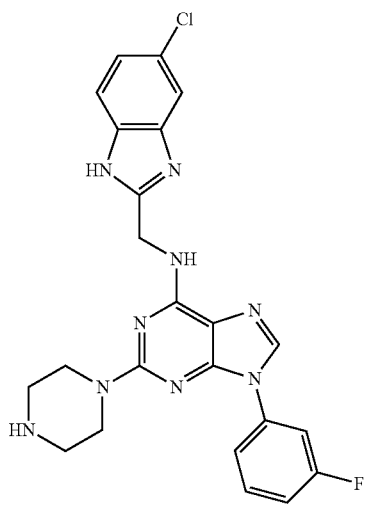 [SMILES: Fc1cccc(-n2cnc3c(NCc4nc5cc(Cl)ccc5[nH]4)nc(N4CCNCC4)nc32)c1]

or any salt, hydrate, prodrug, and metabolite thereof.

Embodiment 20. The compound of claim 1 wherein the compound is

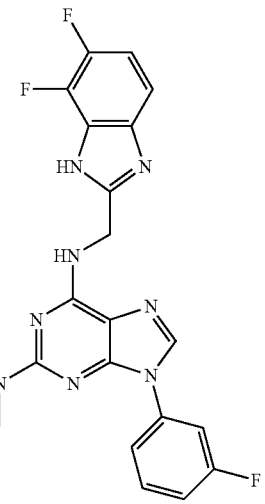

or any salt, hydrate, prodrug, and metabolite thereof.

Embodiment 21. A pharmaceutical composition comprising a compound of any one of embodiment 1-20 and a pharmaceutically acceptable carrier.

Embodiment 22. The compound of any one of embodiments 1-20 wherein the compound reduces amyloid beta 40 production.

Embodiment 23. The compound of any one of embodiments 1-20 wherein the compound inhibits the degradation of Wee1.

Embodiment 24. The compound of any one of embodiments 1-20 wherein the compound inhibits cell proliferation.

Embodiment 25. The compound of any one of embodiments 1-20 wherein the compound inhibits casein kinase 1 (CK1).

Embodiment 26. A method of reducing amyloid beta 40 production comprising contacting one or more cells with an effective amount of the compound of any one of embodiments 1-25.

Embodiment 27. A method of reducing cell proliferation comprising contacting one or more cells with an effective amount of the compound of any one of embodiments 1-25.

Embodiment 28. A method of inhibiting the degradation of Wee1 comprising contacting one or more cells with an effective amount of the compound of any one of embodiments 1-25.

Embodiment 29. A method of inhibiting casein kinase 1 (CK1) comprising contacting one or more cells with an effective amount of the compound of any one of embodiments 1-25.

Embodiment 30. The method of any one of embodiments 26-29 wherein the contacting is in vivo in a human patient.

Embodiment 31. The method of any one of embodiments 26-30 wherein the amount or concentration of the compound is effective to selectively inhibit the degradation of Wee1.

Embodiment 32. A method of treatment of a malcondition in a patient for which inhibition of the degradation of Wee1 is medically indicated, comprising administering to the patient a compound of any one of embodiments 1-25 in a dose, at a frequency, and for a duration sufficient to provide a beneficial effect to the patient.

Embodiment 33. The method of embodiment 32 wherein the malcondition comprises cancer, Alzheimer's, neurological disorders, psychiatric disorders, or inflammation-related disorders.

Embodiment 34. Use of a compound of any one of embodiments 1-25 in treatment of a malcondition in a human patient.

Embodiment 35. The use of embodiment 34 wherein inhibition of the degradation of Wee1 is medically indicated for treatment of the malcondition.

Embodiment 36. The use of embodiment 34 wherein the malcondition comprises cancer, Alzheimer's, neurological disorders, psychiatric disorders, or inflammation-related disorders, or combinations thereof.

Embodiment 37: A method of treatment of a malcondition comprising cancer, Alzheimer's, neurological disorders, psychiatric disorders, or inflammation-related disorders, in a patient afflicted therewith, comprising administering to the patient an effective amount of a compound of any one of claims 1-25, whereby a beneficial effect to the patient is achieved.

Embodiment 38. A method of synthesis of a compound of any one of embodiments 1-25, comprising:

contacting a 2,6-dihalopurine with an $R^1$-substituted boronic acid, to provide a 9-$R^1$-substituted-2,6-dihalopurine;

contacting the 9-R1-substituted-2,6-dihalopurine with an (1H-benzo[d]imidazol-2-yl)methanamine, to provide an N-((1H-benzo[d]imidazol-2-yl)methyl)-2-halo-9-$R^1$-substituted-purin-6-amine;

contacting the N-((1H-benzo[d]imidazol-2-yl)methyl)-2-halo-9-$R^1$-substituted-purin-6-amine with an H-substituted-$R^2$, to provide an N-((1H-benzo[d]imidazol-2-yl)methyl)-2-$R^2$-substituted-9-$R^1$-substituted-purin-6-amine of formula (I);

wherein $R^1$ and $R^2$ are as defined in embodiment 1.

Embodiment 39. The method of embodiment 38, wherein $R^1$ is 3-thiophenyl.

Embodiment 40. The method of embodiment 38, wherein $R^2$ is morpholinyl.

Embodiment 41. A method of synthesis of a compound of any one of embodiments 1-25, comprising:

contacting a 2,6-dihalopurine with an $R^1$-substituted boronic acid, to provide a 9-$R^1$-substituted-2,6-dihalopurine;

contacting a 3-$R^3$-substituted-benzene-1,2-diamine with N-[(9H-fluoren-9-ylmethoxy)carbonyl]glycine, to provide a (9H-fluoren-9-yl)methyl (2-((2-amino-3-$R^3$-substituted-phenyl)amino)-2-oxoethyl)carbamate;

intramolecularly condensing the (9H-fluoren-9-yl)methyl (2-((2-amino-3-$R^3$-substituted-phenyl)amino)-2-oxoethyl) carbamate, to provide a (4-$R^3$-substituted-1H-benzo[d]imidazol-2-yl)methanamine;

contacting the (4-$R^3$-substituted-1H-benzo[d]imidazol-2-yl)methanamine with the 9-$R^1$-substituted-2,6-dihalopurine, followed by contacting the intermediate with an H-substituted-$R^2$, to provide an N-((4-$R^3$-substituted-1H-benzo[d] imidazol-2-yl)methyl)-2-$R^2$-substituted-9-$R^1$-substituted-purin-6-amine of formula (I);

wherein $R^1$, $R^2$, and $R^3$ are as defined in embodiment 1.

Embodiment 42. The method of embodiment 41, wherein $R^1$ is 3-thiophenyl

Embodiment 43. The method of embodiment 41, wherein $R^2$ is morpholinyl.

Embodiment 44. The method of embodiment 41, wherein $R^3$ is nitro.

What is claimed is:
1. A compound of formula (I),

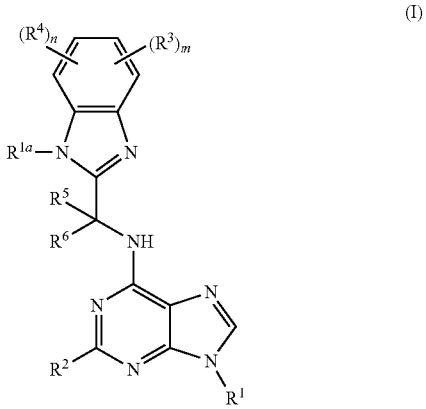

wherein
$R^1$ and $R^{1a}$ are each independently selected from the group consisting of hydrogen, deuterium, $(CH_2)_{0-4}N(R)_2$, $(CH_2)_{0-4}SO_3R$, $(CH_2)_{0-4}C(O)R$, $(CH_2)_{0-4}C(O)C(O)R$, $(CH_2)_{0-4}C(O)CH_2C(O)R$, $(CH_2)_{0-4}C(S)R$, $(CH_2)_{0-4}C(O)OR$, $(CH_2)_{0-4}OC(O)R$, $(CH_2)_{0-4}OC(O)OR$, $(CH_2)_{0-4}C(O)N(R)_2$, $OC(O)N(R)_2$, $(CH_2)_{0-4}C(S)N(R)_2$, $(CH_2)_{0-4}NHC(O)R$, $(CH_2)_{0-4}N(R)SO_2R$, $(CH_2)_{0-4}N(R)SO_2N(R)_2$, $(CH_2)_{0-4}N(R)C(O)OR$, $(CH_2)_{0-4}N(R)C(O)R$, $(CH_2)_{0-4}N(R)C(S)R$, $(CH_2)_{0-4}N(R)C(O)N(R)_2$, $(CH_2)_{0-4}N(R)C(S)N(R)_2$, $(CH_2)_{0-4}N(COR)COR$, $(CH_2)_{0-4}N(OR)R$, $(CH_2)_{0-4}C(=NH)N(R_2)$, $(CH_2)_{0-4}C(O)N(OR)R$, $(CH_2)_{0-4}C(=NOR)R$, $(C_{1-4})$alkyl, $(C_{1-4})$alkoxy, $(C_{1-4})$acyloxy, cycloalkyl, heterocyclyl, aryl, and heteroaryl; wherein any alkyl, alkoxy, acyloxy, cycloalkyl, heterocyclyl, aryl, heteroaryl can be mono- or independently multi-substituted with J, $(C_{1-6})$alkyl, $(C_{2-6})$alkenyl, $(C_{2-6})$alkynyl, $(C_{1-6})$haloalkyl, $(C_{1-6})$alkoxy, $(C_{1-6})$haloalkoxy, cycloalkyl$(C_{0-6})$alkyl, heterocyclyl$(C_{0-6})$alkyl, aryl$(C_{0-6})$alkyl, or heteroaryl$(C_{0-6})$alkyl, of which any alkyl, alkenyl, alkynyl, haloalkyl, alkoxy, haloalkoxy, cycloalkyl, aryl, heterocyclyl, or heteroaryl can be further substituted with J;

wherein $R^2$ is morpholino which can be mono- or independently multi-substituted with J, $(C_{2-6})$alkenyl, $(C_{2-6})$alkynyl, $(C_{1-6})$haloalkyl, $(C_{1-6})$alkoxy, $(C_{1-6})$haloalkoxy, cycloalkyl$(C_{0-6})$alkyl, heterocyclyl$(C_{0-6})$alkyl, aryl$(C_{0-6})$alkyl, or heteroaryl$(C_{0-6})$alkyl;

$R^3$, $R^4$, $R^5$, and $R^6$ each are independently selected from the group consisting of F, Cl, Br, I, OR, CN, $CF_3$, $OCF_3$, $NO_2$, R, $(CH_2)_{0-4}N(R)_2$, $(CH_2)_{0-4}SR$, $(CH_2)_{0-4}SOR$, $(CH_2)_{0-4}SO_2R$, $(CH_2)_{0-4}SO_2N(R)_2$, $(CH_2)_{0-4}SO_3R$, $(CH_2)_{0-4}C(O)R$, $(CH_2)_{0-4}C(O)C(O)R$, $(CH_2)_{0-4}C(O)CH_2C(O)R$, $(CH_2)_{0-4}C(S)R$, $(CH_2)_{0-4}C(O)OR$, $(CH_2)_{0-4}OC(O)R$, $(CH_2)_{0-4}OC(O)OR$, $(CH_2)_{0-4}C(O)N(R)_2$, $(CH_2)_{0-4}OC(O)N(R)_2$, $(CH_2)_{0-4}C(S)N(R)_2$, $(CH_2)_{0-4}NHC(O)R$, $(CH_2)_{0-4}N(R)N(R)C(O)R$, $(CH_2)_{0-4}N(R)N(R)C(O)OR$, $(CH_2)_{0-4}N(R)N(R)CON(R_2)$, $(CH_2)_{0-4}N(R)SO_2R$, $(CH_2)_{0-4}N(R)SO_2N(R)_2$, $(CH_2)_{0-4}N(R)C(O)OR$, $(CH_2)_{0-4}N(R)C(O)R$, $(CH_2)_{0-4}N(R)C(S)R$, $(CH_2)_{0-4}N(R)C(O)N(R)_2$, $(CH_2)_{0-4}N(R)C(S)N(R)_2$, $(CH_2)_{0-4}N(COR)COR$, $(CH_2)_{0-4}N(OR)R$, $(CH_2)_{0-4}C(=NH)N(R_2)$, $(CH_2)_{0-4}C(O)N(OR)R$, $(CH_2)_{0-4}C(=NOR)R$, $(C_{1-4})$alkyl, $(C_{1-4})$alkoxy, $(C_{1-4})$acyloxy, cycloalkyl, heterocyclyl, aryl, and heteroaryl; wherein any alkyl, alkoxy, acyloxy, cycloalkyl, heterocyclyl, aryl, heteroaryl can be mono- or independently multi-substituted with J, $(C_{1-6})$alkyl, $(C_{2-6})$alkenyl, $(C_{2-6})$alkynyl, $(C_{1-6})$haloalkyl, $(C_{1-6})$alkoxy, $(C_{1-6})$haloalkoxy, cycloalkyl$(C_{0-6})$alkyl, heterocyclyl$(C_{0-6})$alkyl, aryl$(C_{0-6})$alkyl, or heteroaryl$(C_{0-6})$alkyl; wherein any alkyl, alkenyl, alkynyl, haloalkyl, alkoxy, haloalkoxy, cycloalkyl, aryl, heterocyclyl, or heteroaryl can be further substituted with J;

wherein m and n are each independently 0, 1, 2, or 3, provided m plus n is less than or equal to 4;

wherein J independently at each occurrence is selected from the group consisting of F, Cl, Br, I, OR, CN, $CF_3$, $OCF_3$, $NO_2$, R, O, S, C(O), C(S), S(O), methylenedioxy, ethylenedioxy, $N(R)_2$, SR, SOR, $SO_2R$, $SO_2N(R)_2$, $SO_3R$, C(O)R, C(O)C(O)R, $C(O)CH_2C(O)R$, C(S)R, C(O)OR, OC(O)R, OC(O)OR, $C(O)N(R)_2$, $OC(O)N(R)_2$, $C(S)N(R)_2$, $(CH_2)_{0-4}NHC(O)R$, N(R)N(R)C(O)R, N(R)N(R)C(O)OR, $N(R)N(R)CON(R_2)$, $N(R)SO_2R$, $N(R)SO_2N(R)_2$, N(R)C(O)OR, N(R)C(O)R, N(R)C(S)R, $N(R)C(O)N(R)_2$, $N(R)C(S)N(R)_2$, N(COR)COR, N(OR)R, $C(=NH)N(R_2)$, C(O)N(OR)R, C(=NOR)R, $(C_{1-4})$alkyl, $(C_{1-4})$alkoxy, $(C_{1-4})$acyloxy, cycloalkyl, heterocyclyl, aryl, and heteroaryl; wherein any alkyl, alkoxy, acyloxy, cycloalkyl, heterocyclyl, aryl, hetero aryl can be mono- or independently multi-substituted with R, $(C_{1-6})$alkyl, $(C_{2-6})$alkenyl, $(C_{2-6})$alkynyl, $(C_{1-6})$haloalkyl, $(C_{1-6})$alkoxy, $(C_{1-6})$haloalkoxy, cycloalkyl$(C_{0-6})$alkyl, heterocyclyl$(C_{0-6})$alkyl, aryl$(C_{0-6})$alkyl, or heteroaryl$(C_{0-6})$alkyl; wherein any alkyl, alkenyl, alkynyl, haloalkyl, alkoxy, haloalkoxy, cycloalkyl, aryl, heterocyclyl, or heteroaryl can be further mono- or independently multi-substituted with R; or wherein two R groups together with a nitrogen atom or with two adjacent nitrogen atoms to which they are bonded can together form a $(C_{3-8})$ heterocyclyl mono- or multi-substituted with R; optionally further including 1-3 additional hetero atoms selected from the group consisting of O, N, S, S(O) and $S(O)_2$;

wherein R is independently at each occurrence is selected from the group consisting of hydrogen, deuterium, F, Cl, Br, I, OH, CN, $CF_3$, $OCF_3$, $NO_2$, alkyl, cycloalkyl, cycloalkylalkyl, aryl, aralkyl, heterocyclyl, heterocyclylalkyl, heteroaryl, and heteroarylalkyl; wherein any alkyl, cycloalkyl, cycloalkylalkyl, aryl, aralkyl, heterocyclyl, heterocyclylalkyl, heteroaryl, or heteroarylalkyl is substituted with 0-3 $J^R$; or wherein two R groups with a nitrogen atom or with two adjacent nitrogen atoms to which they are bonded can together form a $(C_{3-8})$ heterocyclyl substituted with 0-3 $J^R$; optionally further comprising 1-3 additional heteroatoms selected from the group consisting of O, N, S, S(O) and $S(O)_2$;

wherein any cycloalkyl, aryl, heterocyclyl, or heteroaryl can be fused, bridged, or in a spiro configuration with one or more additional optionally mono- or independently multi-$J^R$ substituted cycloalkyl, aryl, heterocyclyl, and heteroaryl, monocyclic, bicyclic, bicyclic or polycyclic, saturated, partially unsaturated, or aromatic rings;

wherein $J^R$ is independently at each occurrence is selected from the group consisting of F, Cl, Br, I, OR, CN, $CF_3$, $OCF_3$, $NO_2$, O, S, C(O), C(S), S(O), methylenedioxy, ethylenedioxy, $N(R)_2$, SR, SOR, $SO_2R$, $SO_2N(R)_2$, $SO_3R$, C(O)R, C(O)C(O)R, $C(O)CH_2C(O)R$, C(S)R, C(O)OR, OC(O)R, OC(O)OR, $C(O)N(R)_2$, $OC(O)N(R)_2$, $C(S)N(R)_2$, $(CH_2)_{0-4}NHC(O)R$, N(R)N(R)C(O)R, N(R)N(R)C(O)OR, $N(R)N(R)CON(R_2)$, $N(R)SO_2R$, $N(R)SO_2N(R)_2$, N(R)C(O)OR, N(R)C(O)R, N(R)C(S)R, $N(R)C(O)N(R)_2$, $N(R)C(S)N(R)_2$, N(COR)COR, N(OR)R, $C(=NH)N(R_2)$, C(O)N(OR)R, C(=NOR)R, $(C_{1-4})$alkyl, $(C_{1-4})$alkoxy, $(C_{1-4})$acyloxy, cycloalkyl, heterocyclyl, aryl, and heteroaryl;

wherein the compound of formula (I) can be any stereoisomer thereof, or any salt or tautomer thereof.

2. The compound of claim 1 wherein the compound is selected from the group consisting of

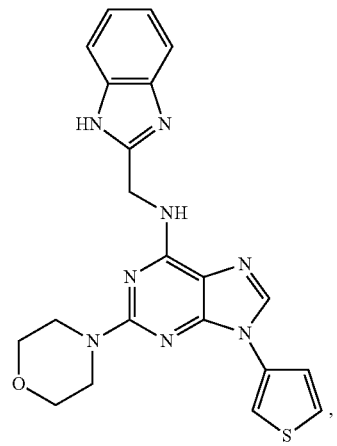

,

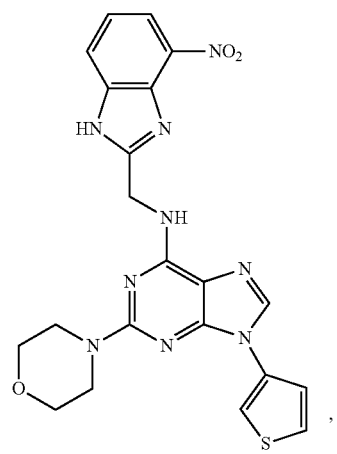

,

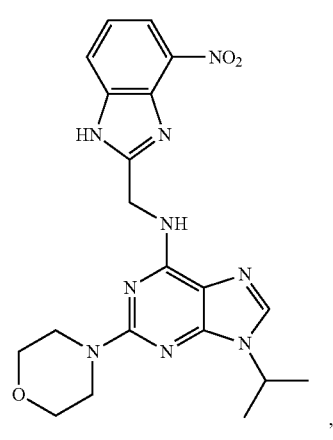

,

129
-continued
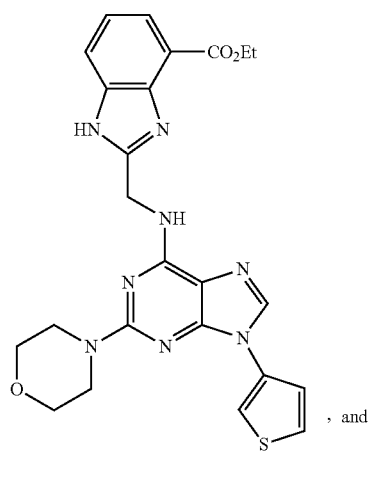
, and
130
-continued
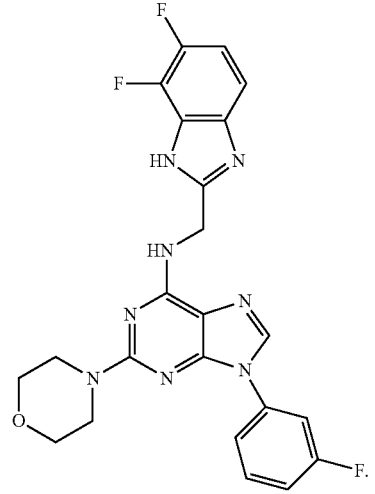
.
* * * * *